(12) United States Patent
Chin et al.

(10) Patent No.: US 10,777,301 B2
(45) Date of Patent: Sep. 15, 2020

(54) HIERARCHICAL GENOME ASSEMBLY METHOD USING SINGLE LONG INSERT LIBRARY

(71) Applicant: Pacific Biosciences of California, Inc., Menlo Park, CA (US)

(72) Inventors: Chen-Shan Chin, San Leandro, CA (US); Patrick Marks, San Francisco, CA (US); David Alexander, Mountain View, CA (US); Aaron Klammer, Mountain View, CA (US); Stephen W Turner, Menlo Park, CA (US)

(73) Assignee: Pacific Biosciences for California, Inc., Menlo Park, CA (US)

( * ) Notice: Subject to any disclaimer, the term of this patent is extended or adjusted under 35 U.S.C. 154(b) by 699 days.

(21) Appl. No.: 13/941,442

(22) Filed: Jul. 12, 2013

(65) Prior Publication Data

US 2014/0025312 A1    Jan. 23, 2014

Related U.S. Application Data

(60) Provisional application No. 61/671,554, filed on Jul. 13, 2012, provisional application No. 61/784,219, filed on Mar. 14, 2013.

(51) Int. Cl.
  *G16B 30/00* (2019.01)
  *G16B 20/00* (2019.01)

(52) U.S. Cl.
  CPC ............ *G16B 30/00* (2019.02); *G16B 20/00* (2019.02)

(58) Field of Classification Search
  None
  See application file for complete search history.

(56) References Cited

U.S. PATENT DOCUMENTS

| | | | |
|---|---|---|---|
| 7,056,661 B2 | 6/2006 | Korlach et al. | |
| 7,626,704 B2 | 12/2009 | Lundquist et al. | |
| 7,995,202 B2 | 8/2011 | Lundquist et al. | |
| 8,182,993 B2 | 5/2012 | Tomaney et al. | |
| 8,370,079 B2 | 2/2013 | Sorenson et al. | |
| 8,465,922 B2 | 6/2013 | Eid et al. | |
| 8,535,882 B2 | 9/2013 | Christians et al. | |
| 2011/0257889 A1 | 10/2011 | Klammer et al. | |
| 2012/0015825 A1 | 1/2012 | Zhong et al. | |
| 2012/0330566 A1 | 12/2012 | Chaisson | |
| 2013/0138358 A1 | 5/2013 | Tang et al. | |

OTHER PUBLICATIONS

Bashir et al. Nature Biotech. (2012) vol. 30, No. 7:701-709.*
Chaisson et al. (BMC Bioinformatics (2012) vol. 13:e—pp. 1-17).*
Chin et al. (Nature Methods (Jun. 2013) vol. 10:563-571).*
David et al. (Bioinformatics (2011) vol. 27:1011-1012).*
Huddleston et al. (Genome Research (2014) vol. 24:688-696).*
Lin et al. (Bioinformatics (2008) vol. 24:2431-2437).*
Misra et al. (Bioinformatics (2011) vol. 27:189-195).*
Eid et al., "Real-Time DNA Sequencing From Single Polymerase Molecules," Science (2009) 323:133-138.
Levene et al., "Zero-mode Waveguides for Single-molecule Analysis at High Concentration" Science (2003) 299:682-686.

\* cited by examiner

*Primary Examiner* — Lori A. Clow
(74) *Attorney, Agent, or Firm* — Morgan, Lewis & Bockius LLP

(57) ABSTRACT

The present invention is generally directed to a hierarchical genome assembly process for producing high-quality de novo genome assemblies. The method utilizes a single, long-insert, shotgun DNA library in conjunction with Single Molecule, Real-Time (SMRT®) DNA sequencing, and obviates the need for additional sample preparation and sequencing data sets required for previously described hybrid assembly strategies. Efficient de novo assembly from genomic DNA to a finished genome sequence is demonstrated for several microorganisms using as little as three SMRT® cells, and for bacterial artificial chromosomes (BACs) using sequencing data from just one SMRT® Cell. Part of this new assembly workflow is a new consensus algorithm which takes advantage of SMRT® sequencing primary quality values, to produce a highly accurate de novo genome sequence, exceeding 99.999% (QV 50) accuracy. The methods are typically performed on a computer and comprise an algorithm that constructs sequence alignment graphs from pairwise alignment of sequence reads to a common reference.

21 Claims, 47 Drawing Sheets

FIG. 7: Table 1B(a)

(Celera® Assembler was used for all samples unless otherwise noted in Table 1B(a)-(d).)
KEY: CLR = Continuous Long Read; PLRs = Pre-assembled Long Reads; RL = Read Length; RQ = Read Quality Escherichia coli (MG 1655):

| SMRT Cells | CLR bases (RL>500, RQ>80) | CLR coverage | Seed read bases (RL>5 kb) | Seed read coverage | Pre-assembly ratio | PLR bases | PLR coverage | loss |
|---|---|---|---|---|---|---|---|---|
| 8 | 460,967,046 | 99.4 | 139,984,665 | 30.2 | 3.3 | 99,561,718 | 21.5 | 29% |
| 6 | 340,710,636 | 73.4 | 104,805,545 | 22.6 | 3.3 | 72,869,727 | 15.7 | 30% |
| 4 | 231,998,701 | 50.0 | 69,215,698 | 14.9 | 3.4 | 46,685,198 | 10.1 | 33% |

| SMRT Cells | PLR nReads | PLR mean read length | PLR N50 read length | Assembly size | Number of contigs >10 kb (all) | Genome covered | N50 |
|---|---|---|---|---|---|---|---|
| 8 | 17,232 | 5,777 | 6,249 | 4,656,144 | 1(2) | 100.35% | 4,648,564 |
| 6 | 13,090 | 5,566 | 6,225 | 4,701,623 | 10(14) | 101.34% | 1,163,944 |
| 4 | 8,610 | 5,422 | 6,092 | 4,689,701 | 17(21) | 101.08% | 392,114 |

| SMRT Cells | Differences with Sanger reference | Concordance with Sanger reference | Nominal QV | Genes predicted (reference = 4314) | Full-length matched ORF prediction | % full-length matched ORF prediction |
|---|---|---|---|---|---|---|
| 8 | 23 | 99.999506% | 53.1 | 4340 | 4305 | 99.8% |
| 6 | 29 | 99.999383% | 52.1 | 4379 | 4314 | 100.0% |
| 4 | 58 | 99.998763% | 49.1 | 4385 | 4264 | 98.8% |

FIG. 7:
Table 1B(b)

Meiothermus ruber (DSM 1279):

| SMRT Cells | CLR bases (RL>500, RQ>80) | CLR coverage | Seed read bases (RL>5kb) | Seed read coverage | Pre-assembly ratio | PLR bases | PLR coverage | loss |
|---|---|---|---|---|---|---|---|---|
| 4 | 333,694,433 | 107.7 | 91,924,715 | 29.7 | 3.6 | 57,725,745 | 18.6 | 37% |
| 3 | 248,483,890 | 80.2 | 71,195,337 | 23.0 | 3.5 | 47,549,254 | 15.4 | 33% |
| 2 | 170,450,861 | 55.0 | 49,726,010 | 16.1 | 3.4 | 34,958,549 | 11.3 | 30% |

| SMRT Cells | PLR nReads | PLR mean read length | PLR N50 read length | Assembly size | Number of contigs | Genome covered | N50 |
|---|---|---|---|---|---|---|---|
| 4 | 12,151 | 4,750 | 5,228 | 3,098,781 | 1 | 100.04% | 3,098,781 |
| 3 | 9,829 | 4,837 | 5,287 | 3,098,729 | 1 | 100.04% | 3,098,729 |
| 2 | 7,212 | 4,847 | 5,292 | 3,102,769 | 3 | 100.17% | 1,053,479 |

| SMRT Cells | Differences with Sanger reference | Concordance with Sanger reference | Nominal QV | Genes predicted (reference = 3075) | Full-length matched ORF prediction | % full-length matched ORF prediction |
|---|---|---|---|---|---|---|
| 4 | 11 | 99.999645% | 54.5 | 3082 | 3057 | 99.4% |
| 3 | 13 | 99.999580% | 53.8 | 3085 | 3052 | 99.3% |
| 2 | 32 | 99.998969% | 49.9 | 3103 | 3049 | 99.2% |

FIG. 7: Table 1B(c)

Pedobacter heparinus (DSM 2366):

| SMRT Cells | CLR bases (RL>500, RQ>80) | CLR coverage | Seed read bases (RL>5kb) | Seed read coverage | Pre-assembly ratio | PLR bases | PLR coverage | loss |
|---|---|---|---|---|---|---|---|---|
| 7 | 485,065,907 | 93.9 | 126,844,131 | 24.5 | 3.8 | 81,589,199 | 15.8 | 36% |
| 7* | 485,065,907 | 93.9 | 126,844,131 | 24.5 | 3.8 | 81,589,199 | 15.8 | 36% |
| 6 | 407,845,228 | 78.9 | 106,229,674 | 20.6 | 3.8 | 70,962,835 | 13.7 | 33% |
| 6* | 407,845,228 | 78.9 | 106,229,674 | 20.6 | 3.8 | 70,962,835 | 13.7 | 33% |
| 4 | 274,252,271 | 53.1 | 71,599,274 | 13.9 | 3.8 | 49,301,344 | 9.5 | 31% |
| 4* | 274,252,271 | 53.1 | 71,599,274 | 13.9 | 3.8 | 49,301,344 | 9.5 | 31% |

| SMRT Cells | PLR nReads | PLR mean read length | PLR N50 read length | Assembly size | Number of contigs >10kb (all) | Genome covered | N50 |
|---|---|---|---|---|---|---|---|
| 7 | 17,548 | 4,649 | 5,063 | 5,171,533 | 2(3) | 100.08% | 2,927,691 |
| 7* | 17,548 | 4,649 | 5,063 | 5,197,624 | 1(5) | 100.59% | 5,164,849 |
| 6 | 15,112 | 4,695 | 5,092 | 5,173,388 | 2(3) | 100.12% | 2,928,902 |
| 6* | 15,112 | 4,695 | 5,092 | 5,174,349 | 2(3) | 100.13% | 3,511,353 |
| 4 | 10,602 | 4,650 | 5,086 | 5,184,825 | 11(18) | 100.34% | 1,403,814 |
| 4* | 10,602 | 4,650 | 5,086 | 5,196,690 | 15(22) | 100.57% | 1,258,275 |

| SMRT Cells | Differences with Sanger reference | Concordance with Sanger reference | Nominal QV | Genes predicted (reference = 4272) | Full-length matched ORF prediction | % full-length matched ORF prediction |
|---|---|---|---|---|---|---|
| 7 | 21 | 99.999594% | 53.9 | 4270 | 4247 | 99.4% |
| 7* | 21 | 99.999596% | 53.9 | 4267 | 4242 | 99.3% |
| 6 | 16 | 99.999691% | 55.1 | 4268 | 4241 | 99.3% |
| 6* | 16 | 99.999691% | 55.1 | 4271 | 4243 | 99.3% |
| 4 | 29 | 99.999441% | 52.5 | 4305 | 4228 | 99.0% |
| 4* | 26 | 99.999500% | 53.0 | 4316 | 4223 | 98.9% |

*using the MIRA assembler

FIG. 7:
Table 1B(d)

Human BAC (VMRC53-364D19) from one SMRT Cell:

| CLR bases (RL>500, RQ>80) | CLR coverage | Seed read bases (RL>5 kb) | Seed read coverage | Pre-assembly ratio | PLR bases | PLR coverage | loss |
|---|---|---|---|---|---|---|---|
| 85,544,722 | 454.4 | 11,812,181 | 63.5 | 7.2 | 5,027,597 | 27.0 | 57% |

| PLR nReads | PLR mean read length | PLR N50 read length | Assembly size | Number of contigs >10 kb (all) | Genome covered | N50 |
|---|---|---|---|---|---|---|
| 1,892 | 2,657 | 2,081 | 186,053 | 1(4*) | 100.00% | 186,053 |

*the 3 additional contigs were the result of *E. coli* contamination

Reference: *Escherichia coli* MG1655

Reference: *Meiothermus ruber* DSM 1279 chromosome, complete genome

Reference: *Pedobacter heparinus* DSM 2366 chromosome, complete genome

Reference: *Pedobacter haparinus* DSM 2366 chromosome, complete genome

FIG. 17

Algorithm 1 Generate $G_I$ from the alignments
---
1: $G_I \leftarrow G_B$
2: $v_{last} \leftarrow v_B$
3: for $p = 0 \ldots |A|$ do
4:    $q, r \leftarrow q_p, r_p$
5:    if $q = r$ and $q \neq$ "_" and $r \neq$ "_" then
6:       $v_{r_p} \leftarrow$ the node corresponding the reference base $r$ at alignment position $p$
7:       if $(e : v_{last} \rightarrow v_{r_p}) \in E_I$ then
8:          weight$(e) \leftarrow$ weight$(e) + 1$
9:       else
10:         create a new edge $(e : v_{last} \rightarrow v_{r_p})$, and add it into $G_I$
11:       end if
12:       $v_{last} \leftarrow v_{r_p}$
13:    else if $q \neq$ "_" and $r =$ "_" then
14:       create a new node $v_{q_p}$
15:       lable$(v_{q_p}) \leftarrow q$
16:       crate a new edge $e : v_{last} \rightarrow v_{q_p}$
17:       add $e$ and $v_{q_p}$ into $G_I$
18:       $v_{last} \leftarrow v_{q_p}$
19:    end if
20:    if $(e : v_{last} \rightarrow v_E) \in E_I$ then
21:       weight$(e) \leftarrow$ weight$(e) + 1$
22:    else
23:       create a new edge $(e : v_{last} \rightarrow v_E)$, and add it into $G_I$
24:    end if
25: end for

FIG. 19

Algorithm 2 Generate $G_S$ from $G_I$

1: function IN_EDGES($v$)
2:     return $\{e | u \in V_S, (e : u \to v) \in E_S\}$
3: end function
4: function OUT_EDGES($v$)
5:     return $\{e | u \in V_S, (e : v \to u) \in E_S\}$
6: end function
7: function OUT_NODES($v$)
8:     return $\{u | u \in V_S, (e : u \to v) \in \text{IN\_EDGES}(v)\}$
9: end function
10: function IN_NODES($v$)
11:     return $\{u | u \in V_S, (e : v \to u) \in \text{OUT\_EDGES}(u)\}$
12: end function
13: $G_S \leftarrow G_I$
14: for all $e \in G_I$ do
15:     visited($e$) $\leftarrow$ *False*
16: end for
17: $s \leftarrow$ an empty FIFO queue
18: for $v \in V_S$ do
19:     if | IN_EDGES($v$) | $= 0$ then
20:         push $v$ into $s$
21:     end if
22: end for
23: while $|s| \neq 0$ do
24:     $v \leftarrow \text{pop}(s)$
25:     MERGE_IN_NODE($v$)
26:     MERGE_OUT_NODE($v$)
27:     for all $e \in \text{OUT\_EDGES}(v)$ do
28:         visited($e$) $\leftarrow$ *True*
29:     end for
30:     for all $u \in \text{OUT\_NODES}(v)$ do
31:         if $|\{e | e \in \text{IN\_EDGES}(u), \text{visited}(e) = False\}| = 0$ then
32:             push $u$ into $s$
33:         end if
34:     end for
35: end while

FIG. 20

Algorithm 3 Merge in-nodes for the node $v$

1: function MERGE_IN_NODE($v$)
2:   for $l \in \{A, C, G, T\}$ do
3:     $U_l \leftarrow \{u | u \in \text{IN\_NODES}(v), |\text{OUT\_EDGE}(u)| = 1, \text{label}(u) = l\}$
4:     $\text{label}(u_l) \leftarrow l$
5:     add $(e: u_l \to v)$ to $G_s$
6:     $\text{visited}(e: u_l \to v) \leftarrow True$
7:     for all $u \in U_l$ do
8:       $\text{weight}(e: u_l \to v) \leftarrow \text{weight}(e: u_l \to v) + \text{weight}(e: u \to v)$
9:       for all $u' \in \text{IN\_NODES}(u)$ do
10:         add $(e: u' \to u_l)$ to $G_s$
11:         $\text{visited}(e: u' \to u_l) \leftarrow True$
12:         $\text{weight}(e: u' \to u_l) \leftarrow \text{weight}(e: u' \to u_l) + \text{weight}(e: u' \to u)$
13:         remove $(e: u' \to u)$ from $G_s$
14:       end for
15:       remove $u$ from $G_s$
16:     end for
17:     add $u_l$ to $G_s$
18:     MERGE_IN_NODE($u_l$)     ▷ Recursively merge upstream nodes
19:   end for
20: end function

FIG. 21

Algorithm 4 Merge out-nodes of the node $v$

1: function MERGE_OUT_NODE($v$)
2:   for $l \in \{A, C, G, T\}$ do
3:     $U_l \leftarrow \{u | u \in \text{OUT\_NODES}(v), |\text{IN\_EDGE}(u)| = 1, \text{label}(u) = l\}$
4:     label($u_l$) $\leftarrow l$
5:     add $(e : v \rightarrow u_l)$ to $G_s$
6:     visited$(e : v \rightarrow u_l) \leftarrow True$
7:     for all $u \in U_l$ do
8:       weight$(e : v \rightarrow u_l) \leftarrow$ weight$(e : v \rightarrow u_l) +$ weight$(e : v \rightarrow u_l)$
9:       for all $u' \in \text{OUT\_NODES}(u)$ do
10:         add $(e : u_l \rightarrow u')$ to $G_s$
11:         visited$(e : u_l \rightarrow u') \leftarrow True$
12:         weight$(e : u_l \rightarrow u') \leftarrow$ weight$(e : u_l \rightarrow u') +$ weight$(e : u \rightarrow u')$
13:         remove $(e : u \rightarrow u')$ from $G_s$
14:       end for
15:       remove $u$ from $G_s$
16:     end for
17:     add $u_l$ to $G_s$
18:     MERGE_OUT_NODE($u_l$)     ▷ Recursively merge downstream nodes
19:   end for
20: end function

FIG. 22

Algorithm 5 Find the best path in $G_s$ as the consensus sequence
```
1:  s ← an empty FIFO queue
2:  for all v ∈ V_s do
3:      if |OUT_EDGES(v)| = 0 then
4:          put v into s
5:          best_out_edge(v) ← ∅
6:          best_in_edge(v) ← ∅
7:          node_score(v) ← 0
8:      end if
9:  end for
10: for all e ∈ E_s do
11:     visited(e) ← False
12: end for
13: while |s| ≠ 0 do
14:     v ← pop(s)
15:     e_best ← ∅
16:     score_best ← ∅
17:     for (e_out : v → u) ∈ OUT_EDGES(v) do        ▷ find the best out-edge for node v
18:         score ← node_score(u)
19:         coverage ← the local coverage for the node u
20:         if u ∈ V_B then
21:             score_new ← score − δ        ▷ choose δ (default δ = 10) to make the path along the
    reference unfavorable
22:         else
23:             score_new ← weight(e_out) − coverage * 0.5 + score
24:         end if
25:         if score_best is ∅ or score_new > score_best then
26:             e_best ← e_out
27:             score_best ← score_new
28:         end if
29:     end for
30:     if e_best ≠ ∅ then
31:         best_score_edge(v) = e_best
32:         node_score(v) ← score_best
33:     end if
34:     for e ∈ IN_EDGES(v) do
35:         visited(e) ← True
36:     end for
37:     for all u ∈ IN_NODES(v) do
38:         if |{e|e ∈ OUT_EDGES(u), visited(e) = False}| = 0 then
39:             push u into s
40:         end if
41:     end for
42: end while
```

FIG. 23

| Algorithm 6 Find the best path in $G_s$ as the consensus sequence (cont.) |
| --- |
| 43: $v \leftarrow v_B$ |
| 44: *consensus_path* ← empty list |
| 45: while *True* do |
| 46:     append $v$ to *consensus_path* |
| 47:     if $v$ has no best score edge then |
| 48:         Break |
| 49:     else |
| 50:         $(e_{best\_out} : v \rightarrow u) \leftarrow best\_score\_edge(v)$ |
| 51:         $v \leftarrow u$ |
| 52:     end if |
| 53: end while |

FIG. 24

HIERARCHICAL GENOME ASSEMBLY METHOD USING SINGLE LONG INSERT LIBRARY

CLAIM OF PRIORITY

This application claims the benefit of priority under 35 U.S.C. § 119(e) to U.S. provisional application Ser. Nos. 61/671,554, filed Jul. 13, 2012, and 61/784,219, filed Mar. 14, 2013, both of which are incorporated herein by reference in their respective entireties.

TECHNICAL FIELD

The technology described herein generally relates to nucleic acid sequencing, and more particularly relates to methods and computer apparatus for deducing the sequence of a nucleic acid by assembling reads.

BACKGROUND

Advances in biomolecule sequence determination, in particular with respect to nucleic acid and protein samples, have revolutionized the fields of cellular and molecular biology. Facilitated by the development of automated sequencing systems, it is now possible to sequence an entire genome, for example, of a micro-organism. However, the quality of the sequence information must be carefully monitored, and may be compromised by many factors related to the biomolecule itself or the sequencing system used, including the composition of the biomolecule (e.g., base composition of a nucleic acid molecule), experimental and systematic noise, variations in observed signal strength, and differences in reaction efficiencies. As such, processes must be implemented to analyze and improve the quality of the data from such sequencing technologies.

Besides affecting overall accuracy of sequence reads generated, these factors can complicate designation of a base-call as a true variant or, alternatively, a mis-call (e.g., insertion, deletion, or mismatch error in the sequence read). For example, in a diploid organism a chromosome can have loci that differ in sequence from the homologous chromosome. It is important to be able to call whether such a locus is a true variation between the homologues, or is a sequencing error. Furthermore, a viral population in an individual can have many variations between individual viral genomes in the population, especially in highly mutable viruses such as HIV. Being able to identify different sequencing reads that have different origins (e.g., different chromosome or genome origins) is key to being able to accurately characterize a nucleic acid. For a theoretical sequencing platform that generates reads that are 100% accurate, the reads can simply be compared to one another with simple string matching algorithms. Any difference between the reads is indicative of a true variant, and therefore, a different origin. However, any real-world raw sequencing data is likely to contain errors, so a simple string matching algorithmic approach will not be sufficient in most cases.

Sequencing applications generally fall into two categories, de novo assembly and re-sequencing. Both efforts require highly-automated, accurate assembly of nucleic acid fragments into contigs. They differ from one another in that de novo assembly is performed using overlapping reads, while re-sequencing assumes knowledge of a reference sequence and maps reads to the reference. Although establishing relative read position is significantly easier for re-sequencing, the subsequent task of calling a consensus base for each aligned column in the contig or alignment is still challenging.

The standard of sequencing accuracy was set to 99.99% by the National Human Genome Research Institute (NH-GRI) in 1998. While a single base-call for each position in a template may not achieve such accuracy, with increases in coverage multiple overlapping sequencing reads for a template sequence having lower raw read accuracy can be used to determine a consensus sequence with acceptably high accuracy. Consensus calling algorithms attempt to distinguish sequencing error from variants (e.g., SNP's) using multiple "queries" for a given position. A variety of such algorithms have been developed to address changes in sequencing coverage, error profiles, and information accompanying base-calls as new sequencing systems are developed, e.g., Li, et al. (2008) *Genome Res.* 18:1851-1858; and Chen, et al. (2007), "PolyScan: An automatic indel and SNP detection approach to the analysis of human resequencing data," *Genome Res.* 17(5):659-666. Other methods and algorithms that may be used with or are otherwise related to the methods provided herein are found in G. A. Churchill, M. S. Waterman (1992) "The Accuracy of DNA Sequences: Estimating Sequence Quality," Genomics 14: 89-98; M. Stephens, et al. (2006) "Automating sequence-based detection and genotyping of SNPs from diploid samples," Nat. Genet., 38: 375-381; Li, et al (2008) "Mapping short DNA sequencing reads and calling variants using mapping quality scores," Genome Research 18(11):1851-8; and Chen, et al. (2007), Genome Research, 17(5):659-666, the disclosures of which are incorporated herein by reference in their entireties for all purposes. Additional methods and algorithms that may be used with or are otherwise related to the methods provided herein are found in U.S. patent application Ser. No. 13/468,347, filed May 10, 2012; U.S. Patent Publication Nos. 2009-0024331 and 2010-0169026, and U.S. Patent Application Publication Nos. 2011-0257889, and 2011-0256631, both published Oct. 20, 2011, all of which are incorporated by reference herein in their entireties for all purposes.

Most third party genome assemblers, e.g., Celera®Assembler®, assume that the overlap between the reads can be detected with high identity. For example, an overlap might be called when the identity in the alignment between two reads is above 94%. While it is not necessary to assemble the sequence of an entire genome using such stringent requirements, (e.g., the ALLORA assembler from Pacific Biosciences, Menlo Park, Calif., can use reads that only have 70% identity between each other), it remains preferable to construct inputs whose overlap can be detected with high identity before passing them to a third party assembler. Moreover, when there are repeats in a genome, it is also favorable to generate input that can clearly distinguish the different repeats. Finally, it is also preferable that some artifacts, e.g., chimeric reads and high quality region identification errors, due to sequencing reactions, can be filtered out before the assembly step.

Sequencing technologies that combine reads from libraries of different lengths of DNA have been developed to generate reads that can satisfy the more stringent input requirements for third party assemblers. However, most of these methods require preparation and separate sequencing of multiple DNA libraries.

Single Molecule, Real-Time (SMRT®) DNA sequencing provides a method to generate sequencing reads that are much longer than those possible with second-generation methods or even Sanger sequencing, thereby facilitating a more effective pathway towards de novo genome assemblies and genome finishing (see, e.g., Rasko, Webster et al., 2011; English, Richards, et al., 2012). For typical bacterial genome sizes (1-10 Mb), hybrid assembly approaches have been described which utilize the long SMRT® sequencing reads in conjunction with shorter reads (from SMRT® circular consensus sequencing reads or second-generation sequencing methods) for generating, for the first time, finished high-quality genome assemblies in automated workflows (Bashir, Klammer et al., 2012; Koren, Schatz et al., 2012; Ribeiro, Przybylski, et al., 2012). While these strategies have been applied successfully to a variety of microbes and also to eukaryotic organisms, the hybrid assembly principle requires the preparation of at least two different sequencing libraries and several types of sequencing runs (and sometimes several different sequencing methods). For more efficient and cost-effective genome closing, a homogenous workflow only requiring one library and sequencing method would be desirable.

The discussion of the background herein is included to explain the context of the technology. This is not to be taken as an admission that any of the material referred to was published, known, or part of the common general knowledge as at the priority date of any of the claims found appended hereto.

Throughout the description and claims of the specification the word "comprise" and variations thereof, such as "comprising" and "comprises", is not intended to exclude other additives, components, integers or steps.

SUMMARY

The instant disclosure addresses a computer-implemented method of identifying the sequence of a nucleic acid, and an apparatus for carrying out the method. In particular, the invention is directed to methods for processing raw sequence data, as might be obtained from SMRT® sequencing, or from nanopore-based measurements.

The methods provided herein are applicable not only to sequence data having few errors, but also to sequence data having relatively high rates of insertions, deletions, and/or mismatch errors.

In certain aspects, the methods are computer-implemented methods. In certain aspects, the algorithm and/or results (e.g., sequences generated) are stored on a computer-readable medium, and/or displayed on a screen or on a paper print-out. In certain aspects, the results are further analyzed, e.g., to identify genetic variants, to identify one or more origins of the sequence information, to identify genomic regions conserved between individuals or species, to determine relatedness between two individuals, to provide an individual with a diagnosis or prognosis, or to provide a health care professional with information useful for determining an appropriate therapeutic strategy for a patient.

In certain aspects, the invention provides methods for identifying a sequence of a nucleic acid. In certain embodiments, such methods comprise several steps including: forming a seed sequence dataset comprising one or more seed reads identified as reads in the set of reads having lengths greater than a predetermined threshold, e.g., 1,000 base pairs; aligning each read in the set of reads to a seed read, thereby producing a sequence alignment for each seed read that comprises a subset of the set of reads; creating a pre-assembled read for each seed read, from each sequence alignment, thereby generating a set of pre-assembled reads, one for each seed read; using a sequence assembler to assemble the set of pre-assembled reads into a contig for the nucleic acid; and determining a consensus sequence of the nucleic acid. In some embodiments, the creating a pre-assembled read for each seed read comprises: a) using the sequence alignments from the aligning to construct a sequence alignment graph; and based upon the sequence alignment graph, determining a consensus sequence for the seed read. In certain embodiments, the creating a pre-assembled read for each seed read further comprises subjecting each sequence alignment produced in the aligning to normalization prior to constructing the sequence alignment graph. For example, the normalization can comprise changing mismatches to indels and/or moving gaps to right-most equivalent positions. In certain preferred embodiments, the constructing the sequence alignment graph comprises constructing a multi-graph and merging nodes and edges in the multi-graph. The method can further comprise optimizing each pre-assembled read to produce a set of refined pre-assembled reads prior to using the sequence assembler.

In certain aspects, systems for identifying a sequence of a nucleic acid are provided. Such systems typically comprise computer memory containing computer-readable code for (a) determining a best overall matching sequence from the set of sequence reads, (b) aligning all sequence reads against the best overall matching sequence, (c) normalizing the sequence alignments, (d) constructing a sequence alignment graph, (e) determining a consensus sequence for the sequence alignment graph, (f) clustering sequence reads based on the structure of the sequence alignment graph and/or the consensus sequence, and (g) aligning the sequence reads in each resulting cluster to generate a new sequence alignment graph and/or consensus sequence for the cluster. Such systems typically further comprise computer memory containing an alignment of a set of sequence reads and other data generated by the methods of the invention, e.g., best-matching sequences, reference sequences, sets of sequence alignments, sequence alignment graphs, consensus sequences, subsets of sequence reads within clusters, and other outputs of the operations carried out by the computer-readable code encoded therein.

The invention and various specific aspects and embodiments will be better understood with reference to the following detailed descriptions and figures, in which the invention is described in terms of various specific aspects and embodiments. These are provided for purposes of clarity and should not be taken to limit the invention. The invention and aspects thereof may have applications to a variety of types of methods, devices, and systems not specifically disclosed herein.

BRIEF DESCRIPTION OF THE DRAWINGS

FIG. 7: Table 1B (a)-(d).

FIG. 9 provides illustrative examples of repeat instance 1 (a) and repeat instance 2 (b), both shown in dashed-line boxes. The repeat is 5.4 kb in length, and there is 95.4% identity between repeat instances 1 and 2.

FIG. 17: Examples of normalization of gaps in the alignment.

FIG. 19: Algorithm 1.

FIG. 20: Algorithm 2 (pseudocode).

FIG. 21: Algorithm 3 (pseudocode).

FIG. 22: Algorithm 4 (pseudocode).

FIG. 23: Algorithm 5 (consensus algorithm).

FIG. 24: Algorithm 6 (consensus algorithm).

Like reference symbols in the various drawings indicate like elements.

DETAILED DESCRIPTION

Figure 1:
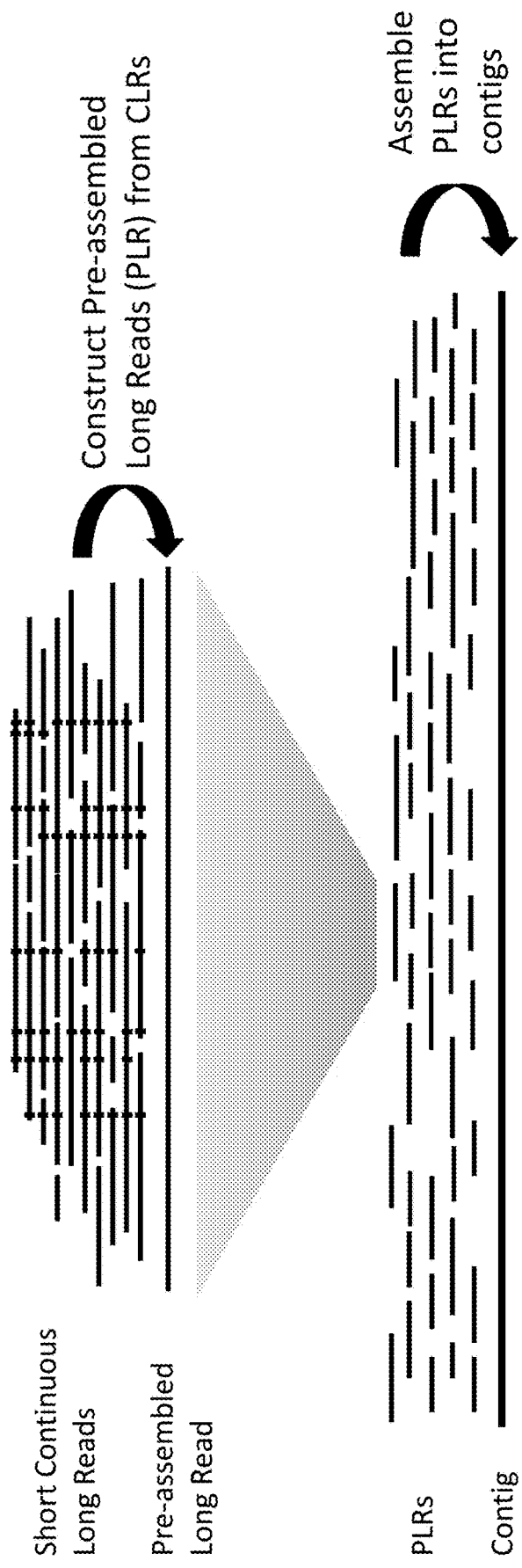
FIG. 1 shows a schematic of the Hierarchical Genome Assembly process (HGAP), as described herein, using long-insert size DNA shotgun template libraries with SMRT® sequencing. The tick marks on the CLRs indicate positions of sequence variants in the sequence reads. The longest reads are selected as "seed" reads, to which all other continuous long reads (CLRs) are mapped. A pre-assembly is performed that converts the seed reads into pre-assembled long reads (PLRs) which are used for the genome assembly, followed by a final consensus calling step (not shown).

The instant technology is directed to methods, computer systems, and computer readable media, deployed towards identifying nucleic acid sequences.

Definitions and Background Technology

Various embodiments and components of the present invention employ signal and data analysis techniques that are familiar in a number of technical fields. For clarity of description, details of known analysis techniques are not provided herein. Such techniques are described in a number of reference works, such as: R. B. Ash. Real Analysis and Probability, Academic Press, New York, (1972); D. T. Bertsekas and J. N. Tsitsiklis, Introduction to Probability, (2002); K. L. Chung, Markov Chains with Stationary Transition Probabilities, (1967); W. B. Davenport and W. L Root. An Introduction to the Theory of Random Signals and Noise. McGraw-Hill, New York, (1958); S. M. Kay, Fundamentals of Statistical Processing, Vols. 1-2, (Hardcover—1998); Monsoon H. Hayes, Statistical Digital Signal Processing and Modeling, (1996); Introduction to Statistical Signal Processing by R. M. Gray and L. D. Davisson; Modern Spectral Estimation: Theory and Application/Book and Disk (Prentice-Hall Signal Processing Series) by Steven M. Kay (Hardcover—January 1988); Modern Spectral Estimation: Theory and Application by Steven M. Kay (Paperback—March 1999); Spectral Analysis and Filter Theory in Applied Geophysics by Burkhard Buttkus (Hardcover—May 11, 2000); Spectral Analysis for Physical Applications by Donald B. Percival and Andrew T. Walden (Paperback—Jun. 25, 1993); Astronomical Image and Data Analysis (Astronomy and Astrophysics Library) by J. L. Starck and F. Murtagh (Hardcover—Sep. 25, 2006); Spectral Techniques In Proteomics by Daniel S. Sem (Hardcover—Mar. 30, 2007); Exploration and Analysis of DNA Microarray and Protein Array Data (Wiley Series in Probability and Statistics) by Dhammika Amaratunga and Javier Cabrera (Hardcover—Oct. 21, 2003).

The present invention is generally directed to powerful and flexible methods and systems for sequence determination from data generated by sequencing nucleic acids. Technologies and methods for biomolecule sequence determination do not always produce sequence data that is perfect. For example, it is often the case that DNA sequencing data does not unambiguously identify every base with 100% accuracy, and this is particularly true when the sequencing data is generated from a single pass, or "read." In preferred embodiments, the consensus sequencing accuracy achieved using the methods herein is at least 95%, 96%, 97%, 98%, 99%, 99.5%, 99.9%, or 99.99%. Furthermore, certain preferred embodiments use only sequence read data, to achieve highly accurate consensus sequences. In some embodiments, the accuracy of the sequence read data used is only about 70%, 75%, or 80%. In more preferred embodiments, the accuracy of the sequence read data is about 85%, 90%, or 95%. In certain aspects, the methods provided herein allow determination of highly accurate consensus sequences, as described above, from sequence read data having an accuracy less than 95%, 90%, 85%, 80%, 75%, or 70%.

Sequences from various kinds of biomolecules, e.g., polynucleotides and polypeptides, may be analyzed by the methods presented herein. The biomolecule may be naturally-occurring or synthetic, and may comprise chemically and/or naturally modified units, e.g., acetylated amino acids, methylated nucleotides, etc. Methods for detecting such modified units are provided, e.g., in U.S. Patent Application Publication numbers 2010-0221716, published Sep. 2, 2010; and U.S. Patent Application Publication No. 2011-0183320, published Jul. 28, 2011, which are incorporated herein by reference in their entireties for all purposes. In certain embodiments, the biomolecule is a nucleic acid, such as DNA, RNA, cDNA, or derivatives thereof. In some preferred embodiments, the biomolecule is a genomic DNA molecule. The biomolecule may be derived from any living, or once living, organism, including but not limited to prokaryote, eukaryote, plant, animal, and virus, as well as synthetic and/or recombinant biomolecules. Furthermore, each read may also comprise information in addition to sequence data (e.g., base-calls), such as estimations of per-position accuracy, features of underlying sequencing technology output e.g., trace characteristics (integrated counts per peak, shape/height/width of peaks, distance to neighboring peaks, characteristics of neighboring peaks), signal-to-noise ratios, power-to-noise ratio, background metrics, signal strength, reaction kinetics, and the like. These metrics and trace characteristics can also be used in determination of the base sequence of a nucleic acid, e.g., in addition to fluorescent spectral measurements. More details and methods of analyzing such metrics and trace characteristics are provided in U.S. Pat. No. 8,182,993, which is incorporated herein by reference in its entirety for all purposes.

Sequence reads are provided using essentially any technology capable of generating sequence data from biomolecules, including but not limited to: Maxam-Gilbert sequencing, chain-termination methods, PCR-based methods, hybridization-based methods, ligase-based methods, microscopy-based techniques, sequencing-by-synthesis such as pyrosequencing, SMRT® sequencing, SOLiD™ sequencing (Life Technologies), semiconductor sequencing (Ion Torrent Systems), tSMS™ sequencing (Helicos BioSciences), Illumina® sequencing (Illumina, Inc.), nanopore-based methods (e.g., BASE™, GridION™, MinION™), which are further described in U.S. Pat. Nos. 8,324,914 and 5,795,782; and U.S. Patent Publication Nos. 2010/0025249, 2010/0148126, and 2010/0174625, all of which are incorporated herein by reference in their entireties for all purposes. In certain preferred embodiments, the sequence reads are long sequence reads, e.g., at least about 0.5, 1, 2, 3, 5, 10, 15, or 20 kb in length, and in some embodiments averaging about 0.5, 1, 2, 3, 5, 10, 15, or 20 kb in length. In preferred embodiments, the sequence reads are generated using a single-molecule sequencing technology such that each read is derived from sequencing of a single template molecule. Single-molecule sequencing methods are known in the art, and preferred methods are provided in U.S. Pat. Nos. 7,315,019, 7,476,503, 7,056,661, 8,153,375, and 8,143,030; U.S. Application Publication Nos. 2010-0221716, published Sep. 2, 2010, and 2010-0311061, published Dec. 9, 2010, all of which are incorporated herein by reference in their entirety for all purposes. In certain preferred embodiments, the technology used comprises a zero-mode waveguide (ZMW). The fabrication and application of ZMWs in biochemical analyses, and methods for calling bases in sequencing applications performed within ZMWs, e.g., sequencing-by-incorporation methods, are described, e.g., in U.S. Pat. Nos. 6,917,726, 7,013,054, 7,056,661, 7,170,050, 7,181,122, and 7,292,742, U.S. Patent Application Publication No. 2009-0024331, and U.S. Patent Application Publication no. 2011-0256631 (published Oct. 20, 2011), as well as in Eid, et al. (Science, 323:133-138 (2009)), and Korlach, et al. (*Methods Enzymol.* 472:431-455 (2010)) the full disclosures of which are incorporated herein by reference in their entirety for all purposes. In preferred embodiments, the sequence reads are provided in a FASTA file.

In certain embodiments, the sequence information analyzed comprises replicate sequence information. For example, replicate sequence reads may be generated by repeatedly sequencing the same molecules, sequencing templates comprising multiple copies of a target sequence, sequencing multiple individual biomolecules all of which contain the sequence of interest or "target" sequence, or a combination of such approaches. Replicate sequence reads need not begin and end at the same position in a biomolecule sequence, as long as they contain at least a portion of the target sequence. For example, in certain sequence-by-synthesis applications, a circular template can be used to generate replicate sequence reads of a target sequence by allowing a polymerase to synthesize a linear concatemer by continuously generating a nascent strand from multiple passes around the template molecule and monitoring incorporation of nucleotides into the nascent strand. Examples of methods of generating replicate sequence information from a single molecule are provided, e.g., in U.S. Pat. No. 7,476,503; U.S. Patent Application Publication No. 2009-0298075; U.S. Patent Application Publication No. 2010-0075309; U.S. Patent Application Publication No. 2010-0075327; U.S. Patent Application Publication No. 2010-0081143, U.S. Provisional Patent Application No. 61/094,837, filed Sep. 5, 2008; and U.S. Provisional Patent Application No. 61/099,696, filed Sep. 24, 2008, all of which are incorporated herein by reference in their entireties for all purposes.

For ease of discussion, various aspects of the invention will be described with regards to analysis of polynucleotide sequences, but it is understood that the methods and systems provided herein are not limited to use with polynucleotide sequence data and may be used to determine consensus sequences for other types of sequence data, e.g., from polypeptide sequencing reactions.

Overview of Method

In hybrid assembly strategies involving SMRT® sequencing and second generation, short read sequencing technologies, it has been observed that the process of assembling the sequence can fail in regions where the second generation sequencing data does not provide sufficient coverage (due to the GC bias, AT bias or other sequence context biases inherent in those technologies, as mentioned above). For those regions, the establishment of a multi-molecule consensus sequencing using only SMRT® sequencing reads mapping to this region can be used to cross these junctions and connect the contigs.

Because of the presence of long reads, lack of bias with respect to genomic sequence content, and high consensus accuracy due to the random nature of errors in SMRT® sequencing, this principle can be adapted genome-wide for the generation of finished genomes using just long-insert library SMRT® sequencing. The technology described herein, comprises a non-hybrid, hierarchical genome assembly process (HGAP) which implements this paradigm in a fully automated workflow. It can be used to demonstrate the de novo construction of several microbial genomes into finished, single-contig assemblies. Part of this workflow is a consensus algorithm which takes advantage of SMRT® sequencing quality values to result in highly accurate genome sequence results. The performance of the assembly method was evaluated on several bacterial genomes for which Sanger sequencing was used to generate reference sequences, to find that the de novo assembly according to the methods herein is co-linear with these references, and is >99.999% (>QV50) concordant.

In order to simplify genome assembly workflow, it is preferable to make a single, long-insert library and then convert the long reads from SMRT® sequencing to some input that satisfies the requirement for third party assemblers. The method described herein comprises hierarchical assembling steps to generate pre-assembled read sequences that can be further assembled by third party assemblers to construct the final genome assembly.

In summary, the principle and general workflow of HGAP are shown schematically in FIG. 1. It comprises several steps: (1) Select the longer sequencing reads as the seeding sequence data set. (2) Use seeding sequences as a reference to recruit reads for a pre-assembly step. The pre-assembled long reads (PLRs) are constructed through a consensus procedure. (3) Use assemblers that are capable of assembling long sequence reads to assemble the PLRs. (4) Generate the final genome sequence which uses all initial read data to generate the best consensus that represents the genome. Optionally, the contigs from step (3) can be connected further using sequence assembly tools such as minimus2 or similar, to further improve continuity of the assembly and to remove any spurious contigs that may arise due to assembly errors and/or sequencing errors (Sommer, Delcher, et al., (2007); Treangen, Sommer et al., (2011)). Details about each of these analysis steps are described hereinbelow.

(1) The hierarchical genome assembly process starts with using the longer reads to put other reads together, in a similar manner to a sequence assembly process. The method utilizes certain special features of SMRT® sequencing wherein the read length distribution is not a constant but an exponential one. It is understood that, for a typical sequencing run with a long inserted library, the probability P(l) of obtaining a read with read length l, is proportional to exp(−l/L), where L is the average read length. In other words, SMRT® sequencing produces not only shorter fragments but also a number of longer ones. An alignment algorithm (e.g., as implemented in a program such as BLASR, from Pacific Biosciences, Menlo Park, Calif.) can be used to align all the reads to a longer read, thereby creating a mini-assembly for each long read.

Once the reads are aligned to various long reads, the alignments are used to generate a consensus sequence representing the mini-assembly using all the reads that align to the long read. In a preferred embodiment, the consensus algorithm developed for HLA typing, as described hereinbelow, can be used to generate the consensus.

Figure 2:
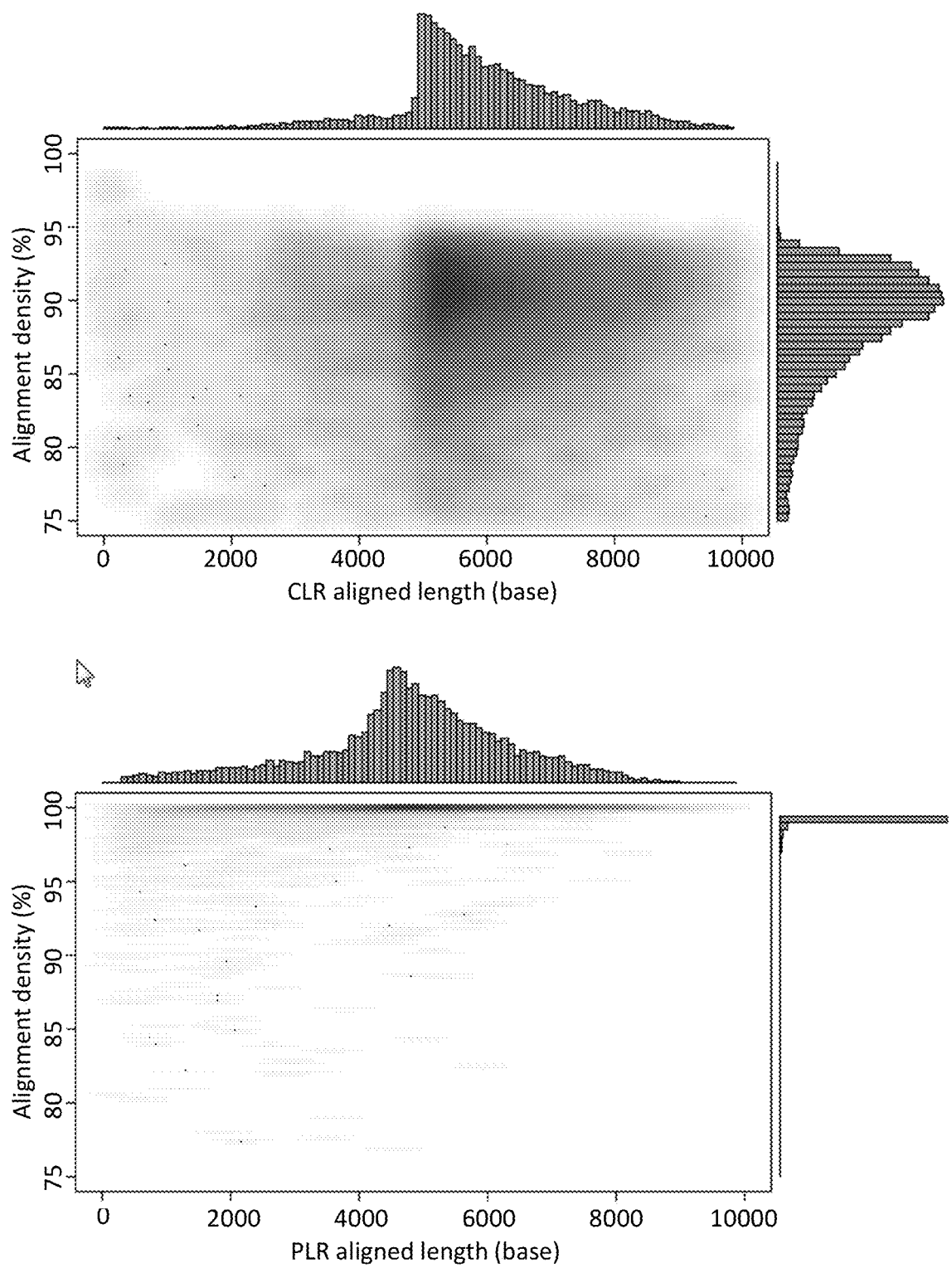
FIG. 2: (a) Read length and accuracy distributions of CLRs against a previously determined Sanger *E. coli* MG1655 reference; (b) Read length and accuracy distributions of PLRs against the previously determined reference; (c) Additional information for the data represented by the column on the right side of the graph in FIG. 2(b), showing a more fine breakdown of the % alignment identity.
Figure 2:
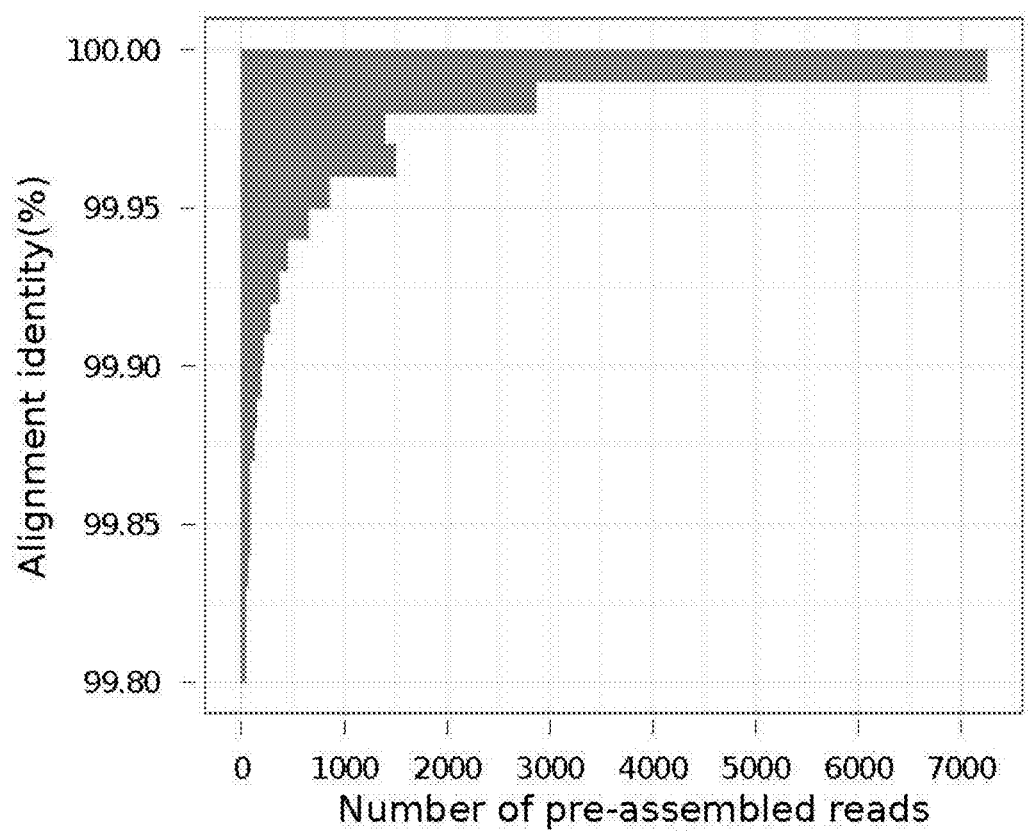

(2) In the previous step, if there are gaps in the alignment mapping, only those chunks that have mapping coverage above a minimum threshold (e.g., four- or higher-fold coverage) in the consensus are output. This process effectively removes potential chimera or other artifacts in the original long read. Namely, the potential for mis-assembly is removed by checking the consistency of the original inputs from this mini-assembly step. As shown in the two plots in FIG. 2, in contrast to the long read used for constructing the mini-assemblies, the pre-assembled long reads (PLR) have better accuracy. Such longer and accurate PLRs make a better final assembly according to the Lander-Waterman theory of genome assembly statistics (Lander, et al. (1988) Genomics 2(3):231-239, which is incorporated herein by reference in its entirety for all purposes).

(3) The pre-assembled reads will have accuracy typically higher than 98% or 99%. Since they can provide reliable information for overlap detection for third party assemblers, a third-party assembler, e.g., the Celera®Assembler®, can be used to further assemble the pre-assembled reads into longer contigs that are close to the final representation of the sequence of the biomolecule, or nucleic acid in question.

(4) Finally, all the original reads are aligned back to the contigs, and then CCS consensus algorithms (e.g., "Quiver", as described in U.S. Pat. No. 8,370,079, incorporated by reference herein), but used for multiple molecule consensus, can be applied to further improve the assembly quality by removing further errors via this independent consensus step.

The foregoing steps are now described in further detail.

Mapping

In order to utilize all continuous long reads (CLR's) from raw sequencing data, for example as generated by the PacBio® RS®, the longer portion of the raw reads, using a pre-specified length cutoff, $l_{cutoff}$, are extracted to provide the "seeds" for constructing pre-assemblies. These seed reads are used to recruit other reads as a scaffold. It is desirable to achieve about 15-20× genome coverage of such seed sequences so that a sufficient amount of coverage of pre-assembled reads will be generated for the subsequent assembly. The pre-assembled reads are constructed by aligning all reads to each of the seed reads. Each read is mapped to multiple targeted seed reads using the program BLASR (Chaisson and Tesler 2012). The number of read hits mapping to the seed sequences is controlled by the "-bestn" parameter when calling the program BLASR for mapping. Such number should be smaller than the total coverage of the seed sequences on the genome. If the "-bestn" number is too high, it is likely that reads from similar repeats will be mapped to each other, which could result in consensus errors. Conversely, if the chosen "-bestn" number is too low, the quality of the pre-assembly consensus may be decreased. The optimal choice might also depend on DNA fragment library construction, which can affect the subread length distribution. A preferred value of "-bestn" is 12 reads to map to the seed reads. Further study will allow a reasonable choice for optimized results.

Pre-Assembly

From this initial mapping process to the seed sequences, a mini-assembly of those reads that are mapped to them is performed. Since the seed sequences are long, such mini-assembly can be done simply by an alignment-and-consensus step to construct single "pre-assembled long reads" (PLRs) for each of the seed reads. In general, an algorithm is needed that can generate good consensus by eliminating insertion and missing errors in the raw sequences efficiently for this pre-assembly step. There are multiple approaches that can achieve such goal. One suitable method of accomplishing pre-assembly is described in U.S. provisional patent application Ser. No. 61/671,554, filed Jul. 13, 2012, which is incorporated herein by reference. In a preferred embodiment, an algorithm referred to as "PBDAG-Con" (see pacbiodevnet.com/HGAP) is used for generating the PLRs. This algorithm is based on encoding multiple sequence alignments with a directed acyclic graph to find a best path for best consensus. Using a graph to represent multiple sequence alignments (MSAs) is helpful to effectively remove random insertion and missing errors for generating the consensus from it. For example, a long stretch of random insertions is typically an isolated path in the graph that can be eliminated easily when looking for the optimized path as the consensus. The principle of the preassembly step is illustrated in FIG. 1. The full description of the algorithm used in PBDAG-Con is presented in Appendix 1.

Figure 3:
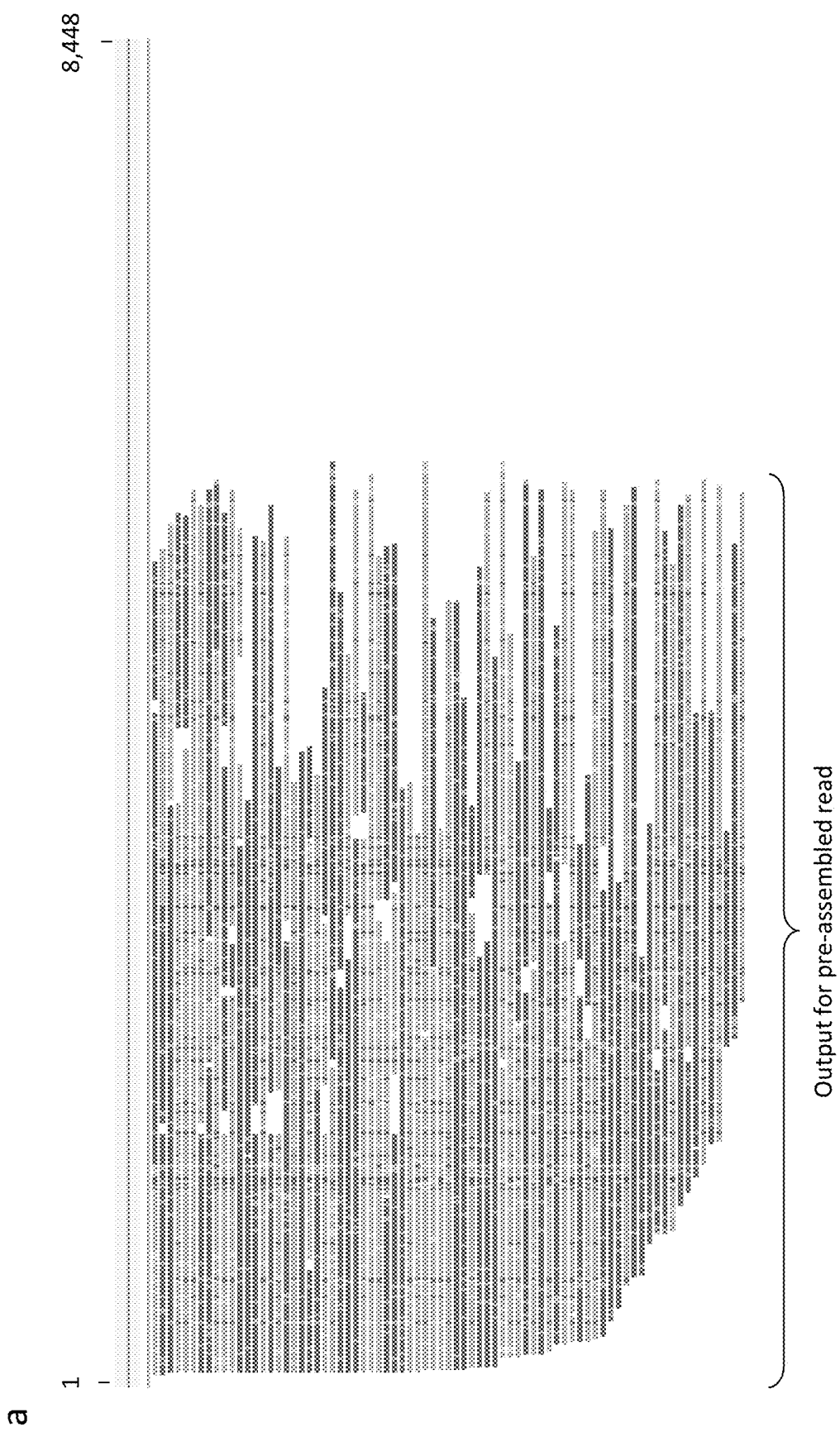
FIG. 3: Examples for detection and removal of (a) spurious reads and (b) chimeric DNA molecules during the pre-assembly step of the E. coli MG1655 HGAP assembly. The darker grey and lighter grey are indicative of the two complementary strands, e.g., the forward and reverse strands of the double-stranded template. The tick marks are indicative of variant loci in the sequence reads.
Figure 3:
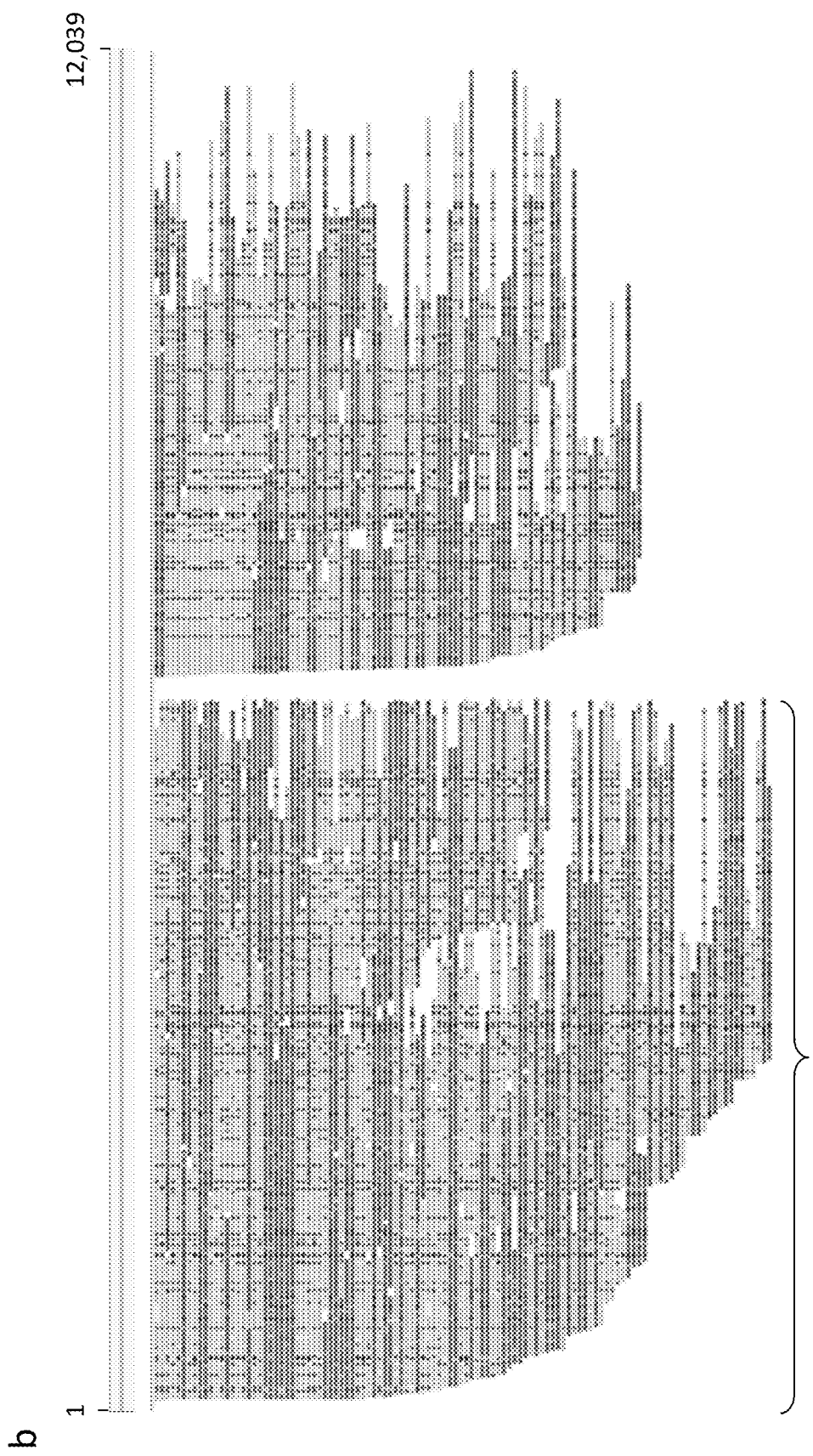

Certain sequencing artifacts are removed during this pre-assembly process, e.g., spurious low quality sequences and/or chimeric reads (FIG. 3). Generally, this involves a few steps of trimming the alignment hits and removing the regions that do not have a sufficient number or quality of CLRs mapped to the seed reads (FIG. 2a). Long chimeric sequences can easily confuse an assembly during the stage of constructing layouts, and they are typically removed as the first step within a genome assembler (Huang 1996; Kelley, Schatz et al. 2010). The pre-assembly step described herein relies on consistent information contained in all CLRs. As chimeric reads are mostly likely generated randomly during the sample preparation step, the chimera junction in a CLR should be random, i.e., a chimeric seed read would have zero or low coverage through the chimeric junction when other CLRs are mapped to it, shown by example in FIG. 2b. Through this process, the construction of a PLR that contains the whole chimeric sequence is avoided. By detecting and removing such artifacts early, i.e., during the pre-assembly step, the best PLRs without artifacts are sent to an assembler.

One can think of the pre-assembly process to combine the CLRs into a PLR as an assembly of the shorter CLRs, using the long seeds to provide the overlap and layout information. The PLR can be seen as the "contig" output of the traditional overlay-layout-consensus assembler. Therefore, existing modularized infrastructure for genome assemblies, e.g., AMOS (Treangen, Sommer et al. 2011), can be utilized for this pre-assembly step to assemble the shorter CLRs to generate PLRs for subsequent full genome assembly.

Assembly

After the pre-assembly step, the PLRs typically have read accuracies above 98% or 99% (descriptions of the PLR accuracy are presented in the Examples section hereinbelow). Therefore, the PLRs can be easily fed into an assembler that can accommodate long read inputs. Typically, assemblers that use the overlap-layout-consensus (OLC) strategy are better for assembling such long PLRs. Both Celera® Assembler (Myers, Sutton et al., 2000) and MIRA (at Internet web-site: sourceforge.net/projects/mira-assembler/) can be used for the assembly process. For both assemblers, preferred parameters and configurations are those originally designed for Sanger sequencing reads, as this gives good PLR accuracy. For assemblers that require quality values as input, a uniform phred score of QV 24 can be assigned for all bases in the PLRs. Assigning such an ad hoc QV does not affect the assembly results as the quality of PLRs are generally uniform since SMRT® sequencing does not show any quality fluctuation through the reads (Koren, Schatz et al. 2012). In addition, the assembler is only used to generate the genome contiguity—the Quiver consensus algorithm is used to determine the final genome sequence.

In alternative embodiments, the assembly step is performed using a process called "Consistent Long-read Evidence AppRoach/AssembleR" (CLEAR). This process comprises a layout program that processes ambiguous overlapped reads in a defined manner. In preferred embodiments, a "conservative greedy" algorithm strategy is central to this assembly process. Optionally, all ambiguous overlapped reads are excluded from unitig construction as they increase the likelihood of misassemblies, which can be difficult to correct at a later stage.

It has been recognized that as the read length gets longer, the percentage of reads that can be unambiguously overlapped increases. By examining the overlap data, the reads can be classified into two groups by whether (1) the overlapping alignment between two reads indicates that there might be some unique-to-repeat or repeat-to-repeat junctions within the reads and there are no "unique" parts at the ends of the reads; or (2) the overlapping alignment between two reads indicates they are totally "compatible" with each other. The reads that cannot be overlapped unambiguously are termed "split reads." For a related discussion, see Myers, E. W. (2005) "The fragment assembly string graph," Bioinformatics 21(2):ii79-ii85, which is incorporated herein by reference in its entirety for all purposes. Various alignment algorithms can be used to generate the overlap data used to classify each read into one of the two groups. In particularly preferred embodiments, the BLASR alignment algorithm is used. The BLASR alignment method is described at length in U.S. Patent Application Publication No. 2012/0330566, incorporated herein by reference in its entirety for all purposes.

Figure 15:
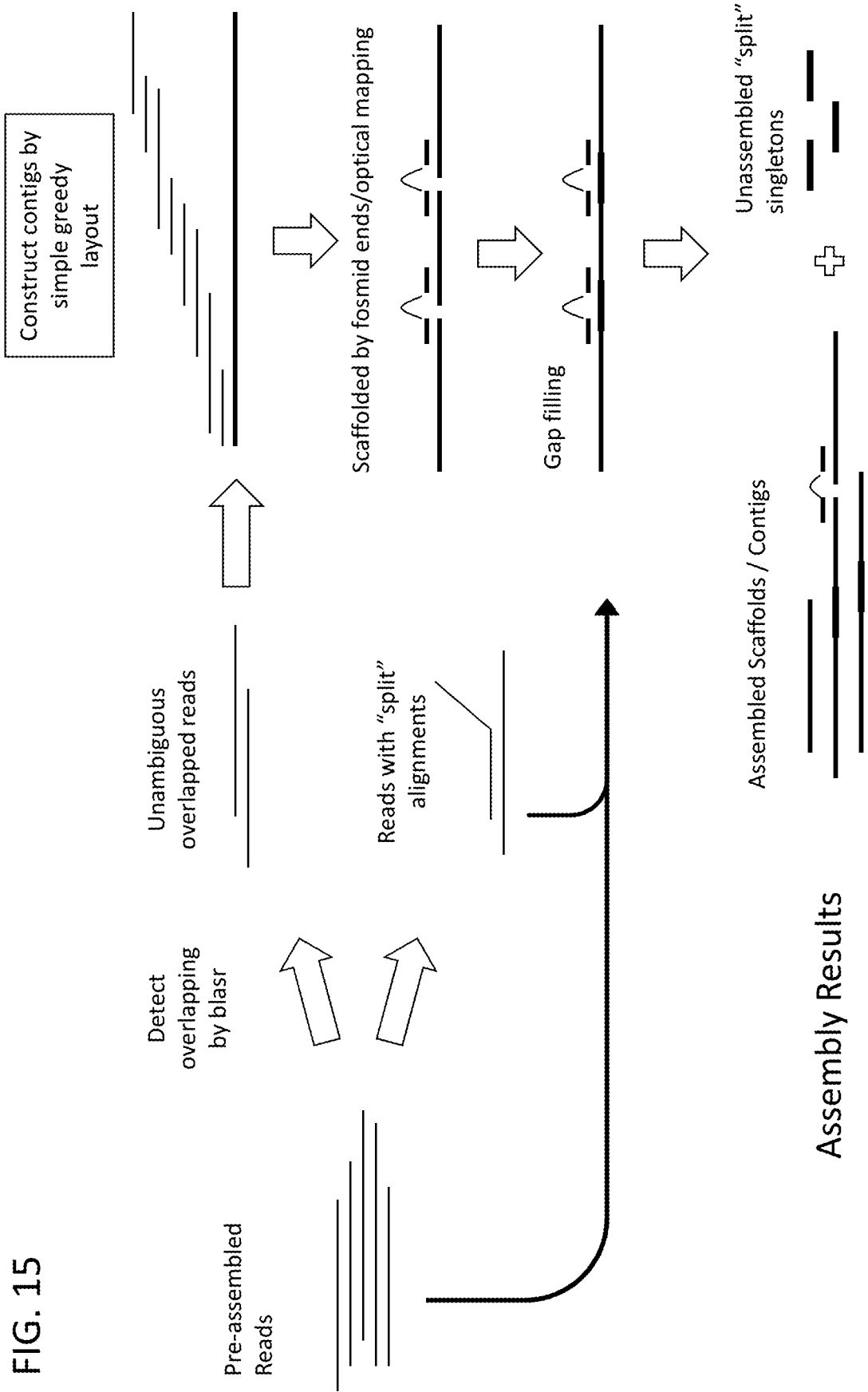
FIG. 15: Greedy algorithmic approach

In principle, one can unambiguously construct one or more contigs comprising those reads that satisfy condition (2), e.g., using a simple, greedy algorithmic approach, e.g., as illustrated in FIG. 15. It is likely that if the read lengths are longer than most of the repeats in the genome, the majority of the reads can be unambiguously assembled with a simple layout algorithm. Once the long contigs from the unambiguously overlapped reads (condition (2)) are assembled into contigs, the information from the "split reads" (condition (1)) can be incorporated to add fold coverage, infer the relationship between the contigs and some of the local repeat structure (e.g., scaffold the contigs), and otherwise develop and improve the contigs. If other information is available, e.g., fosmid ends or optical mapping, that information can also be used to facilitate unambiguous placement of the split reads on the scaffolds. For example, where the additional information spans a gap in the alignment, the contigs that are on either side of the gap can be identified and the resulting scaffold will reflect this arrangement. Gap filling between the two contigs based on the nucleotide sequence in the gap region of the split read or other sequence information described above will close the gap, thereby combining two contigs to construct one longer contig. Those split reads that cannot be mapped to the contigs, e.g., "singletons," remain unassembled.

Sometimes an assembler will generate contigs that can be further connected using, for example, minimus2 (Sommer, Delcher et al. 2007). One should generally use caution and examine the result of this post-assembly step to ensure that contigs got combined properly, and that no valid contigs got dismissed. Sometimes contigs were generated that are supported by only a very small number of reads. A re-mapping process comparing the reads to these contigs can also be used to remove such artifacts from the assemblers used. In addition, the assembler will often generate overlapping ends on circular genomes which can be trimmed manually at the very end.

Final Consensus

Upon obtaining the final result from the long read assembler, the best consensus sequence for the final genome sequence result is generated. This can be achieved with the multi-read consensus algorithm, called Quiver. The Quiver algorithm is designed to take advantage of the full information from the raw pulse and base call information that is generated during SMRT® sequencing. During the signal processing which converts the raw fluorescence pulses from a nucleotide incorporation event (Eid, Fehr et al. 2009; Korlach, Bjornson et al. 2010) into base calls, a hidden Markov model has been developed that informs about the probabilities that these events corresponded to true incorporations, missing bases or spurious base calls. The model is therefore specific to a particular SMRT® sequencing chemistry and requires a training step. Quiver takes this QV-aware model of SMRT® sequencing errors into account and uses a greedy algorithm to maximize the likelihood that the CLRs are generated from the consensus sequence it is constructing.

The SMRT® sequencing reads and the initial de novo assembly are the inputs to Quiver; the new consensus sequence and a table of corrected variants to the initial reference are its output. The algorithm first uses reference-based alignment to map the reads to their corresponding locations in an assembly, but then discards the assembly sequence and does not use it in computing the new consensus, thereby avoiding potential artifacts caused by reference bias where consensus bases have a tendency to agree with the reference (Carneiro, Russ et al., 2012). Quiver then uses a fast heuristic algorithm (Partial Order Alignment (Lee, Grasso et al., 2002)) to generate an initial, approximate consensus. Thereafter, single-base changes are applied which increase the likelihood that the underlying reads support this new template sequence. The consensus is thus repeatedly improved until the likelihood cannot be increased any further.

A full description of the Quiver algorithm is presented in Appendix 2.

Although primarily described for use in further improving the accuracy of de novo assemblies, the Quiver algorithm is also useful for re-sequencing applications in which a reference sequence is known for a region from which sequence read data has been generated. In such embodiments, there is no need for the pre-assembly or assembly steps. Instead, a pairwise aligner is used to align the sequence reads to the reference sequence. A preferred pairwise aligner is the BLASR algorithm, but essentially any pairwise aligner could be used. The resulting alignment is input to the Quiver algorithm, much in the same way as the output from the Assembly step is input in the de novo consensus sequence method. Quiver performs a final consensus determination, essentially as described hereinabove for de novo consensus sequence determination, using a QV-aware hidden Markov model and greedy algorithm to maximize the likelihood that the sequencing reads are generated from the consensus sequence it is constructing. The consensus is repeatedly improved until the likelihood cannot be increased any further, and the consensus sequence having the highest likelihood is the output of the algorithm, and is identified as the consensus sequence of the nucleic acid that was sequenced.

Computer Implementation

In preferred embodiments, the methods provided herein are computer-implemented methods, wherein at least one or more steps of the method are carried out by a processor executing instructions encoded in a computer program. In some embodiments, the methods provided herein are implemented in a computer program stored on computer-readable media, such as the hard drive of a computer, or portable storage media. For example, a computer program for determining a nucleic acid sequence can include one or more of the following: code for aligning sequence reads, code for normalizing sequence alignments, code for constructing sequence alignment graphs, code for clustering sequence reads, code for generating consensus sequences.

Furthermore, the functional aspects of the invention that are implemented on a computer or other logic processing systems or circuits, as will be understood to one of skill in the art, may be implemented or accomplished using any appropriate implementation environment or programming language, such as C, C++, Cobol, Pascal, Java, Java-script, HTML, XML, dHTML, assembly or machine code programming, RTL, etc.

In some embodiments, a system (e.g., a data processing system) that determines nucleic acid sequences includes a processor, a computer-readable medium operatively coupled to the processor for storing memory, wherein the memory has instructions for execution by the processor, the instructions including one or more of the following: instructions for receiving input of sequence reads (and, optionally, reference sequence information), instructions for aligning sequence reads, instructions for normalizing sequence alignments, instructions for constructing sequence alignment graphs, instructions for clustering sequence reads, instructions that generate consensus sequences, instructions that compute/store information related to various steps of the method (e.g., quality scores, error rates, metrics related to sequence similarities/concordance, etc.), and instructions that record the results of the method.

In certain embodiments, various steps of the method utilize information and/or programs, and generate results that are stored on computer-readable media, e.g., a hard drive, auxiliary memory, external memory, server, database, or a portable memory device such as a CD-R, DVD, ZIP disk, flash memory card. For example, information used for and results generated by the methods that can be stored on computer-readable media include but are not limited to sequence information (e.g., sequence reads), best-match sequences, sequence alignments, normalized sequence alignments, sequence alignment graphs, sequence read clusters, newly generated consensus sequences, quality information, technology information, and homologous or reference sequence information.

In some aspects, the invention includes an article of manufacture for determining a nucleic acid sequence, the article including a machine-readable medium containing one or more programs which, when executed, implement the steps of the invention as described herein.

Figure 4:
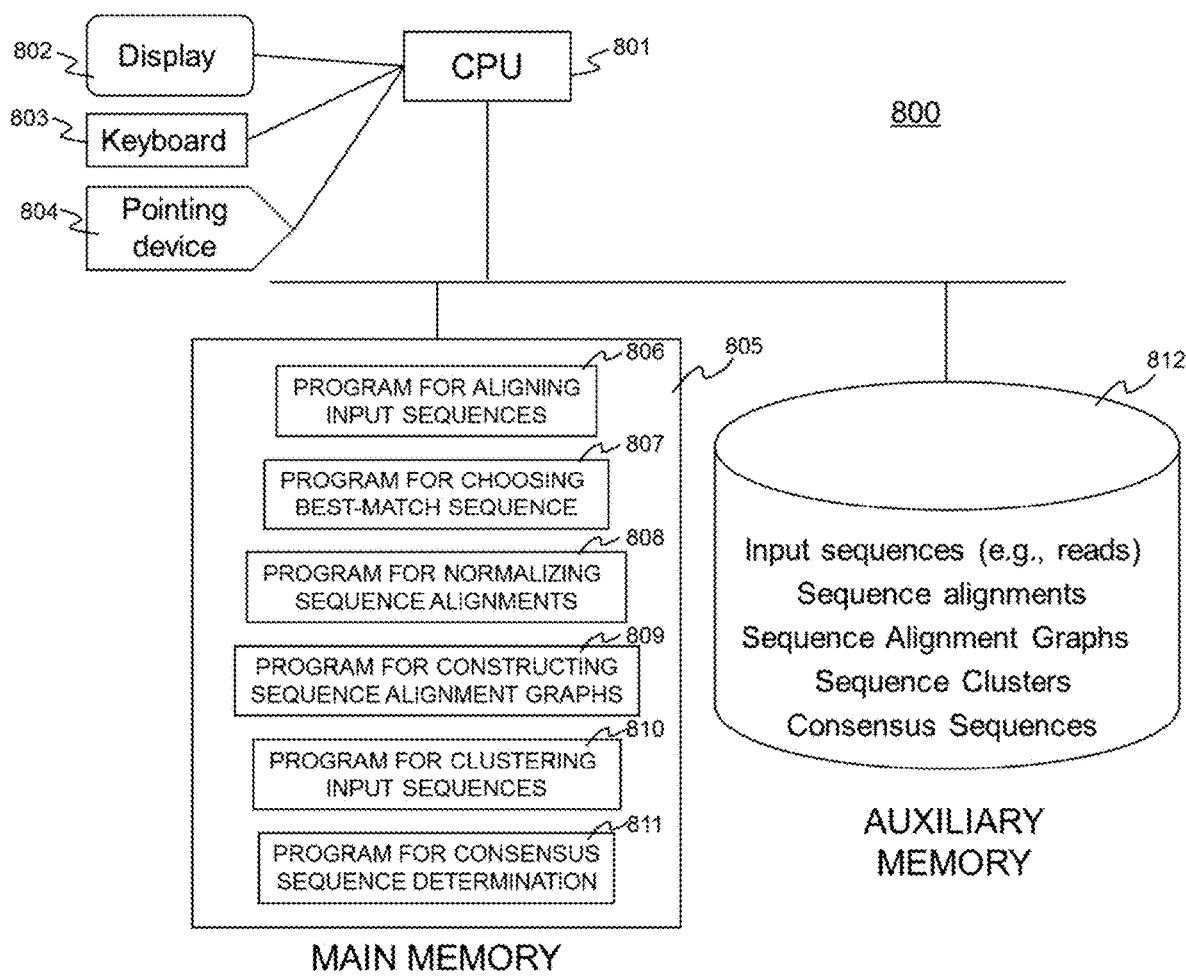
FIG. 4: shows a block diagram of a representative example of a configuration of a computer device for genetic analysis, in which various aspects of the invention may be embodied.

FIG. 4 is a block diagram showing a representative example of a configuration of a device for analysis of nucleic acid sequence data, e.g., for determining a consensus sequence, in which various aspects of the invention may be embodied. As will be understood to practitioners in the art from the teachings provided herein, the invention can be implemented in hardware and/or software. In some embodiments of the invention, different aspects of the invention can be implemented in either client-side logic or server-side logic. As will be understood by one skilled in the art, the invention or components thereof may be embodied in a fixed media program component containing logic instructions and/or data that when loaded into an appropriately configured computing device cause that device to perform according to the invention. As will be understood by one skilled in the art, a fixed media containing logic instructions may be delivered to a viewer on a fixed media for physically loading into a viewer's computer or a fixed media containing logic instructions may reside on a remote server that a viewer accesses through a communication medium in order to download a program component.

FIG. 4 shows a computer apparatus 800 that may be understood as a logical system that can read information (e.g., instructions and/or data) from auxiliary memory 812, which may reside within the device or may be connected to the device via, e.g., a network port or external drive. Auxiliary memory 812 may reside on any type of memory storage device (e.g., a server or media such as a CD or floppy drive), and may optionally comprise multiple auxiliary memory devices, e.g., for separate storage of input sequences, results of MSA, results of CSD, and/or other information. Device 800 can thereafter use that information to direct server or client logic, as understood in the art, to embody aspects of the invention.

One type of logical apparatus that may embody the invention is a computer system as illustrated in FIG. 4, containing a CPU 801 for performing calculations, a display 802 for displaying an interface, a keyboard 803, and a pointing device 804, and further comprises a main memory 805 storing various programs and a storage device 812 that can store the input sequences (e.g., sequence reads, reference sequences, etc.), results of sequence alignments, sequence alignment graphs, sequence read clusters, and consensus sequences determined by the methods herein. The device is not limited to a personal computer, but can be any apparatus for interacting with a remote data application, and could include such devices as a digitally enabled television, cell phone, personal digital assistant, etc. Information residing in the main memory 805 and the auxiliary memory 812 may be used to program such a system and may represent a disk-type optical or magnetic media, magnetic tape, solid state dynamic or static memory, etc. In specific embodiments, the invention may be embodied in whole or in part as software recorded on this fixed media. The various programs stored on the main memory can include a program 806 to align the input sequences, a program 807 to choose best-match sequences from the input sequences based on the alignment, a program 808 to normalize sequence alignments, a program 809 to construct sequence alignment graphs, a program 810 to cluster input sequences, and a program 811 to generate consensus sequences. The lines connecting CPU 801, main memory 805, and auxiliary memory 812 may represent any type of communication connection.

After input sequences and parameters required for the method of the present invention are specified by the display 802 (also referred to as a "screen" or "monitor"), the keyboard 803, and/or the pointing device 804, the CPU 801 executes the program stored in the main memory 805 and the sequence alignments, best-match selections, alignment normalizations, sequence alignment graph constructing, sequence clustering, and consensus sequence determination are performed according to the methods of the present invention. The input sequences are read from the storage device 812. The output results of the programs on storage device 805 can be stored into the storage device 812. During the process of alignments, best-match selections, normalizations, sequence alignment graph constructions, clusterings, and consensus sequence determinations by the method of the present invention, the progress of this processing can be displayed on the display 802. After completing this processing, the result of the processing can be also displayed on the display 802, saved to an additional storage device (e.g., ZIP disk, CD-R, DVD, floppy disk, flash memory card, etc.), or displayed and/or saved in hard copy (e.g., on paper). The result of the processing may be stored or displayed in whole or in part, as determined by the practitioner. These results may further comprise quality information, technology information (e.g., peak characteristics, expected error rates), alternate (e.g., second or third best) consensus sequences, confidence metrics, etc., as described in greater detail above.

EXAMPLES

Figure 5:
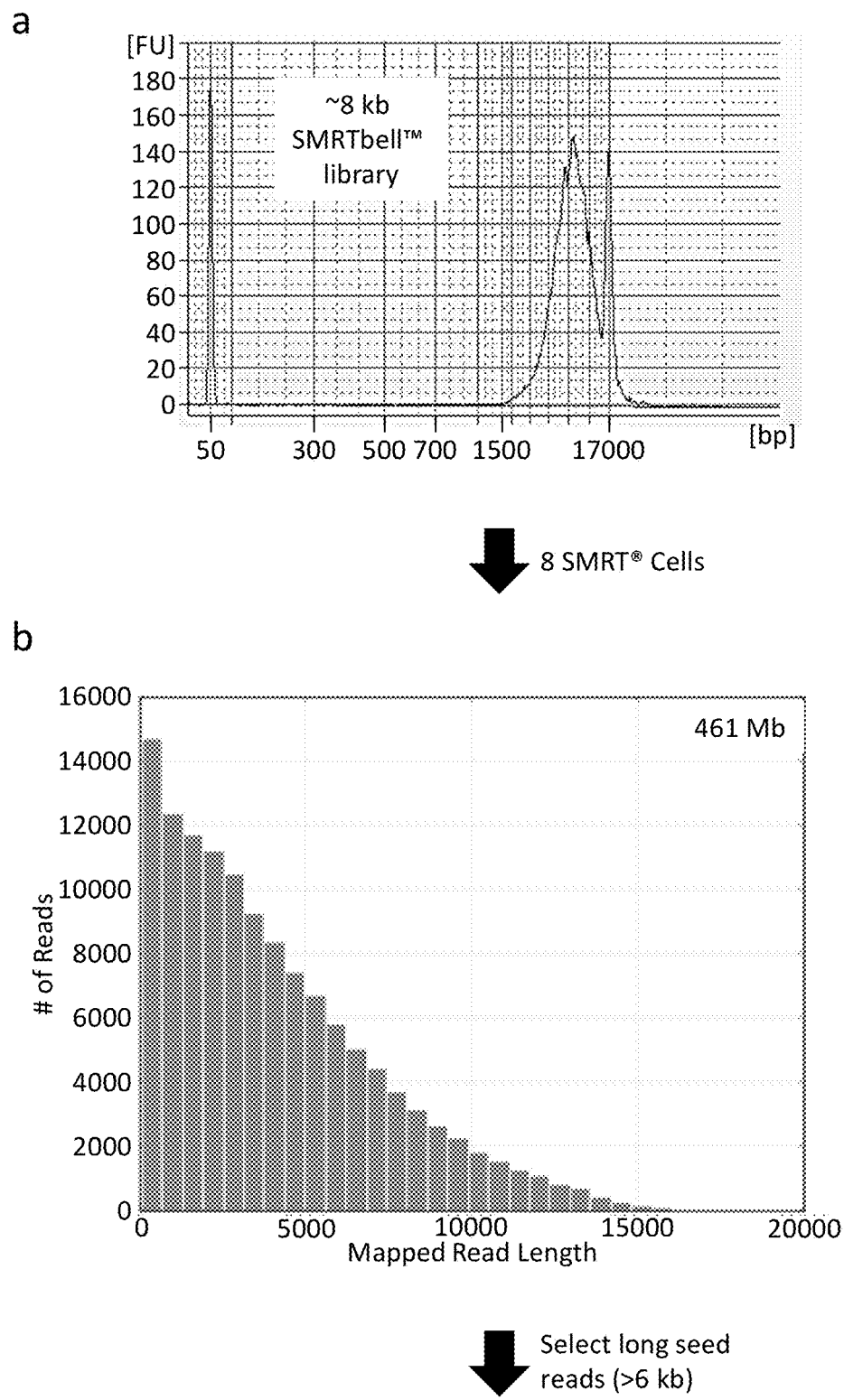
FIG. 5: shows a comparison of de novo HGAP assembly of E. coli MG1655. (a) Bioanalyzer trace of the ~8 kb SMRTbell™ template library used for SMRT® sequencing. (b) Histogram of read length for sequencing data from 8 SMRT® Cells. (c) Read length and accuracy distributions of CLRs against the previously determined Sanger E. coli MG1655 reference. (d) Read length and accuracy distributions of PLRs against the previously determined reference. (e) Dot plot of the final assembly against the previously determined reference.
Figure 5:
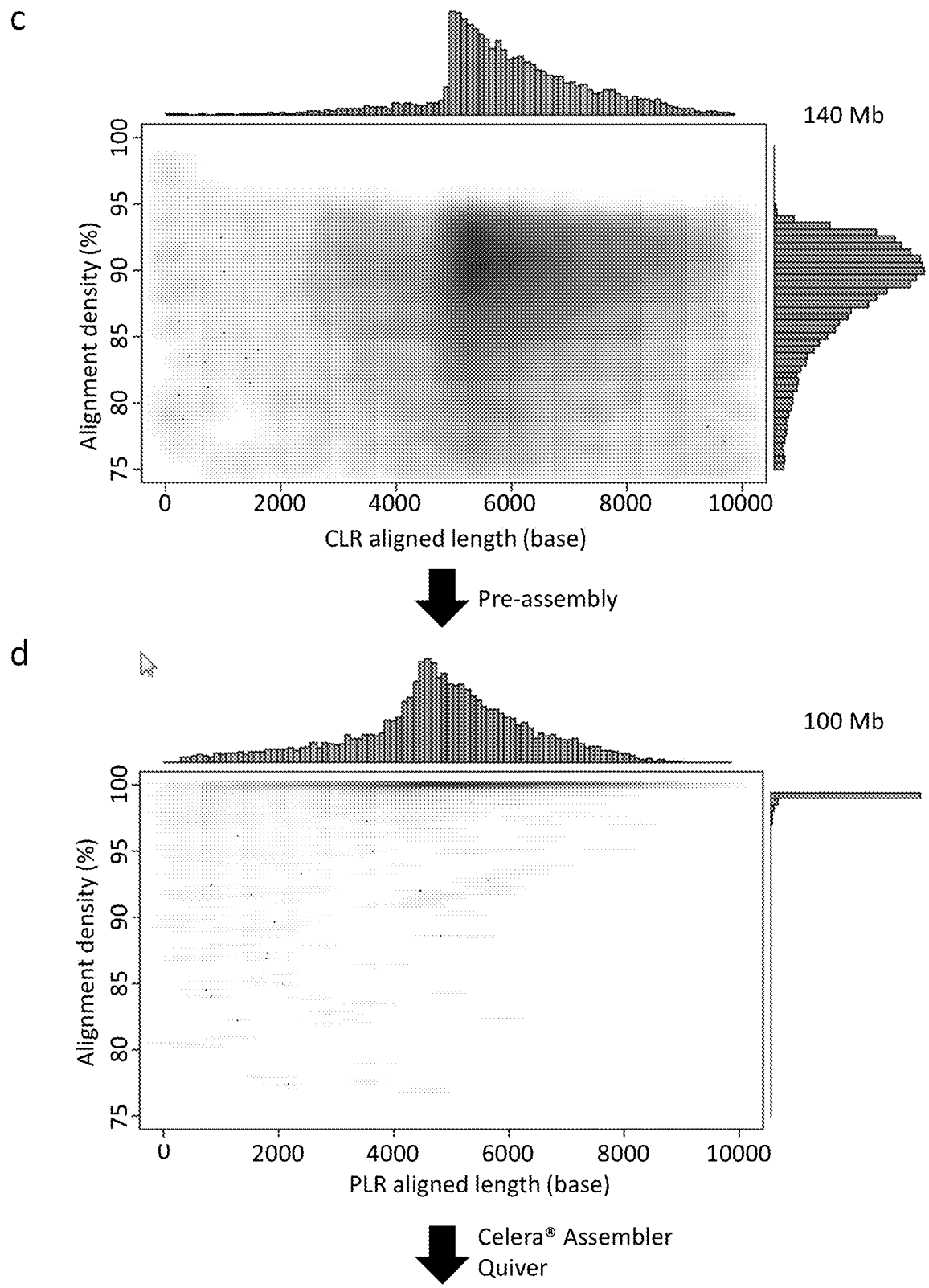
Figure 5:
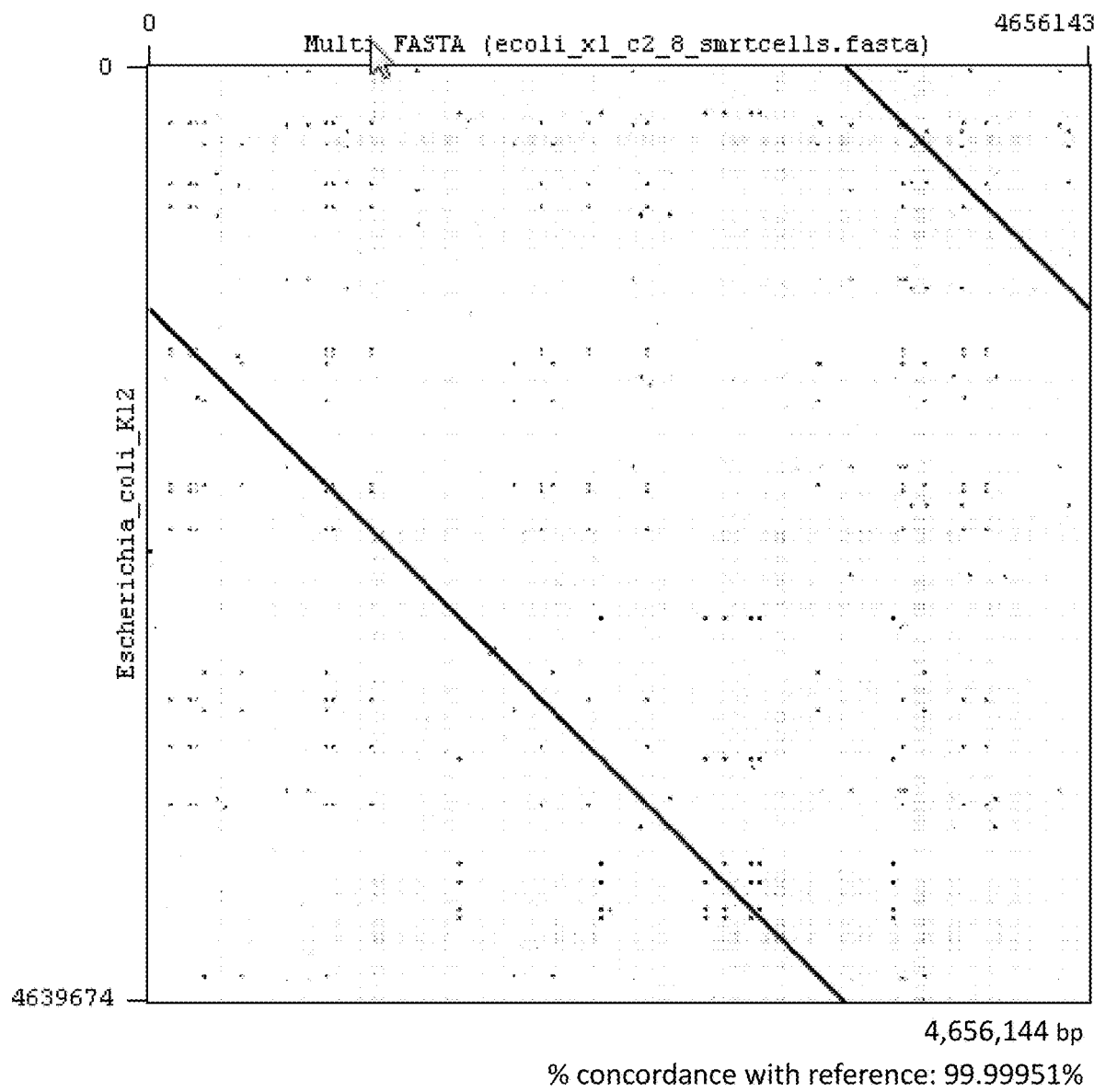
Figure 6A:
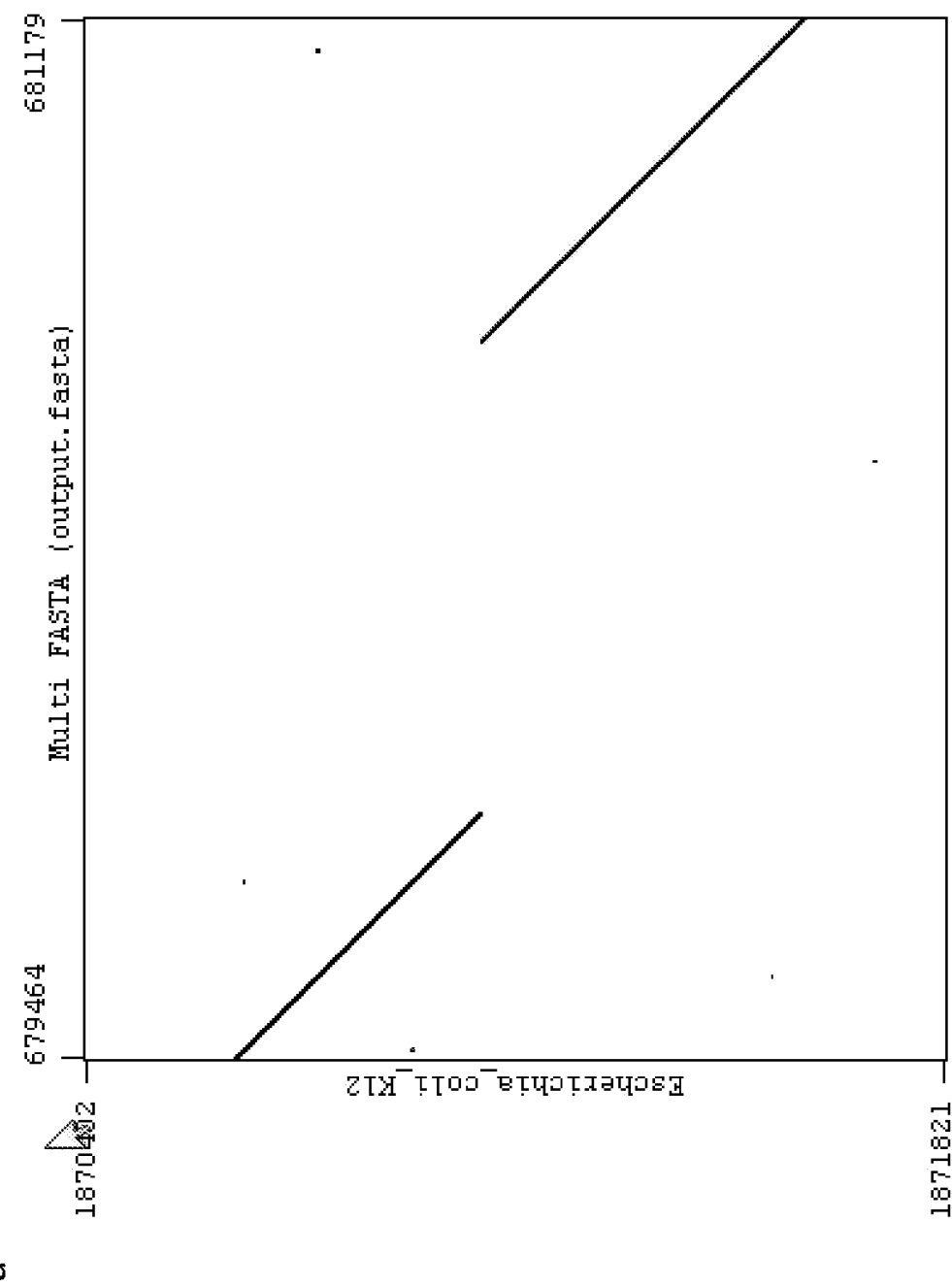
FIGS. 6A-6E show structural variation between the HGAP E. coli assembly and the Sanger-based reference. (a) Dot plot of the region in the assembly containing the observed structural variation. (b) SMRT® sequencing read alignment against the Sanger-based reference, showing the shot-gun read structure discontinuity. (c) SMRT® sequencing read alignment against the HGAP assembly, showing consistency with the read structure.
Figure 6A:
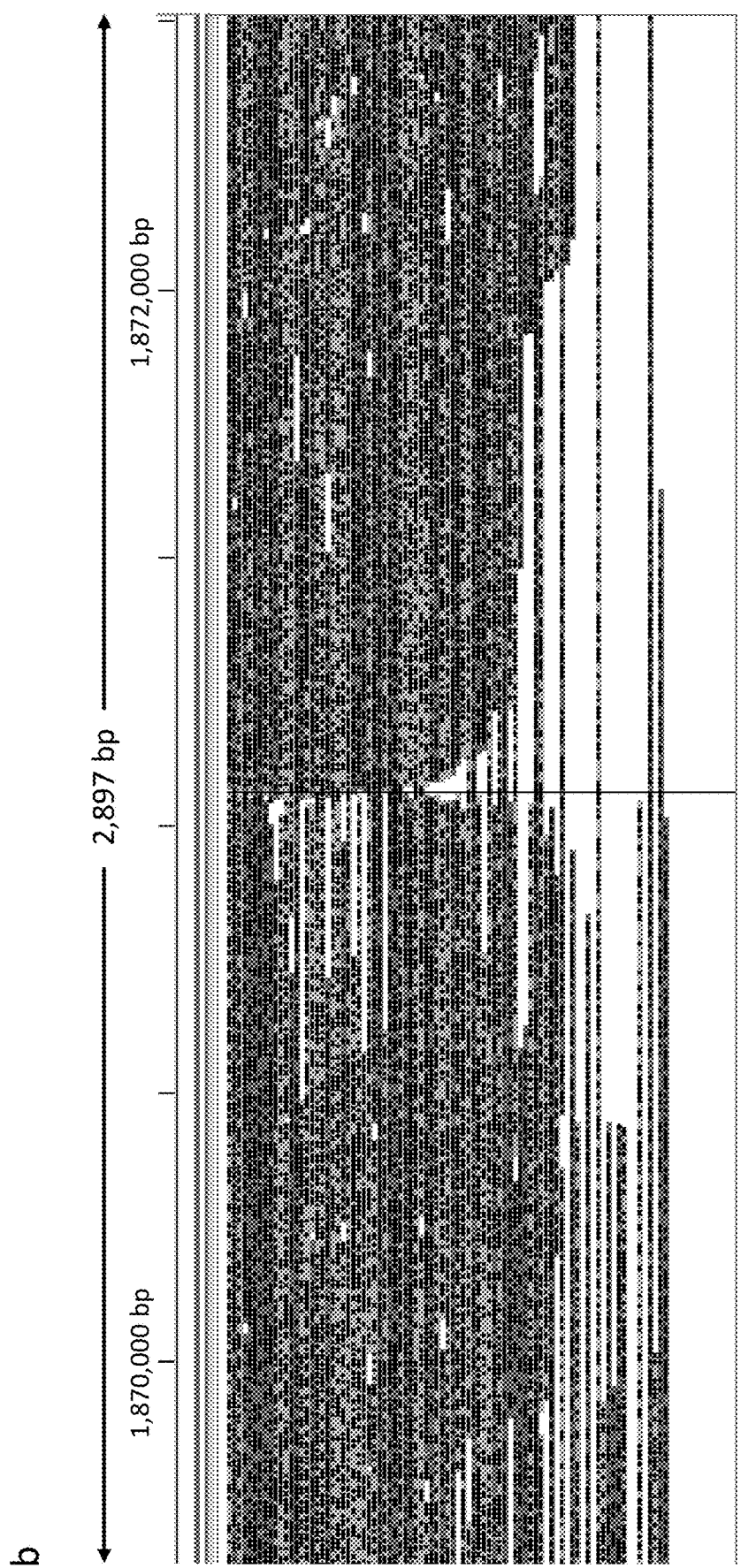
Figure 6A:
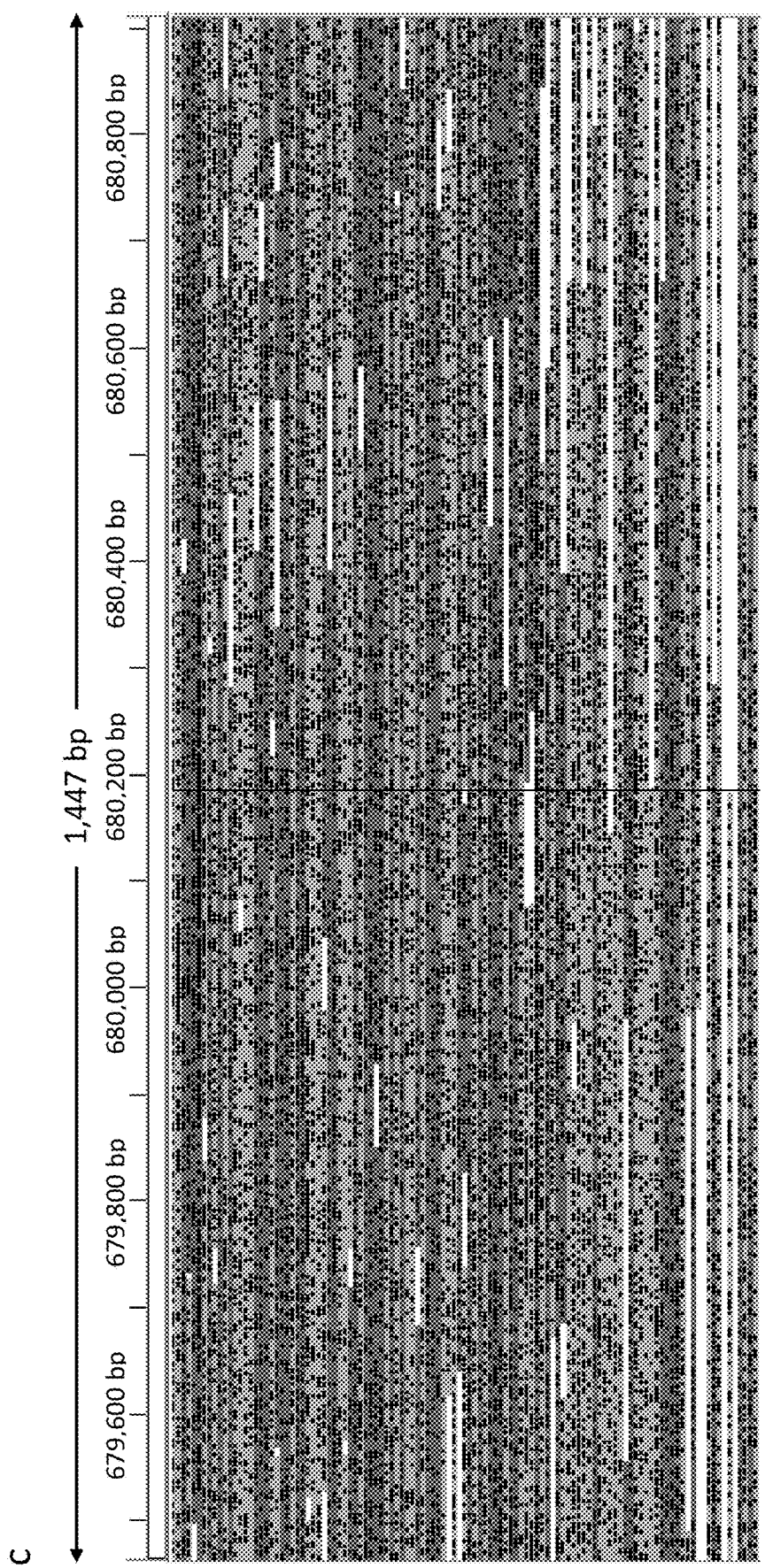
Figure 6B:
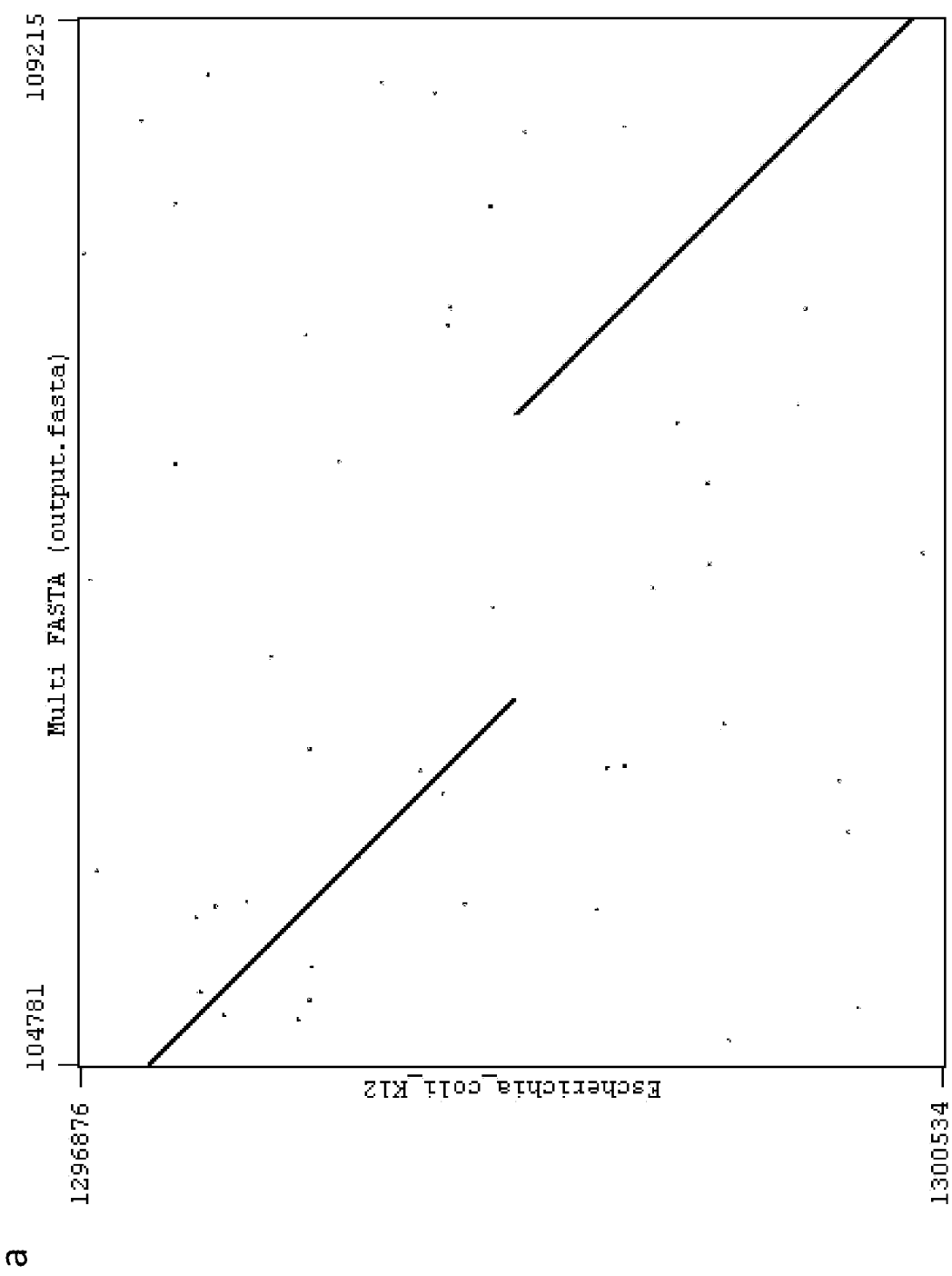
Figure 6B:
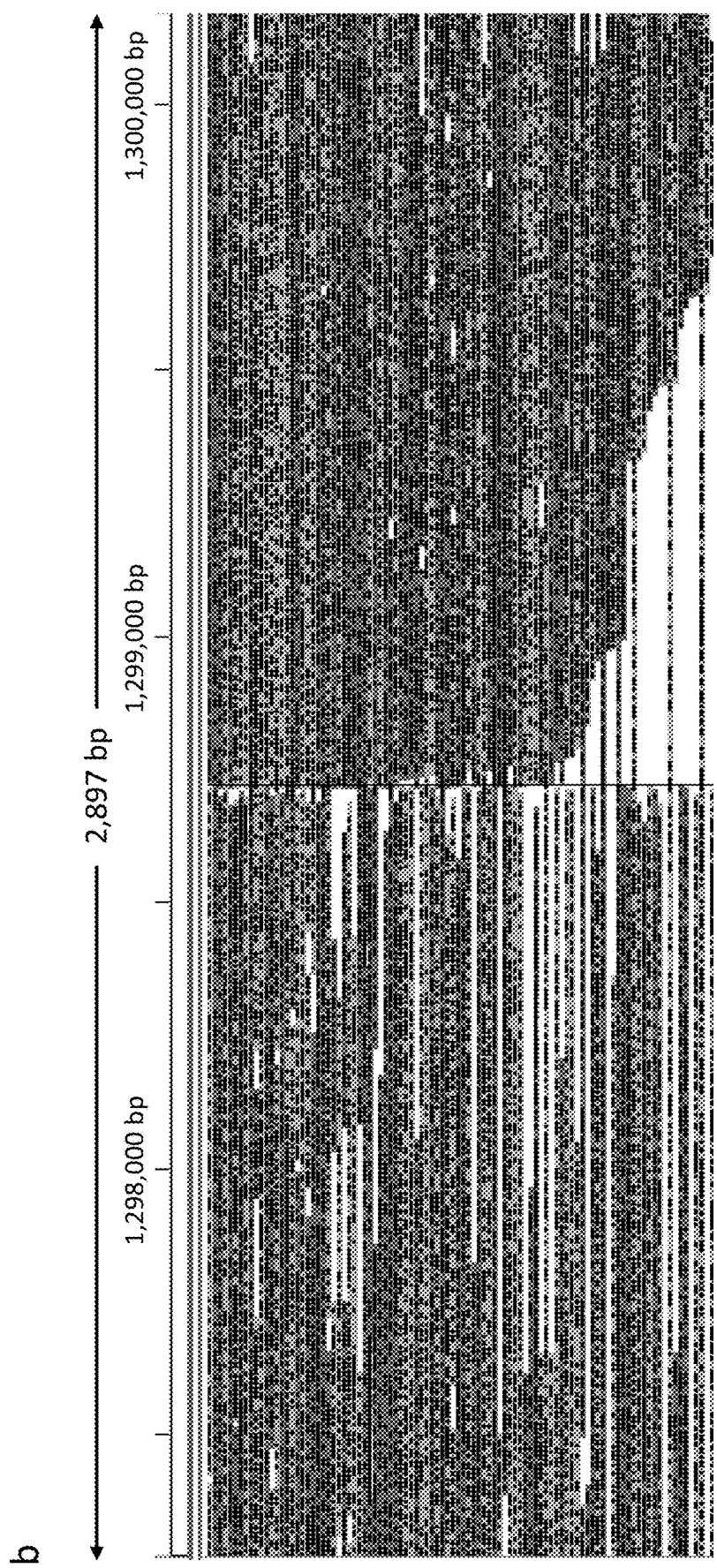
Figure 6B:
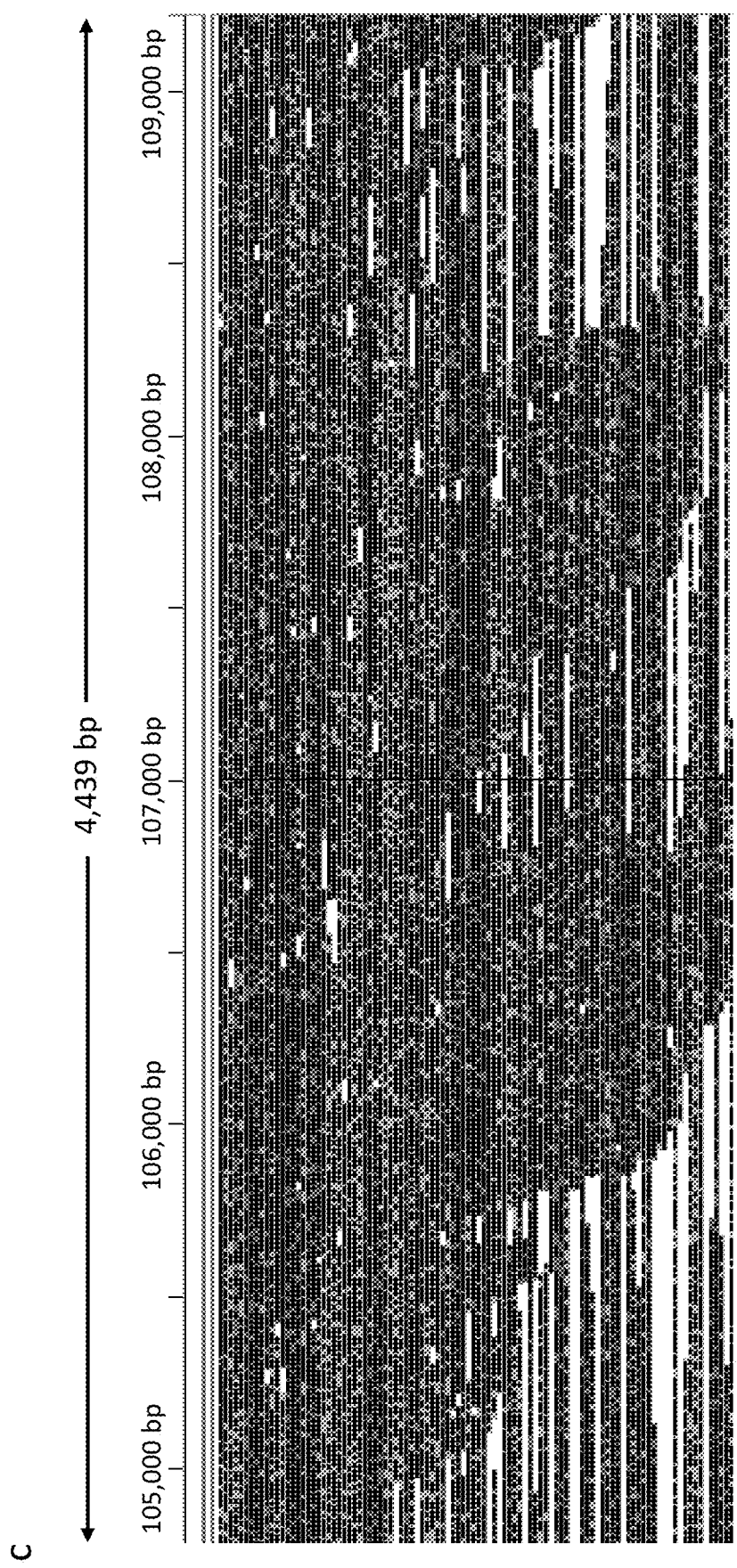
Figure 6C:
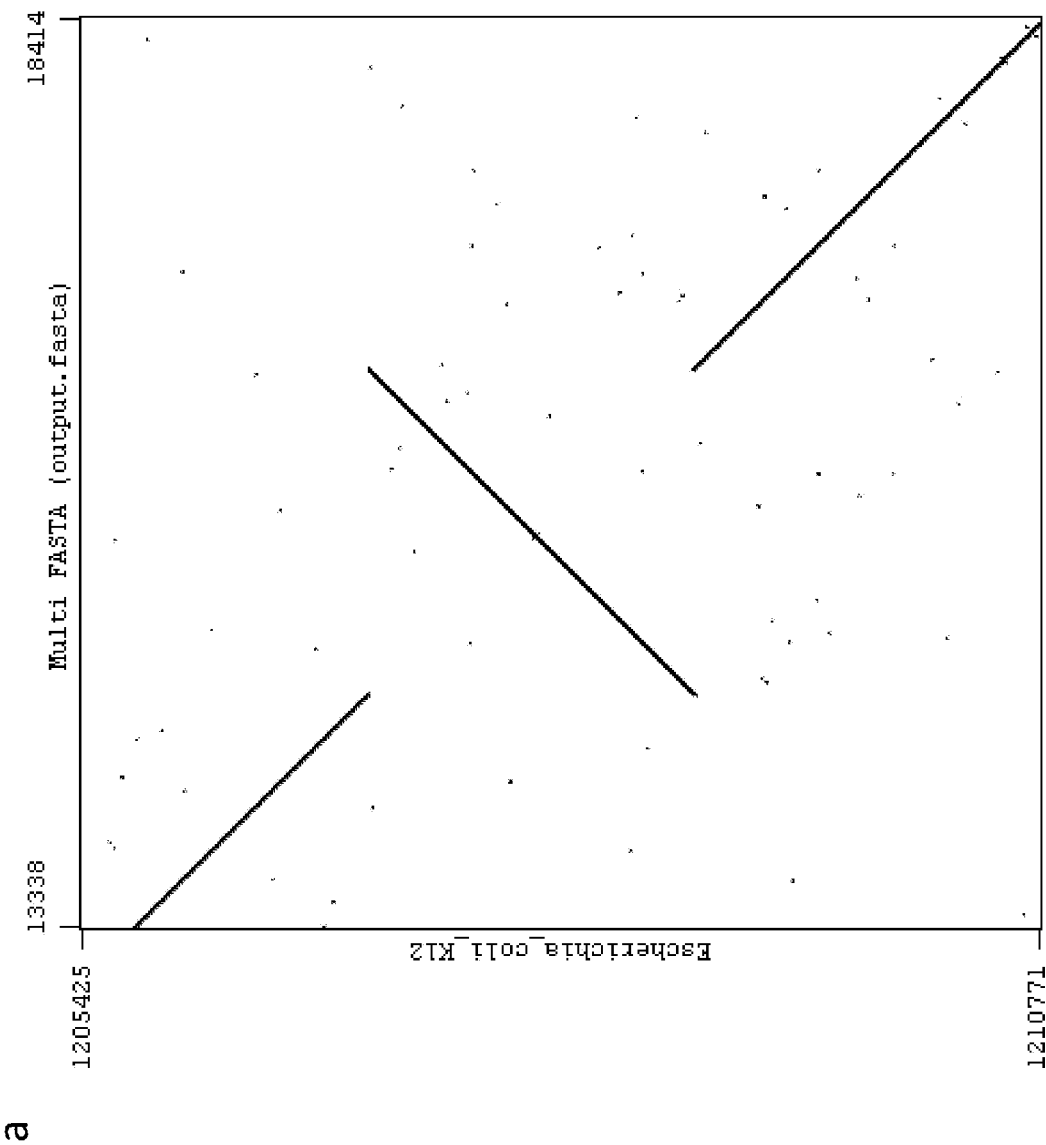
Figure 6C:
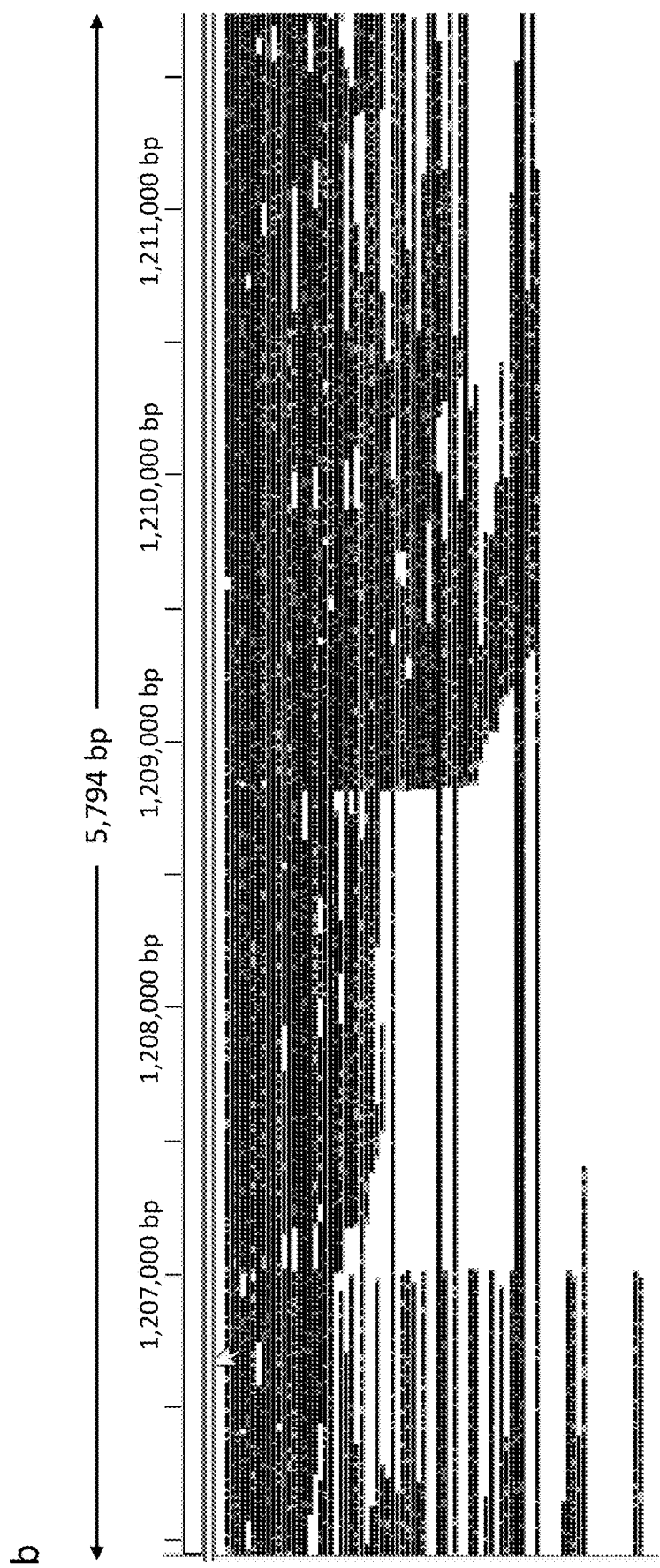
Figure 6C:
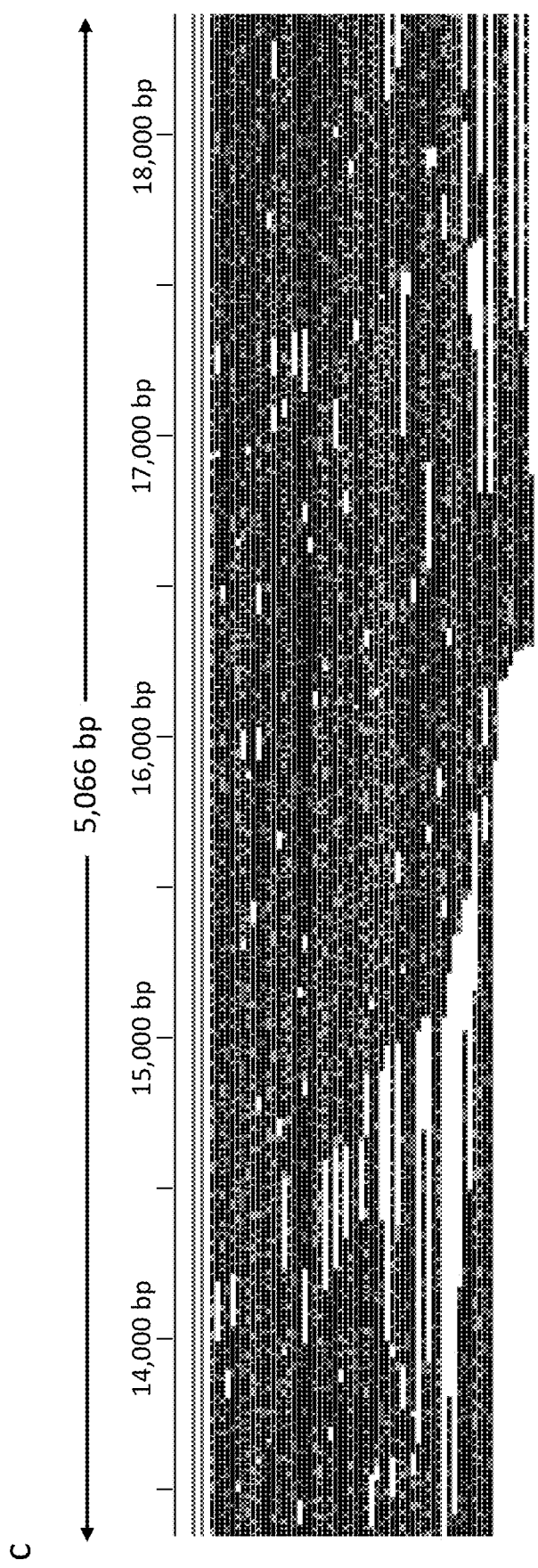
Figure 6D:
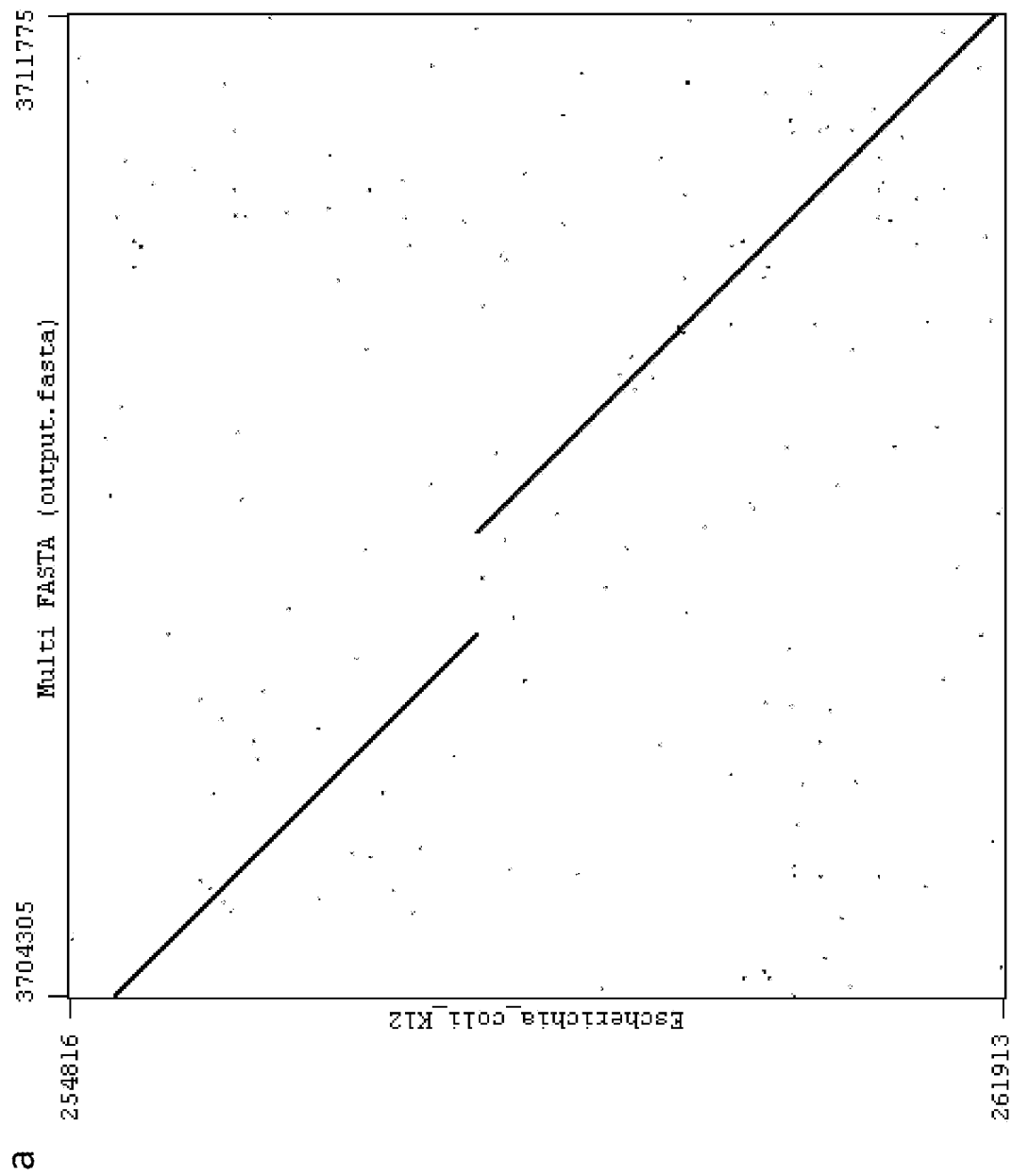
Figure 6D:
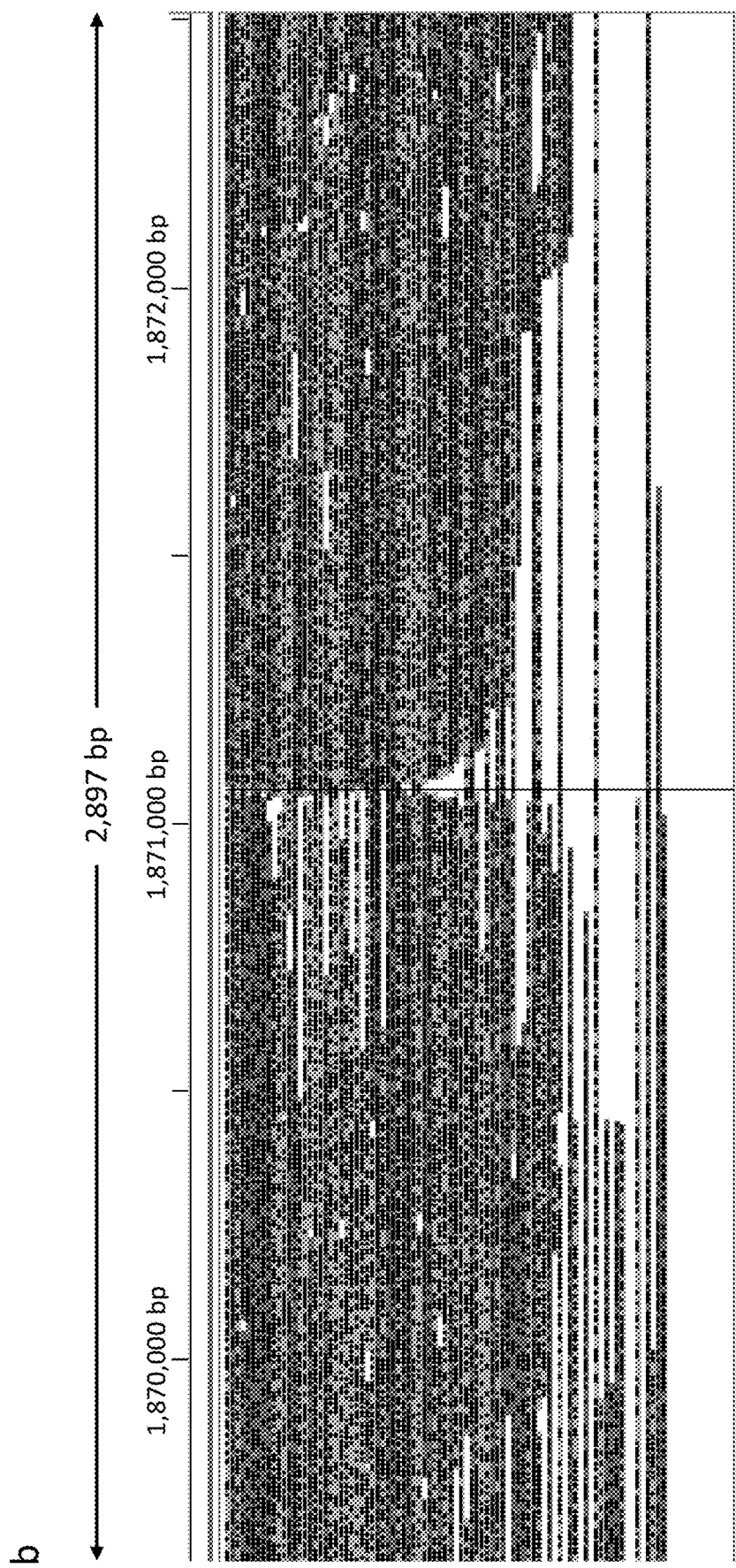
Figure 6D:
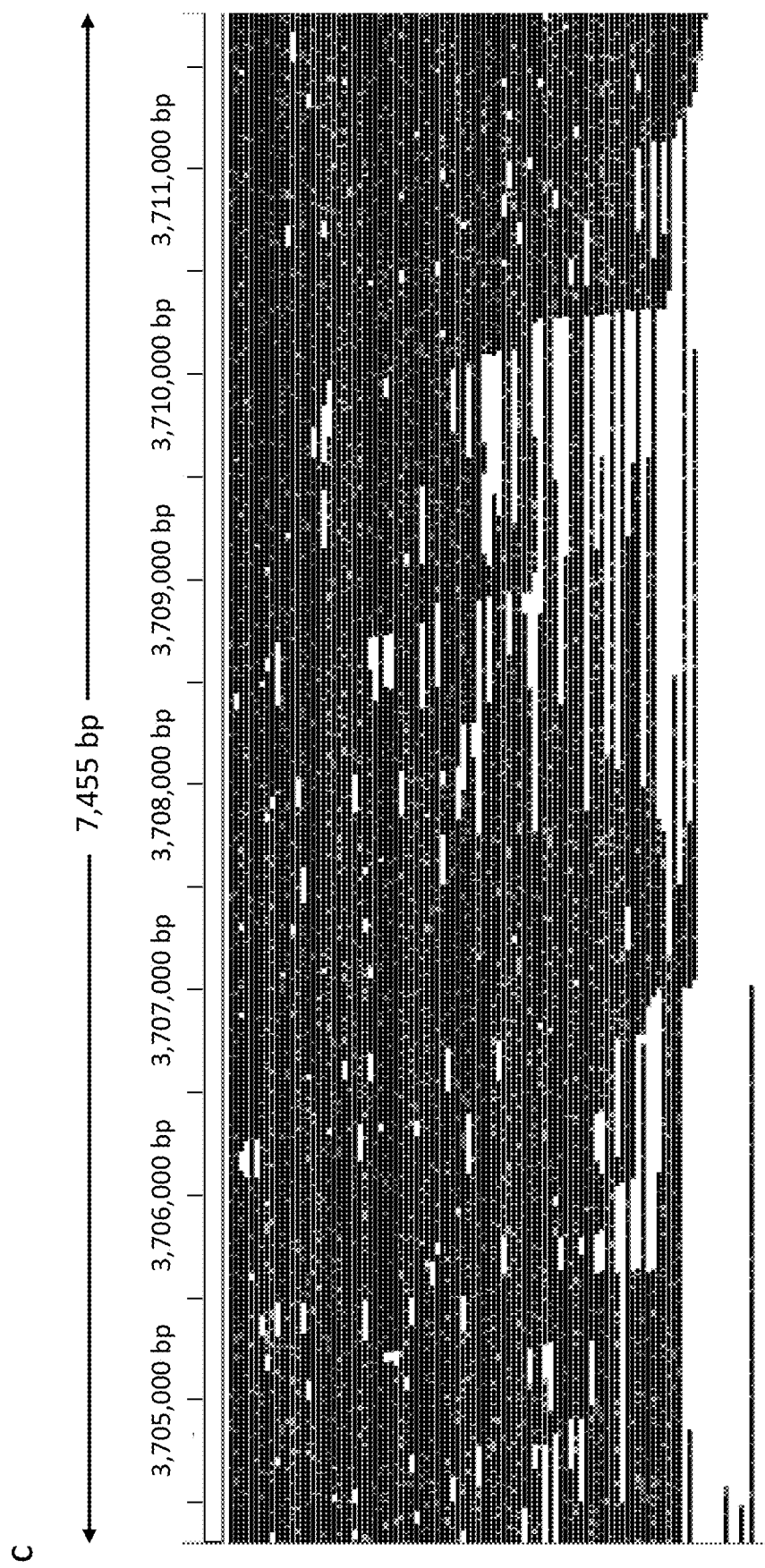
Figure 6E:
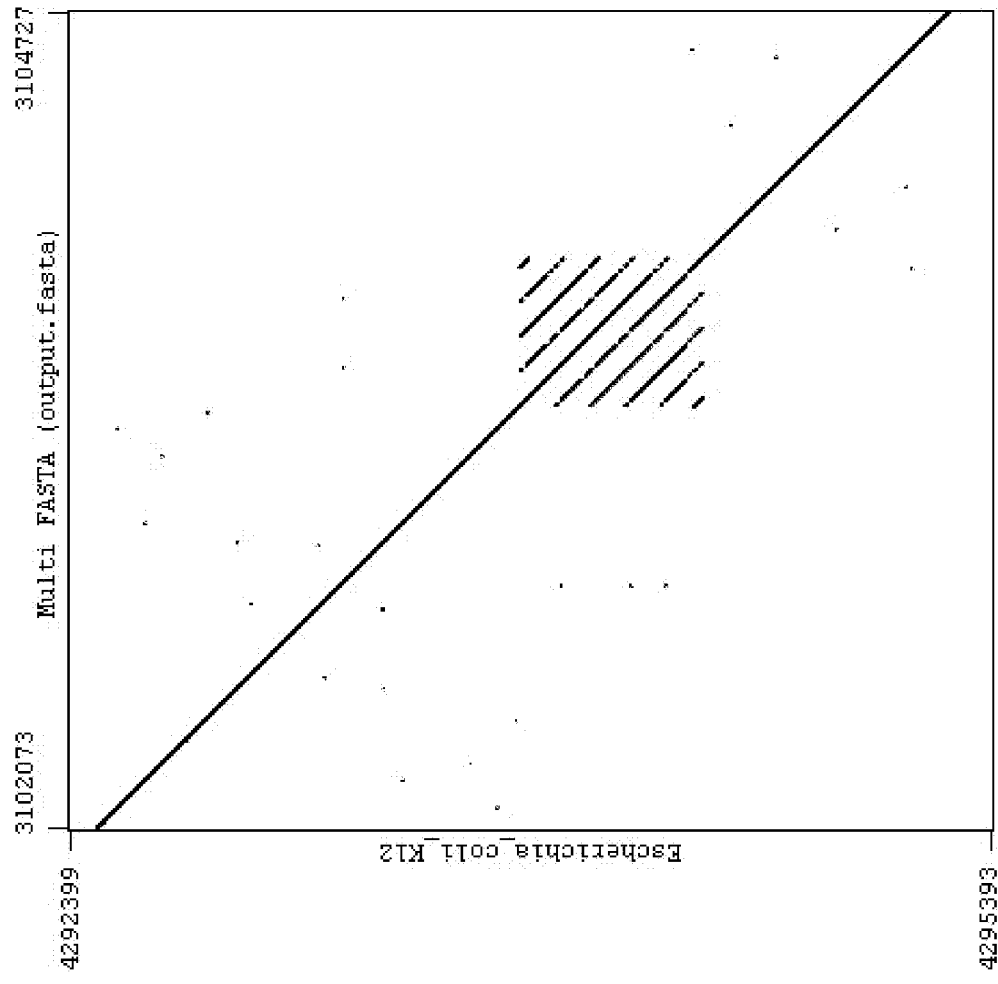
Figure 6E:
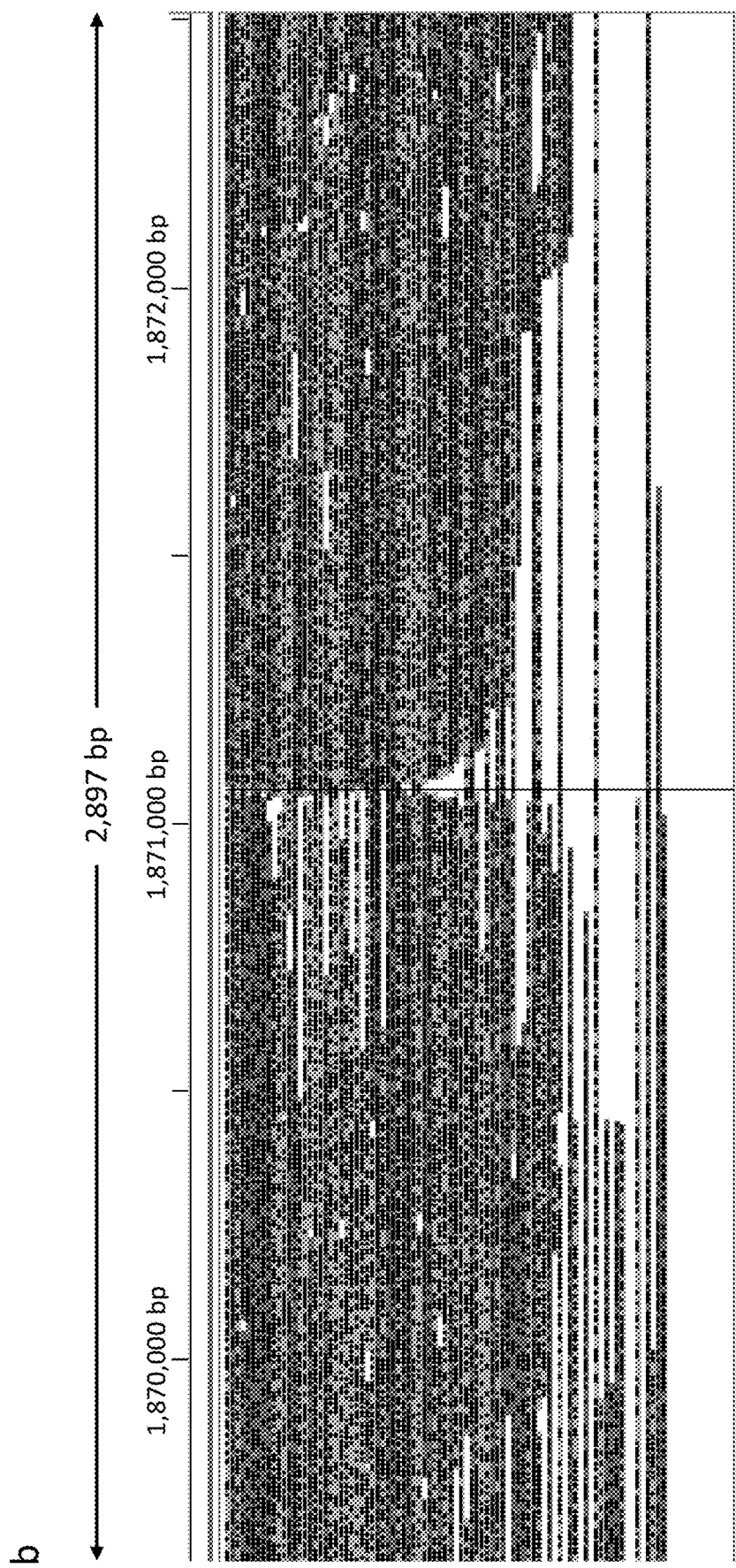
Figure 6E:
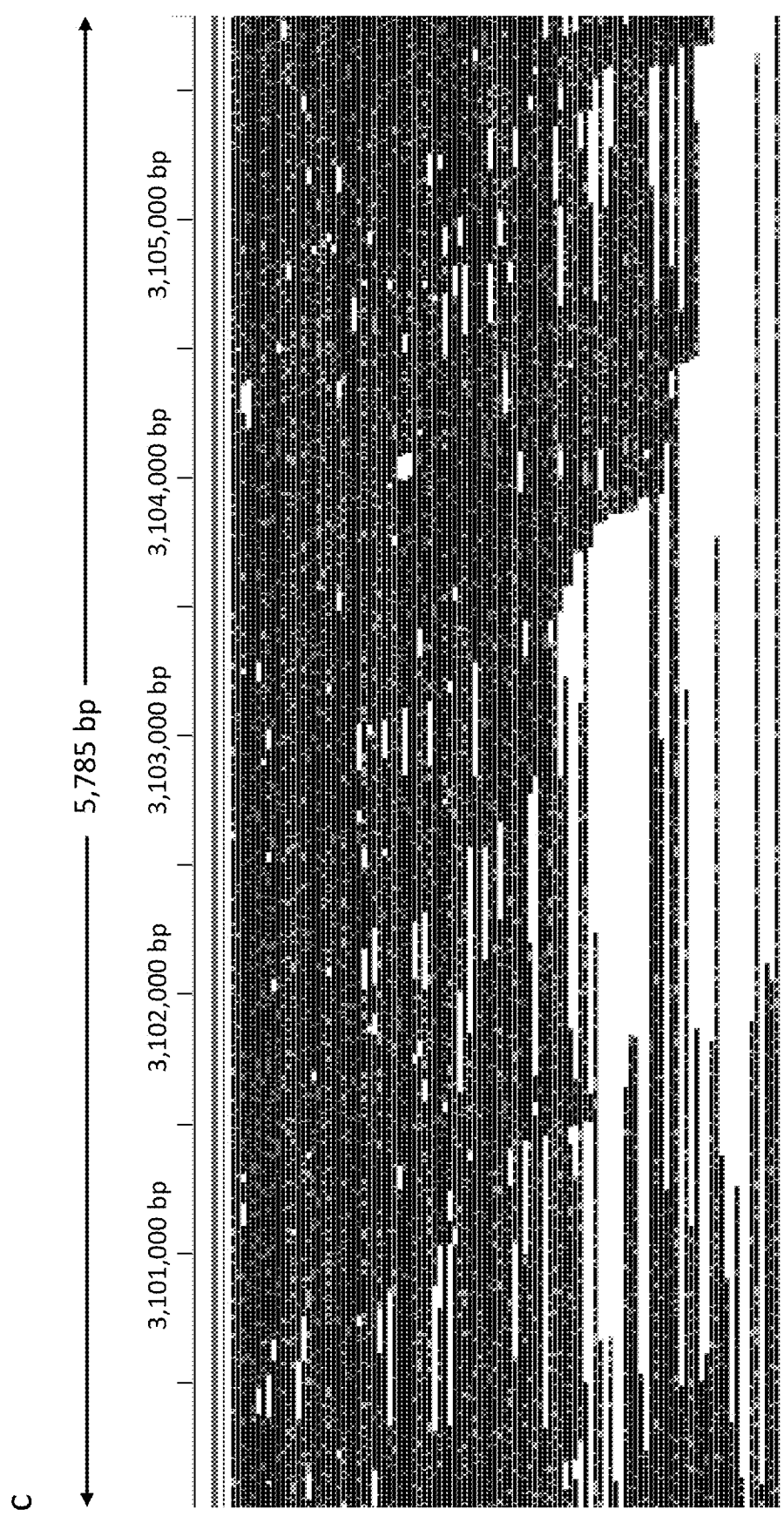
Figure 8:
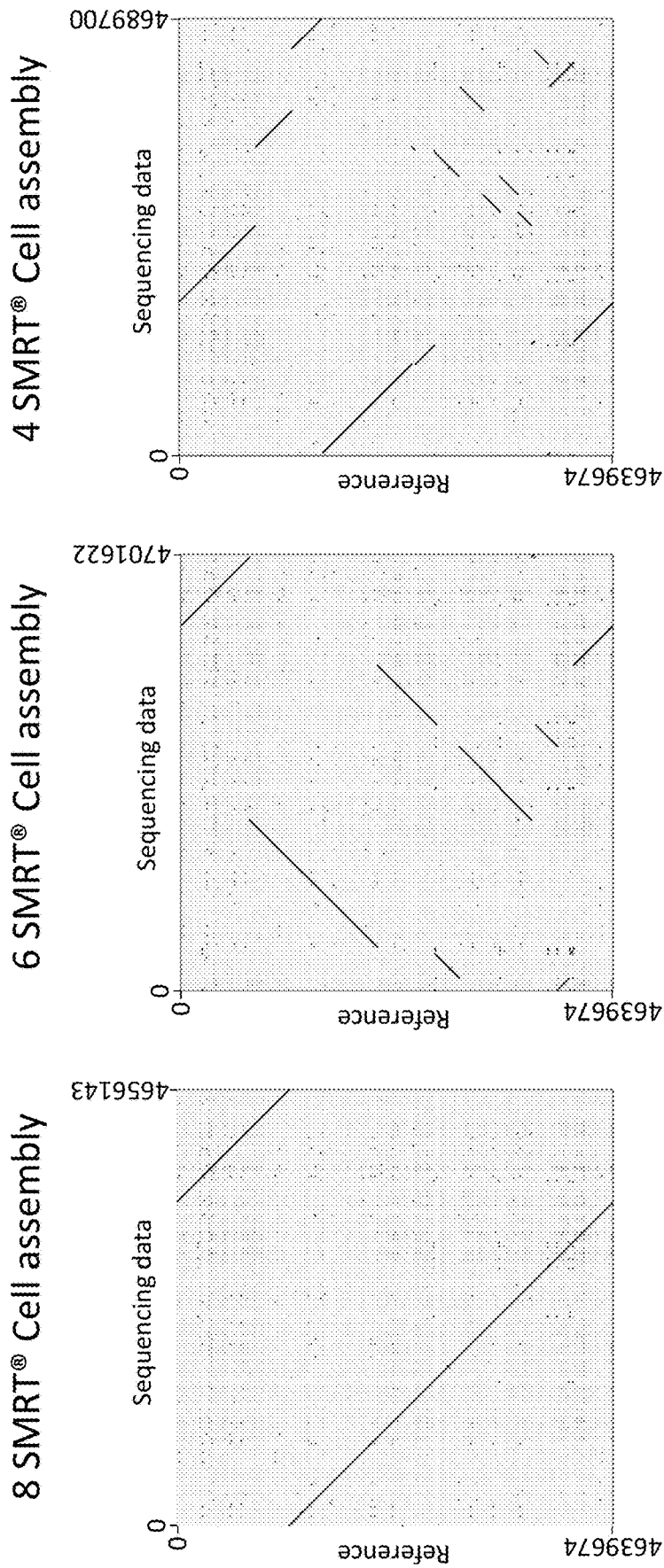
FIG. 8 shows Comparisons of HGAP de novo assemblies against the Sanger reference for Escherichia coli MG1655 (NC_000913.2) for different numbers of SMRT® Cells used in the analysis.
Figure 9:
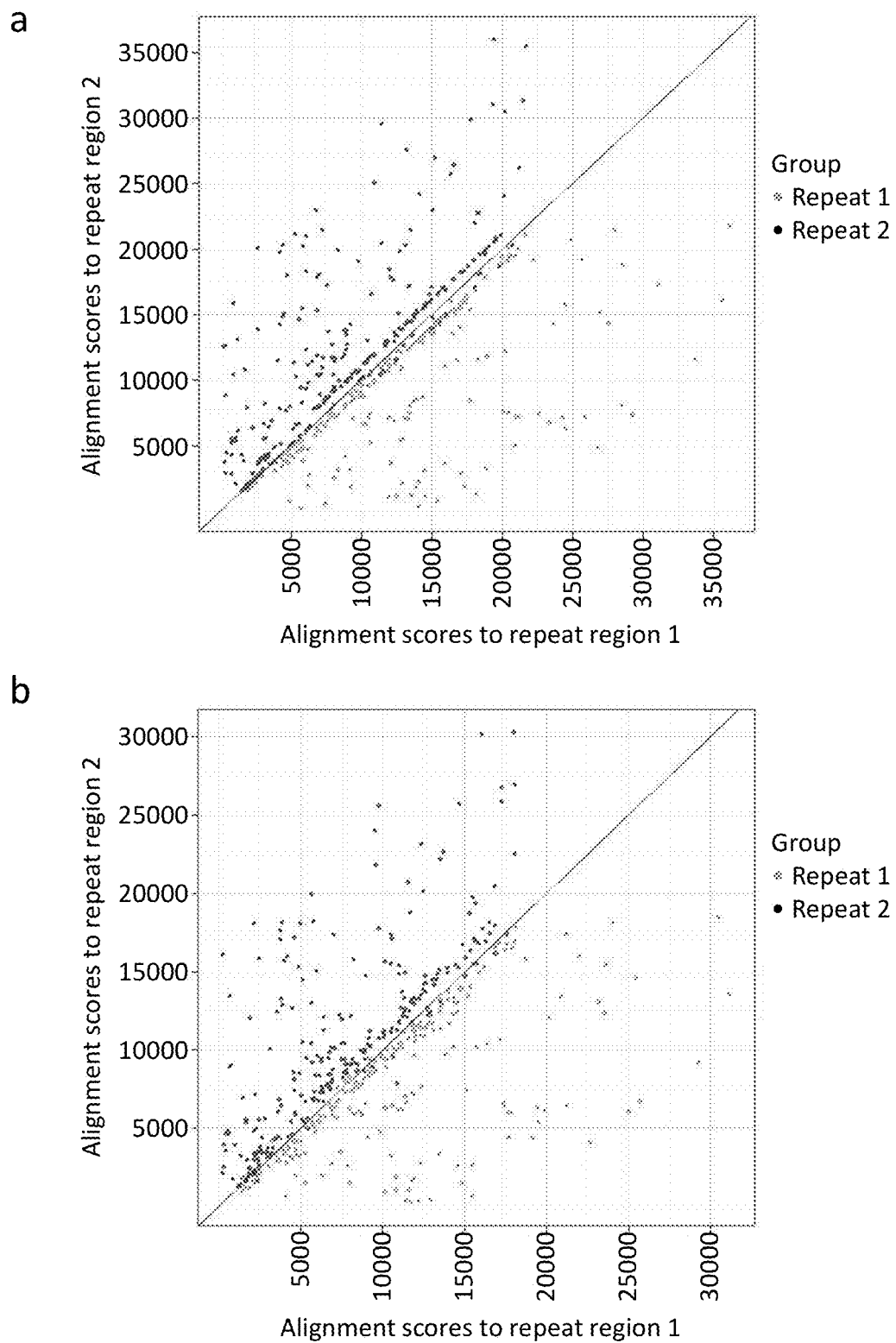
FIG. 9: Remapping of all CLRs for repeat 1 reads and repeat 2 reads to the reference genome (a), and to the seed reads (b) in E. coli MG1655 HGAP assembly. In each panel, the majority of the repeat 1 reads (grey) are in the lower half-triangle below the center line, and the majority of the repeat 2 reads (black) are in the upper half-triangle above the center line.

The workflow from DNA sample to finished genome using the HGAP method is shown in FIG. 5. FIGS. 5c and 5d are identical to FIGS. 2a and 2b respectively, and are duplicated within FIG. 5 for ease of reference. In order to evaluate this new genome assembly method, it was first applied to E. coli MG1655 for which a high-quality reference sequence had previously been generated by Sanger sequencing (Blattner, Plunkett et al., 1997). A single, ~8.5 kb SMRTbeII™ library was prepared (FIG. 5a) and subjected to SMRT® sequencing of 8 SMRT® Cells, yielding 461 Mb of sequence from 141,492 CLRs, with a typical average read-length of 3,257 bases (FIG. 5b). The data were then subjected to the HGAP method (the optional clean-up by Minimus2 or similar tools was not used in this study to show the unaltered output of the HGAP method).

In addition to providing a measure of performance for the final genome assembly, the availability of a high-quality reference allows for a characterization of the algorithm at each of the individual assembly steps. First, the length and accuracy distributions of the seed CLRs are examined by aligning each CLR with a read length above the length cutoff of 6,000 bases to the reference sequence of E. coli MG1655 (FIG. 5c). 17,726 seed CLRs representing ~140 Mb of total sequence fulfill this criterion and have an average aligned read length and single-pass accuracy of 7,213 bases and 86.9%, respectively. The aligned read length is shorter than the overall read length of these reads (8,160 bases) because for some reads, portions representing lower quality regions or chimeric reads do not align.

After the pre-assembly step which converts the CLRs into highly accurate PLRs, 17,232 pre-assembled long reads are obtained, with a mean read length of 5,777 bases and a mean accuracy of 99.9% (FIG. 5d). The average length of the PLRs drops compared to the seed sequences due to trimming of the ends of the PLRs and filtering of spurious and chimeric CLRs. Typically, ~30-35% of total bases are removed during the pre-assembly step in the current implementation of HGAP. This number is a function of the mapping and trimming parameters which can be further optimized to improve the yield and lengths of PLRs in the future.

At this point, it is possible to estimate the number of contigs and the average contig lengths using the Lander-Waterman statistics (Lander and Waterman 1988). With the observed coverage and average length of PLRs for the *E. coli* example, the estimated contig number is less than one. However, since the PLR length distribution does not follow the uniform length distribution assumption of the Lander-Waterman statistics and the genome is not random, the usage of Lander-Waterman should be considered as just a quick estimate of the amount data needed for a good assembly (Schatz, Delcher et al. 2010). When the genome has no complicated repeats, this estimate is found to be a good predictor when the mean read length is long.

Subjecting the PLRs to the Celera® Assembler yielded 2 contigs, one contig 4,656,144 bases in length representing the *E. coli* genome, and a spurious small contig (7,589 bases, aligning to positions 2,393,788-2,401,380 of the reference with 99.96% identity). A genome-wide alignment to the known reference sequence is illustrated by the dot blot in FIG. 5*e*, and shows that the assembly spans the entire *E. coli* reference and is co-linear with it (FIG. 5*e*). The final assembly statistics are shown in Table 1A and in further detail in Table 1B (FIG. 7). Since the Celera® Assembler assumes the genome to be linear, the assembly is slightly larger (100.35%) than the reference because the ends of the single contig that cover a genome can have overlaps. Such linear contigs can be further processed to create the finished circular genome.

Dot plots are commonly used in bioinformatics to compare two biological sequences and identify regions of similarity between them. (See, e.g., Gibbs, et al. (1970) *Eur. J. Biochem.* 16:1-11, incorporated herein by reference in its entirety for all purposes.) Where the sequences match, a dot is present in the matrix, and a region of identity results in a diagonal line (a series of dots in the matrix). The number and length of the diagonal lines provides a measure of the similarity between the sequences. Identical sequences will have a diagonal line bisecting the matrix, and insertions, deletions, translocations, inversions, etc. can give rise to disruptions in this diagonal. Duplications of a region in one sequence but not the other give rise to additional diagonal lines in addition to the central one. As such, the main diagonal lines represent regions over which the two sequences align with one another, while lines off the main diagonal represent similar or repetitive patterns within the sequence. The use of dot plots to compare biological sequences is well known and routinely used in the art.

The consensus accuracy of the assembly was evaluated with genome-wide alignments using the Mummer package (Kurtz, Phillippy, et al., 2004). The de novo sequence result contained 23 differences to the canonical reference, corresponding to a nominal QV of 53 (99.9995% identity). To evaluate the effect of the quiver consensus algorithm on the final quality of the assembly, the reference concordance was compared before and after the Quiver consensus step. Since not all potential sequencing errors are removed in the pre-assembly step, it is likely that the output from the Celera® Assembler still contains some errors. In this assembly, the number of discordances between the draft assembly and the reference before the final Quiver consensus step was 49. Thus, after applying Quiver to generate the final consensus, a more than 2-fold increase in the consensus accuracy is observed. Correspondingly, the high accuracy of the final assembly allowed correct prediction of over 99% of all genes present in the organism (Table 1A).

TABLE 1A

HGAP assembly statistics summary for three different microorganisms and one human BAC. The Celera ® Assembler was used for assembly unless noted otherwise. For full statistics, see Table 1B (a)-(d) (FIG. 7).

| SMRT Cells | CLR bases (Mb) | Assembly size | Number of contigs >10 kb (all) | Genome covered | N50 | Concordance with Sanger reference | Nominal QV | Genes predicted |
|---|---|---|---|---|---|---|---|---|
| *Escherichia coli* (MG 1655): | | | | | | | | |
| 8 | 461 | 4,656,144 | 1 (2) | 100.35% | 4,648,564 | 99.99951% | 53.1 | 99.8% |
| 6 | 341 | 4,701,623 | 10 (14) | 101.34% | 1,163,944 | 99.99938% | 52.1 | 100.0% |
| 4 | 232 | 4,689,701 | 17 (21) | 101.08% | 392,114 | 99.99876% | 49.1 | 98.8% |
| *Meiothermus ruber* (DSM 1279): | | | | | | | | |
| 4 | 334 | 3,098,781 | 1 | 100.04% | 3,098,781 | 99.99965% | 54.5 | 99.4% |
| 3 | 248 | 3,098,729 | 1 | 100.04% | 3,098,729 | 99.99958% | 53.8 | 99.3% |
| 2 | 170 | 3,102,769 | 3 | 100.17% | 1,053,479 | 99.99897% | 49.9 | 99.2% |
| *Pedobacter heparinus* (DSM 2366): | | | | | | | | |
| 7 | 485 | 5,171,533 | 2 (3) | 100.08% | 2,927,691 | 99.99959% | 53.9 | 99.4% |
| 7* | 485 | 5,197,624 | 1 (5) | 100.59% | 5,164,849 | 99.99960% | 53.9 | 99.3% |
| 6 | 408 | 5,173,388 | 2 (3) | 100.12% | 2,928,902 | 99.99969% | 55.1 | 99.3% |
| 6* | 408 | 5,174,349 | 2 (3) | 100.13% | 3,511,353 | 99.99969% | 55.1 | 99.3% |
| 4 | 274 | 5,184,825 | 11 (18) | 100.34% | 1,403,814 | 99.99944% | 52.5 | 99.0% |
| 4* | 274 | 5,196,690 | 15 (22) | 100.57% | 1,258,275 | 99.99950% | 53.0 | 98.9% |
| *using the MIRA assembler | | | | | | | | |
| Human BAC (VMRC53-364D19): | | | | | | | | |
| 1 | 85 | 186,053 | 1 (4*) | 100.00% | 186,053 | NA | NA | NA |

*the 3 additional contigs were the result of *E. coli* contamination

Of the remaining 23 differences of the HGAP assembly to the Sanger-based reference, 7 single point mutations had previously been observed in the *E. coli* sample used in this study, and had been validated with targeted, PCR-based Sanger sequencing (Table 2). In addition, 5 local structure variations were observed. SMRT® sequence reads mapping to all five structural variation regions showed that the long read data support these structural variations, indicating that the particular strain of *E. coli* K12 MG1655 was different from the canonical reference strain in these regions (FIGS. 6A-E). One of these structural variations was validated using PCR-Sanger sequencing (data not shown).

Tables 1A, 1B, and FIG. 7 show the assembly quality generally as a function of different amounts of sequencing data. Using sequencing data from only six or four SMRT® Cells, HGAP returned 7 and 17 contigs above 0.1 Mb (14 and 21 total), respectively. In all cases, >98.9% of all genes were correctly predicted from the assemblies. Therefore, for certain applications where close-to-finished genomes for different strains are sufficient and fully finished genomes are not required, it may be more economical to run a smaller number of SMRT® Cells to achieve adequate genome assemblies.

Figure 10:
FIG. 10: Resolving repeats in E. coli MG1655. Alignment views of two seed CLRs that span two different rRNA operon repeats. Read types: Type i: Reads span through the repeat region; Type ii: Reads can be anchored by at least one unique region; Type iii: Reads are fully within the repeat region; Type iv: Reads which do not intersect with the repeat region.
Figure 10:
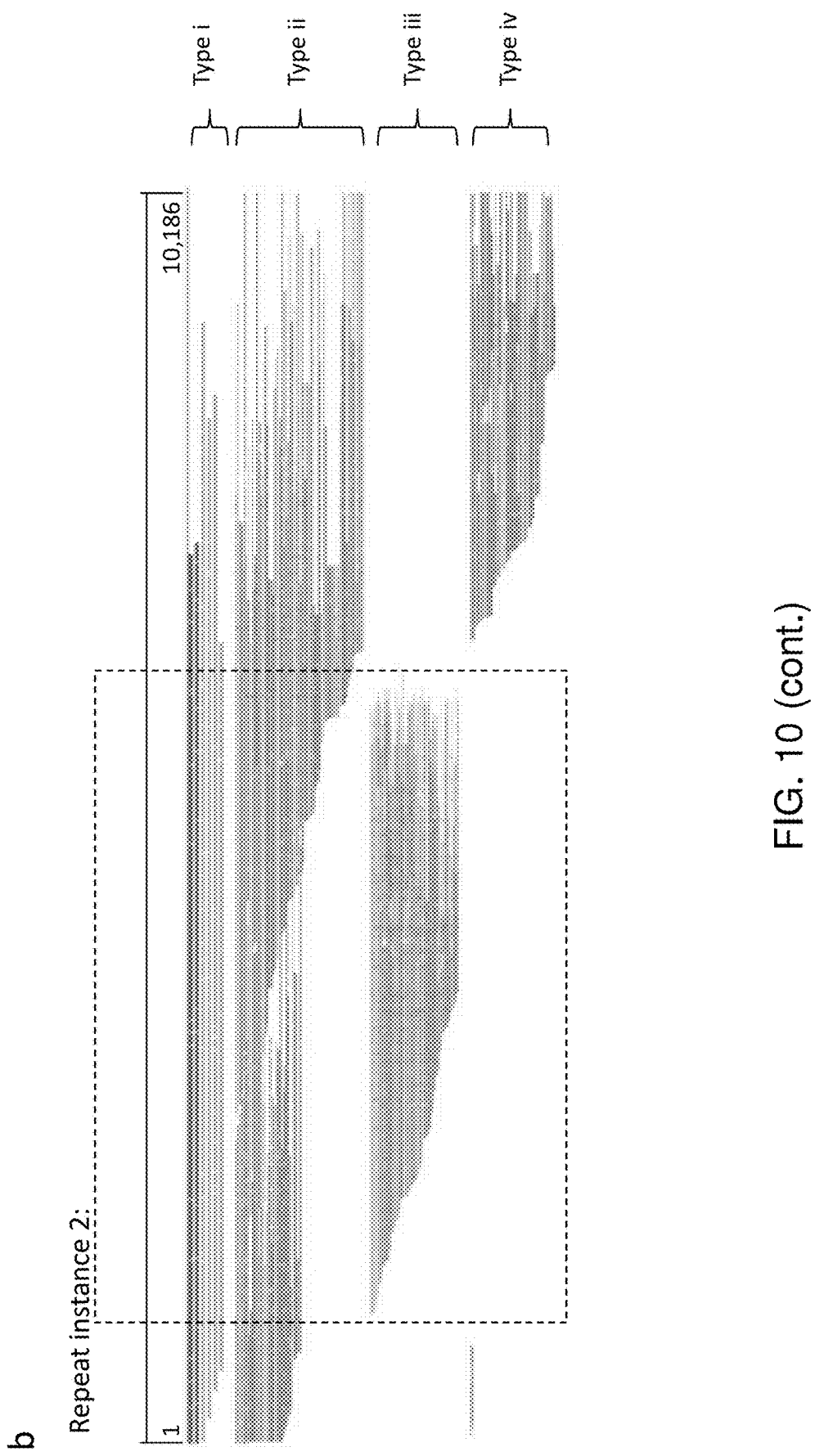

One of the most important pre-requisites for obtaining high-quality, finished genome assemblies lies in the ability to resolve repeats from the data provided by a given sequencing technology. Very long, exact repeats can cause mis-assemblies and/or fragmented assemblies if the sequence reads are not long enough to span the repeats with unique flanking sequences. For non-exact repeats, it is important that sequence reads are correctly discerned from different instances of a repeat. HGAP's capability to resolve and distinguish repeats in genomes can be assessed by comparing the rRNA operon repeats in *E. coli* MG1655, where the similarity between the repeats are greater than 95.9% (see FIG. 4). Two seed reads that correspond to repeat regions within positions 2,724,000-2,734,436 and 3,420,825-3,431,015 of the reference, respectively, were selected. The two regions have 95.9% identity over 5,404 bp. FIG. 10 shows the alignments of all other CLRs mapping to the two repeats. For each of the seed reads, there are 4 types of CLRs that mapped to them: (i) the reads are anchored by unique regions at both ends; (ii) the reads are anchored on one unique end only; (iii) the reads map fully within the repeat region, and (iv) the reads are not overlapped with the repeat regions. Type (i) and (ii) reads are unlikely mis-mapped because they have unique flanking sequences. When a repeat is smaller than the average read length, most of CLRs will be type (i) and (ii), generating excellent assemblies and consensus accuracies regardless the similarity of the repeat to other copies of the genome. In the case of very long repeat regions, there will be more reads that are of type (iii) for which the only information to avoid mis-mapping is the real biological differences between the different copies of the repeat. For the above example, because the sequencing errors are random and do not correlate with the differences between repeats, most of the type (iii) reads still map correctly. To demonstrate this, all CLRs from the two repeat regions were aligned to either the Sanger reference (FIG. 10, panel (a)) or the seed reads (FIG. 10, panel (b)), and compared the alignment scores. Although the two seed reads in FIG. 10 have accuracies of 88.4% and 89.8% which are smaller than the 95.9% identity between the repeats, the CLR alignment scores have sufficient sensitivity to distinguish them, allowing even type (iii) reads to map correctly.

TABLE 2

Single nucleotide differences of the 8 SMRT® Cell *E. coli* assembly vs. the *E. coli* K12 MG1655 reference (Genbank accession: NC000913.2). The SNPs highlighted were validated via PCR-Sanger sequencing.

| reference coordinate | variant | validated |
|---|---|---|
| 367,076 | InsC | |
| 367,076 | InsG | |
| 547,694 | A>G | |
| 547,834 | InsG | |
| 1,211,310 | CDel | |
| 1,349,219 | GDel | |
| 1,419,673 | CDel | |
| 2,104,943 | InsA | |
| 2,171,385 | InsC | |
| 2,171,385 | InsC | |
| 2,217,429 | GDel | |
| 2,483,917 | CDel | |
| 2,626,447 | A>T | Yes |
| 2,686,635 | CDel | |
| 2,735,734 | GDel | |
| 3,274,977 | ADel | |
| 3,365,619 | ADel | |
| 3,401,979 | InsG | |
| 3,439,005 | A>T | Yes |
| 3,558,478 | GDel | Yes |
| 3,662,133 | TDel | |
| 3,957,957 | C>T | Yes |
| 4,621,806 | A>G | Yes |

In SMRT® sequencing, if the exact repeat lengths are longer than the maximum length of a sequence run data set, more data can sometimes be collected to increase the chances of obtaining sequence reads that can span through these repeats to resolve them. As an example, the four SMRT® Cell assemblies described above with a total of 17 contigs over 10,000 bases (21 contigs total) shows most contigs in this assembly end at the rRNA operon repeats. As expected, such ~5 kb repeats were successfully resolved by obtaining more sequencing data to capture longer reads that cover these long repeat regions, thereby yielding a two-contig assembly using sequencing data from 8 SMRT® cells, with all rRNA operon instances fully resolved.

Figure 11:
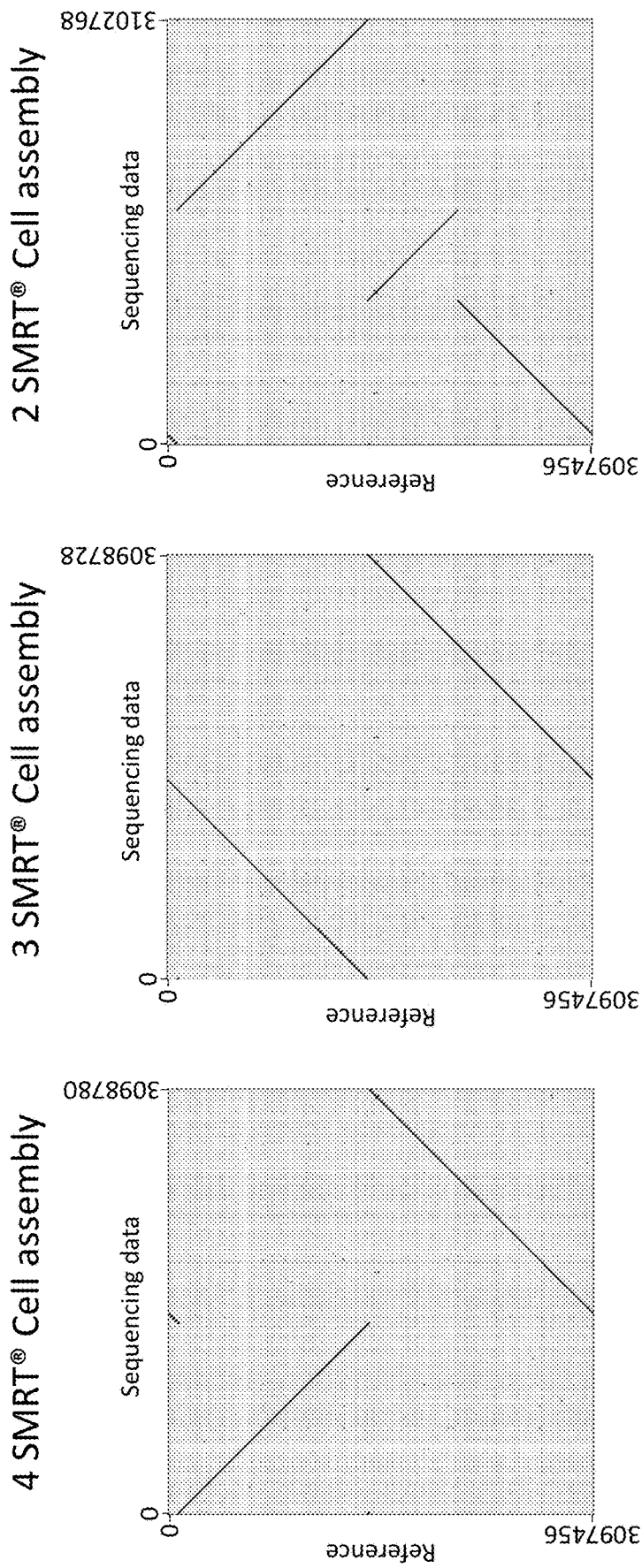
FIG. 11 shows comparisons of HGAP de novo assemblies against the Sanger reference for Meiothermus ruber (NC_013946.1) for different numbers of SMRT® Cells used in the analysis.

The HGAP method has been applied to two additional microorganisms, both of which had previously been sequenced using Sanger sequencing to provide references against which the HGAP performance could be measured (Table 1A). *Meiothermus ruber* DSM1279 is a bacterium isolated from a hot spring (obtained from JGI) with a genome size of 3,097,457 bases and GC content of 63%. SMRT® sequencing of a ~10 kb insert library of genomic DNA from this organism was performed, running 4 SMRT® Cells in total. Table 1A compares the assembly results from two to four SMRT® Cells worth of data admitted to the assembler, showing that for three and four SMRT® Cells, single-contig, finished genomes were obtained as the uncurated output from HGAP. The dot-plots comparing the assemblies to the reference (FIG. 11) show that the assembly from four SMRT®Cells contains one mis-assembly caused by a 7,092 bp exact repeat. Interestingly, when applying the same method to data from 3 SMRT® Cells, the contig generated by the Celera® Assembler agrees with the reference, however, the beginning and the ending of the final single contig are broken at the other copy of the repeat. Apart from this mis-assembly caused by the 7.1 kb repeats, the assemblies cover the entire *M. ruber* genome and are at or greater than 99.999% concordant with the Sanger-based reference (nominal QV>50), and over 99% of all genes predicted correctly (Table 1A).

Figure 12:
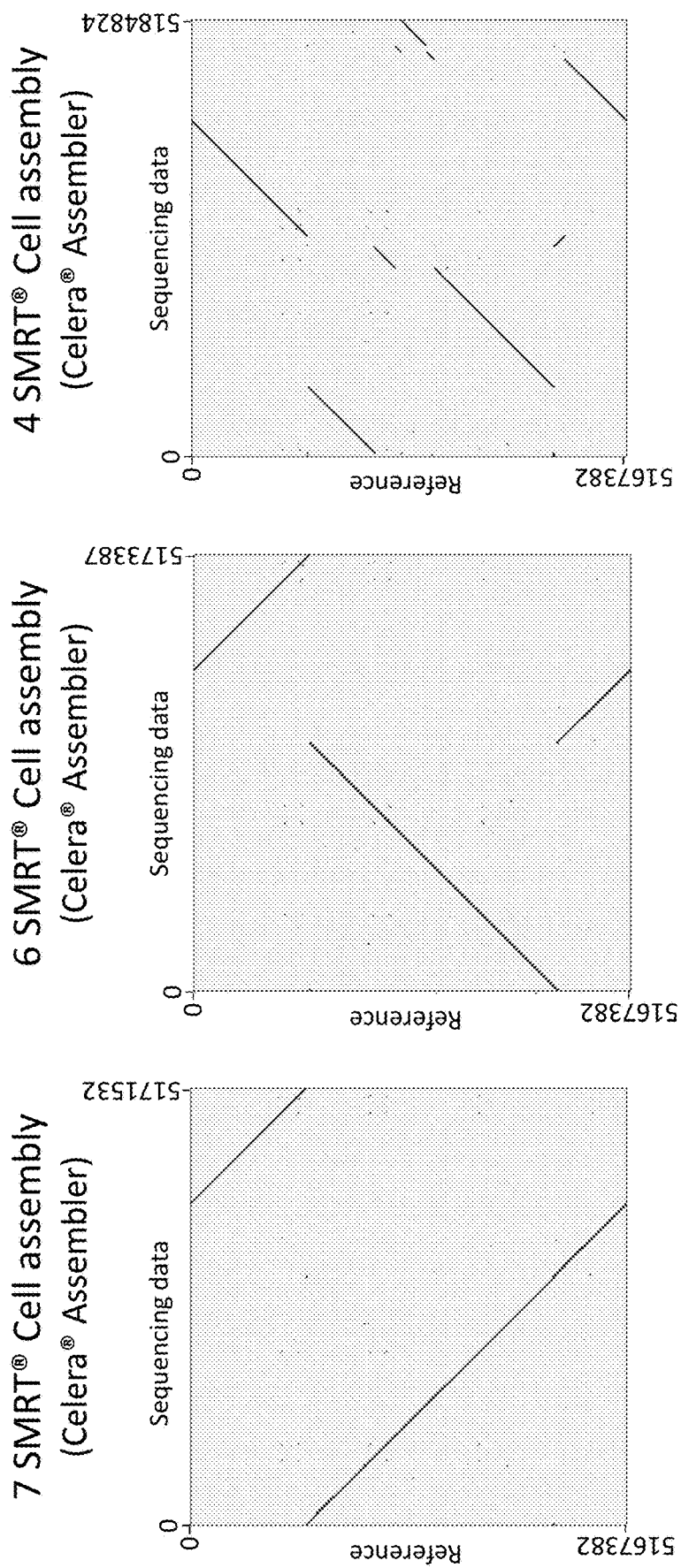
FIG. 12 shows comparisons of HGAP de novo assemblies against the Sanger reference for Pedobacter heparinus (NC_013061.1) for different numbers of SMRT® Cells used in the analysis.

The second microorganism subjected to SMRT® sequencing and HGAP was *Pedobacter heparinus* DSM 2366, a mesophilic bacterium with a genome size of ~5.1 Mb and GC content of 42% (obtained from JGI). Sequencing data from a total of 7 SMRT® cells of was generated, using data from four, six or all seven SMRT® cells in the HGAP workflow. For six and seven SMRT® cells, 2-contig assemblies which contain the entire genome were obtained, and are over 99.999% concordant with the reference (Table 1A, FIG. 12). Only one 6,139 bp long repeat was not sufficiently resolved in the assembly. As shown above for the cases of *E. coli* and *M. ruber*, >99% of the genes from these assemblies were successfully predicted.

Figure 13:
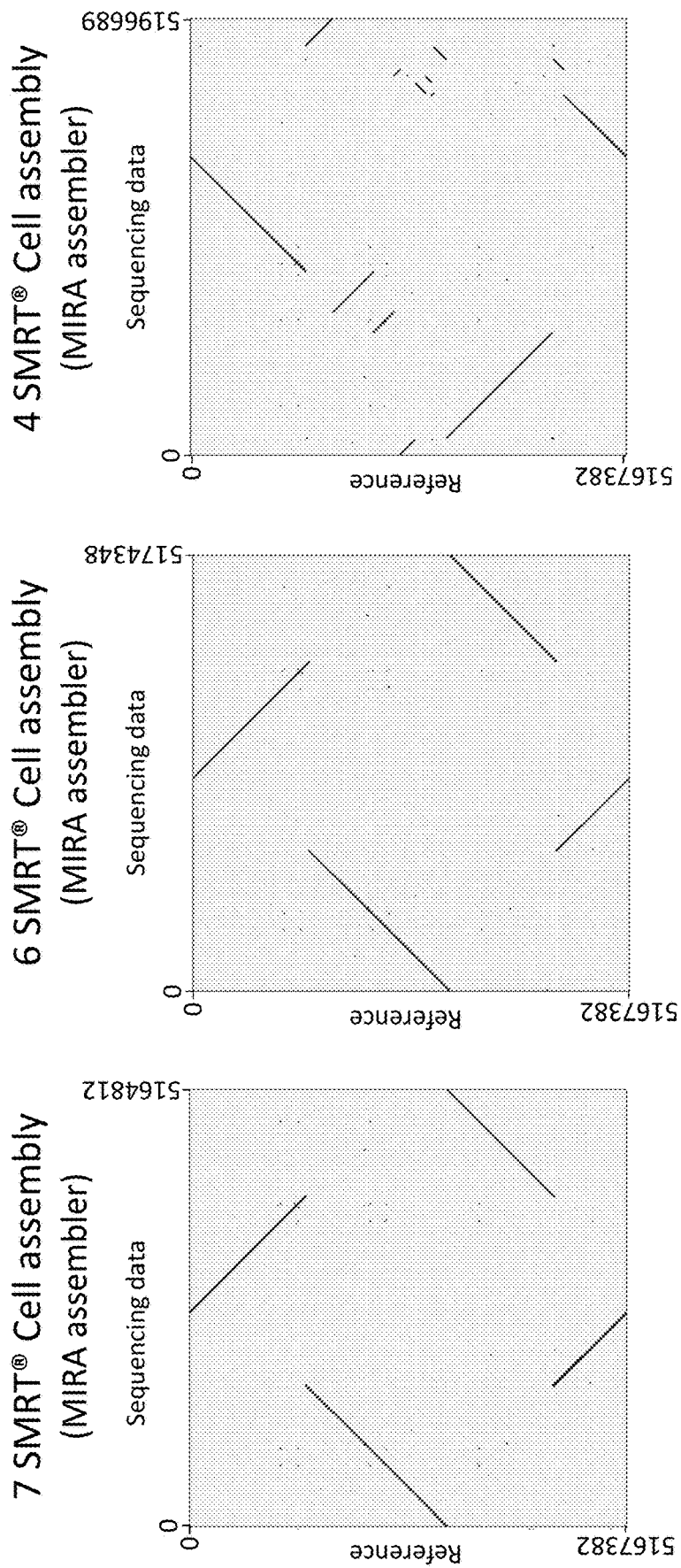
FIG. 13 shows comparisons of HGAP de novo assemblies against the Sanger reference for Pedobacter heparinus (NC_013061.1) using the MIRA assembler, for different numbers of SMRT® Cells used in the analysis.

To demonstrate the generality of applying PLRs to a variety of long-read capable assemblers, this genome was additionally assembled using the MIRA assembler, which is also capable of assembling sequence reads longer than a few kilobases. The result was compared to the assembly results from the Celera® Assembler (Table 1A; and Table 1B). The results from both assemblers were very similar, both in terms of genome contiguity and sequence accuracy. For the seven SMRT® Cell MIRA case, a single contig spanning the entire reference was obtained, however, the 6,139 bp repeat was likely not confidently resolved in this assembly (FIG. 13), analogous to the 3 SMRT® Cell assembly for *M. ruber* described hereinabove. The greedy nature of the heuristic algorithm optimized for speed in the layout stage of both CA and MIRA might not detect the inconsistent overlaps around the repeats to break contigs accordingly, especially in cases where the sequence read lengths are on the same order as the lengths of the long repeats. It is possible to investigate the underlying overlap information of the DNA fragments used by an assembler so that such mis-assembled contigs can be broken properly. The probability of such mis-assemblies will be reduced with longer read lengths, given reads spanning unique parts on both ends of a repeat region are generated.

Example 2

The utility of HGAP for other de novo assembly applications was also explored, including the efficient assembly of bacterial artificial chromosomes (BACs) which are typically several hundred kilobases in size. The construction and Sanger sequencing of BAC libraries has remained the major approach to resolve genomic regions with high repeat content and structural variation in complex genomes, including human (Liu, Alkan et al., 2009; Alkan, Coe et al., 2011; Ariyadasa and Stein 2012). For this demonstration, VMRC53-364D19, a ~175 kb BAC was chosen; it corresponds to a region on chromosome 15 (32, 291, 106-32, 463, 964) relative to the hg19 human reference sequence. A 8-10 kb SMRT® Bell™ template library made from the BAC DNA was subjected to a single SMRT® Cell of sequencing to obtain a correct and accurate BAC assembly using HGAP (Table 1A). From the initial 84.5 Mb of sequence, CLRs longer than 3,200 bases were chosen as the seed reads (corresponding to 11.8 Mb of total sequence). After the pre-assembly stage, 1,892 PLRs (5,027,597 bases total) with an average length of 2,657 bases were obtained. After assembly, 4 contigs of lengths 186,053 bp, 2,690 bp, 2,343 bp and 1,263 bp were obtained. The largest contig could be circularized and contained the targeted region and the BAC vector sequence; the smaller contigs were found to be small fragments of *E. coli* DNA sequences. In the final assembly, 165 SNPs relative to the hg19 reference sequence were observed. Six SNPs were selected and targeted PCR-Sanger sequencing was used to determine whether the observed SNPs represent biological variation or were due to sequencing errors. For the selected cases, all SNP calls from the assembly could be validated as correct base calls (Table 3).

TABLE 3

Single-nucleotide variants in the VMRC53-364D19 BAC assembly vs. the hg19 reference that were validated using PCR-Sanger sequencing.

| reference coordinate, chromosome 15 | variant |
|---|---|
| 32,394,062 | TDel |
| 32,364,043 | TDel |
| 32,310,527 | T > C |
| 32,387,828 | T > C |
| 32,340,851 | G > T |
| 32,338,206 | A > C |

The HGAP method has been applied to three microbial genomes and one human BAC. In each case, SMRT® sequencing of a single, large-insert template library to ~80-100x coverage followed by HGAP analysis resulted in excellent de novo genome assemblies. The new assembly algorithm described here simplifies the workflow from microbial DNA sample to finished genome considerably. In contrast to previously described, hybrid-technology based algorithms which required at least two separate sequencing libraries, sequencing runs and in certain implementations at least two different sequencing technologies (Bashir, Klammer et al. 2012; Koren, Schatz et al. 2012; Ribeiro, Przybylski et al. 2012), here only a single, long-insert shot-gun DNA library is prepared and subjected to automated, standard SMRT® sequencing.

While in the previously described hybrid assembly based approaches the shorter reads from long-insert SMRT® sequencing were discarded, the HGAP method described here uses every bit of such sequencing data: the long reads for assembling a contiguous, closed genome, and the shorter reads for improving the accuracy of the long reads through the pre-assembly process. Spurious, low-quality and chimeric reads are removed as early as possible in the overall genome assembly process and therefore do not contribute to artifactual contigs or mis-assemblies. The final consensus calling algorithm Quiver, which takes into account all of the underlying data and is aware of the raw quality values inherent to SMRT® sequencing, then polishes the assembly for final consensus accuracies in excess of 99.999% (QV50). The algorithm discards the original assembly sequence for consensus calling and thus avoids artifacts caused by reference bias.

Quiver can also be used for re-sequencing applications, i.e., when reads are mapped to a previously determined reference, as described hereinabove. Quiver generally improves the quality of the consensus sequence regardless of the sequencing coverage, and the effects can be even more striking in situations where only low coverage is available.

One prerequisite for obtaining finished, highly accurate genomes is the ability of a sequencing technology to generate high-quality sequence data over the entire range of sequence complexities and GC content present in that organism's genome. SMRT® sequencing has demonstrated excellent uniformity of sequence data over the widest range of GC content, including high-GC extremes at which other technologies, including even Sanger sequencing, fail (Loomis, Eid et al., 2012). Unbiased sequencing coverage allows for straightforward identification of any potential mis-assemblies or discordances with existing references which appear as breaks in the random, shotgun read structure (FIGS. 6A-6E). In addition, because the sample preparation in SMRT® sequencing does not include denaturation or amplification steps, palindromic sequences can be read successfully, whereas they typically cause so-called "hard stops" due to hairpin formation that is prohibitive in other sequencing systems (Zhang, Davenport et al. 2012).

The random error profile in SMRT® sequencing and lack of systematic bias results in very high consensus accuracies, as random errors wash out exponentially rapidly when building consensus (Koren, Schatz et al. 2012). While single-pass accuracies in SMRT® sequencing are lower compared to other sequencing technologies, the quality of the final genome sequence is determined in consensus. Systematic sequencing bias can introduce errors in the final genome sequence which cannot be overcome by additional sequencing coverage. In addition, the long read-lengths in SMRT® sequencing greatly facilitate the correct mapping of reads into repetitive regions by spanning the entire repeat units and anchoring the reads with unique flanking sequences. Difficulties around correctly mapping into repeat regions in genomes have been recognized as a source of errors in short-read sequencing technologies (Bashir, Klammer et al. 2012; Carneiro, Russ et al. 2012).

For smaller assembly targets such as BACs, given the overall throughput of greater than 100 Mb per SMRT® cell currently, it is likely that multiplex strategies to sequence pooled BACs could further enhance the efficiency of assemblies. Upon careful design of the sequencing run, one can potentially assemble all sequences at once if no long repeats between the different BACs in the pool are present, and proper assembly pre-processes, e.g. vector and *E. coli* contamination filtering, are included. Alternatively, barcoding strategies during library preparation could be employed.

The workflow described here is fully amenable to automation from DNA sample preparation to the determination of the finished genome, and has been completed in as few as 4 days. In addition, the same SMRT® sequencing reads can be exploited to determine the epi-genome of the organism under study (Murray, Clark et al. 2012). With further improvements with regards to read-length and overall sequencing throughput per SMRT® cell, a new paradigm of "one SMRT® Cell equals one de novo microbial genome and epigenome" can be envisioned. HGAP also has utility for the de novo assembly of eukaryotic genomes.

Example 3

Using CLEAR Assembly Process in a Genome Assembly

This example describes a process for assembly of *Plasmodium* 3D7 using pre-assembled reads, which are described elsewhere herein, using a "Consistent Long-read Evidence Assembling pRocess" (CLEAR). *Plasmodium* is a parasite that causes malaria. Its genome is challenging to sequence and assembly the genome, at least in part due to its high AT content (AT ~=80%). As such, most sequencing technologies cannot produce good and long sequences for assembling the genome into long contigs. Previous studies using second-generation sequencing technology only constructed contigs having N50 about 1 to 4 kb (BMC Genomics. 2011; 12: 116), and Sanger sequencing produced a contig N50 of about 10 to 20 kb. However, using a PacBio® RS for Single Molecule Real-Time (SMRT®) sequencing, the genome assembly produced was much better (N50 ~=954 kb) than the earlier sequencing results. The 3D7 strain was chosen because the DNA was readily available and it had a good finished reference sequence to which new assembly results could be compared.

A set of *Plasmodium* 3D7 sequencing data was generated using the PacBio® RS. The pre-assembly process described elsewhere herein converted the raw reads to preassembled reads. In a first step of the CLEAR process, the preassembled reads were aligned against each other using the BLASR algorithm to detect sequence overlaps between the preassembled reads. Next, a simple-asm code was used to generate the initial unitigs. Two utility functions were defined. The first takes the alignment information of a pair of reads and returns the alignment information of swapped query-target pair; and the second provides the reverse complement sequence. An Overlap class for creating objects to store the overlap information and related operations was defined, as was a SequenceFragment class for creating objects that store the sequence and overlapping information of a DNA fragment (sequence read).

A function get_contained_or_split_reads_from_m4 ( ) was defined that scanned through the BLASR m4 output and identified the reads that had split alignment, and the reads that were fully contained in other reads. Note that if a read had a unique sequence >500 bp in length at both the 3' and 5' ends, it wasn't classified as a "split" read. The m4 file was scanned twice. Only the split reads were identified during the first scan; the code identified the contained reads in the second scan. A query read was called as "contained" if the target was not a split read or if both query and target were split. The get_unique_ovlp_reads_from_m4 ( ) function scanned the BLASR m4 file again to constuct SequenceFragment objects and the associated alignment. The "contained" reads and "split" were excluded.

Construction of contigs began using the DNA read sequences and overlap data. Since the step following assembly comprises a final consensus sequence determination, e.g., using the Quiver algorithm, the process of constructing the contigs can be kept simpler by ignoring minor errors within the reads. get_path ( ) takes the read fragment data and an initial fragment identifier and the direction, 3' end or 5' end to extend, finds the best overlapped read from one end of the contig, and extends the contig. The extension ends when there is no un-used fragment appropriate for the best overlapped read. Two utility functions were defined for loading the sequence data into the SequenceFragment objects and outputting the split read fasta file. Calling the functions get_contained_or_split_reads_from_m4( ) and get_unique_ovlp_reads_from_m4 ( ) provided all necessary data for assembly. The split reads were output to a fasta file.

The overlapping information of each fragment was scanned. If a fragment only had 3' or 5' overlap, it was placed into the seeds list, which contains fragments used as "seeds" for constructing contigs by simple extension. These "seeds" were also sorted by the fragment length. The longest seeds were used to construct/extend constructs. To construct contigs, the method first went through all seed sequences and constructs contigs using the function get_path ( ). After that, it attempted to construct contigs using those reads that are not yet in any contigs. This way, all non-split and non-contained reads were used to construct contigs. The assembled utitigs were in asm.fa, and the assembly summary statistics revealed a pretty good N50=953.7 kb. The total size of the assembly was 23.3 Mb, which is very close to the reference sequence. There were no gaps. Only about 707/105869=0.668% of reads were classified as split. It was concluded that the simple logic approach to separate the "easy to assemble" portion of reads from the "difficult to assemble" portion was quite efficient, even in this difficult genome. Without being bound by theory, it is believed that in sequencing data having a large portion of longer reads, most of the overlapping of the reads is not confounded by shorter repeats. A large amount of the genome can be easily assembled using this method without worrying about those shorter repeats. In other words, it is quite possible to use a simple algorithm to get very good assembly when the reads are very long.

TABLE 4

|  | Scaffold Stats | Contig Stats |
|---|---|---|
| # Seqs | 487 | 487 |
| Min | 202 | 202 |
| $1^{st}$ Qu. | 466 | 466 |
| Median | 1180 | 1180 |
| Mean | 47981 | 47981 |
| $3^{rd}$ Qu. | 3456 | 3456 |
| Max | 1899581 | 1899581 |
| Total | 23367177 | 23367177 |
| n50 | 953696 | 953696 |
| n90 | 99851 | 99851 |
| n95 | 41702 | 41702 |

Figure 16:
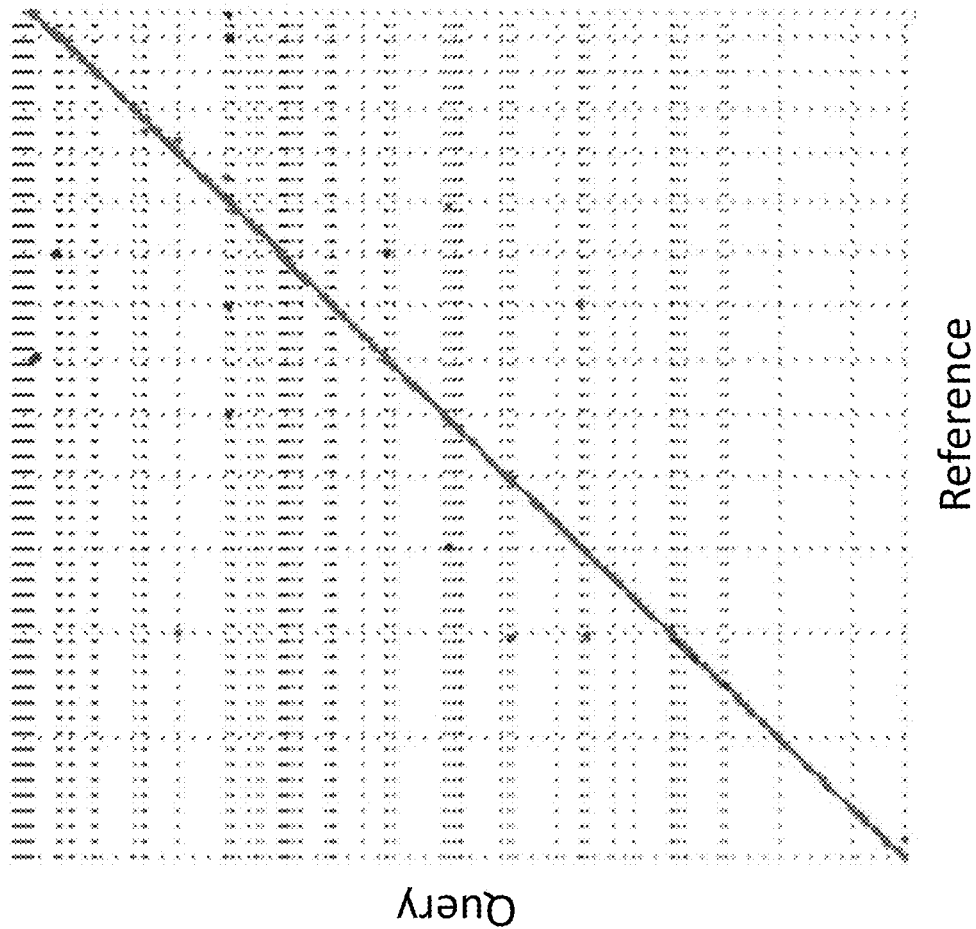
FIG. 16: Alignment for *Plasmodium* 3D7.

To compare these results to the *Plasmodium* 3D7 reference, nucmer was used to do a genome-wide alignment and mummerplot was used to compare the assembly from the alignment result. As one can see from the alignment shown as a dot plot in FIG. 16, the assembly was already very good in term of contiguity. The largest chromosome was basically covered by two contigs. At this stage, some additional data, e.g. fosmid ends or physical mapping, can be added for longer range information to improve the assembly and help resolve the order of the contigs, after which reads can be unambigiously placed back in the gaps. After the gap-filling step, the Quiver consensus algorithm is applied to get better accuracy at the end of the assembly process.

A more detailed description of contig scaffolding and simple gap filling to improve an assembly follows. In a pure de novo strategy, one would need some other information for scaffolding, e.g., physical mapping. The original *Plasmodium* 3D7 assembly (Gardner, et al. (2002) Nature 419:498-511, which is incorporated herein by reference in its entirety for all purposes) also used optical mapping data for scaffolding. Since optical mapping data was unavailable, the current *Plasmodium* 3D7 reference sequences were used as surrogates for physical mapping data to scaffold the previously determined contigs. The show-tiling command from mummer3 package was used to generate pseudo-chromosomes from the contigs.

The get_gap_flanking_seq.py script fetched the "gap ends" that were just the flanking sequences around the gaps. All the reads were aligned to those gap ends to identify the reads that can go across the gaps, which were subsequently filled in. The alignment information for gap filling was generated and the script simple_gapfill.py was used to fill in the gap using the p-reads. The assembly summary statistics before and after the gap-filling steps were compared and demonstrated that 60−33=27 gaps were filled by this process.

In order to generate the final consensus, the assembled contigs were put into the scaffolds, and un-assembled contigs and un-assembled p-reads and put together as the reference file for using Quiver to correct the residual errors. If this were not done, those reads that should have been mapped to un-assembled contigs could have been mapped to the scaffolds. This kind of wrong mapping can affect the final contig accuracy. A set of identifiers of the contigs that are in the scaffolds is generated using nucmer and show-coords, and the un-assembled contigs are put in the unassembled_ctg.fa file. Similarly, those split reads which are not fully aligned in scaffolds are identified. There were only 119 such partially aligned split reads. All contigs and un-assembled contigs/split reads were put into a file ready for guiding Quiver to generate the final consensus.

The summary statistics of the asm_draft_for_quiver.fa demonstrated that even including all the un-assembled contigs, the assembly summary statistics didn't change much since most of the un-assembled contigs were short.

TABLE 5

| Stats | Scaffold | Contig | Gap |
|---|---|---|---|
| # Seqs | 279 | 312 | 33 |
| Min | 1062 | 1062 | 619 |
| $1^{st}$ Qu. | 3562 | 3710 | 2698 |
| Median | 4949 | 5507 | 5671 |
| Mean | 87783 | 77420 | 10194 |
| $3^{rd}$ Qu. | 7704 | 8510 | 15888 |
| Max | 3269890 | 3269890 | 37013 |
| Total | 24491668 | 24155193 | 336409 |
| n50 | 1539341 | 1232996 | 16744 |
| n90 | 941854 | 90205 | 5099 |
| n95 | 9976 | 9544 | 2960 |

To check genome-wide alignment to the reference, a plot was generated using the asm_draft_for_quiver_ref.fa used as the reference template for Quiver. Instructions are provided on the PacBio® GitHub® website. GenomicConsensus/blob/master/doc/HowToQuiver.rst for using the original sequence reads and quality values to generate the best consensus result. This plot provided the alignment of the final consensus sequences (asm_final.fasta and asm_.fastq) to the PlasmoDB-9.2 Pfalciparum3D7_Genome.fasta reference sequences.

A comparison of the Quiver-polished alignments to the alignments before the Quiver consensus step demonstrates a reduced number of discrepancies. However, not surprisingly, the final assembly was not 100% identical to the reference assembly. Some of the discordances are believed to be biological and some of them are sequencing or assembly errors. One way to evaluate is to re-map the original reads back to the assembly and check the consistency of the assembly. The final assembly statistics summary is shown below. Notice that the final N50 is about 124 kb in contrast to the 1 kb to 20 kb contigs demonstrated in the earlier work using short-reads data from other platforms.

TABLE 6

| Stats | Scaffold | Contig | Gap |
|---|---|---|---|
| # Seqs | 279 | 312 | 33 |
| Min | 1065 | 1065 | 619 |
| $1^{st}$ Qu. | 3604 | 3727 | 2698 |
| Median | 4944 | 5532 | 5671 |
| Mean | 88444 | 78011 | 10194 |
| $3^{rd}$ Qu. | 7728 | 8527 | 15888 |
| Max | 3291950 | 3291950 | 37013 |
| Total | 24675916 | 24339441 | 336409 |
| n50 | 1551265 | 1241446 | 16744 |
| n90 | 950064 | 90998 | 5099 |
| n95 | 10021 | 9614 | 2960 |

Appendix 1

DAGCon: A Directed Acyclic Graph Based Consensus Algorithm

Described herein is an algorithm for constructing directed acyclic graph from existing pairwise alignments used for the pre-assembly step in the current implementation for the hierarchical genome assembly process. The algorithm presented herein is related to the method of representing multiple sequence alignment as a directed acyclic graph proposed by Lee (Lee et al., 2002). In this method, the input data is just a collection of sequences and the partial order alignment (POA) is constructed by aligning the POA graph to a new added sequence in each iteration. In the applications herein, a candidate or a reference sequence is usually known, and the goal is to identify differences between sequencing reads and the reference sequence. The alignments between the sequence reads and the reference are usually available from the earlier stages of the data processing pipeline by high performance alignment software to map the reads to the reference. Such alignment data between the reads and a reference is the input to the algorithm and is used to construct a directed acyclic graph denoted as the sequence alignment graph (SAG). A SAG summarizes all alignments from the reads to the reference sequence and is used to generate a consensus sequence that may be different from the reference.

Under the assumptions that (1) the majority of variants are substitutions and (2) the sequencing errors are usually mis-matches, a variant can be called by easily counting the read bases mapping a particular position in the reference sequence, and a consensus sequence can be constructed by using the variant call and the reference sequence. When the characteristic sequencing data does not satisfy the assumptions (1) and (2), e.g., when insertions and deletions instead of mis-matches become the dominant error mode, it is necessary to go beyond counting the mismatches of each reference base. Instead, a multiple sequence alignment (MSA) is constructed and used to call variants and build the consensus sequence. Complete optimized MSA construction is usually computationally expensive. Most MSA construction algorithms reported in the literature are mostly focusing on constructing a MSA within the context that there exist some evolution relations among the sequences (Edgar, 2004) (Larkin et al., 2007). This may not be applicable to DNA sequencing application where the differences among the reads are due to random independent errors caused by the sequencing reaction rather than some biological changes during the course of evolutionary history. It is therefore desirable to construct a MSA to reflect such property of the sequencing read data. For example, a consistency based multi-read alignment algorithm was developed for short read assembly by Rausch et al. (Rausch et al., (2009)). The construction of the SAG described herein uses only the alignments of the reads, and the references such that all reads are treated equivalently in constructing the MSA. This is more suitable for generating consensus where all reads should be treated equally.

Outline of the SAG Construction Algorithm

The input of the algorithm is the collections ($\{a_i, r_i\}|_{i=1...N}$, R) where $a_i$ is the alignment of a read $r_i$ to a reference sequence R. The output is a graph G={V,E} where V is the nodes labeled by the DNA bases A, C, G or T and E are the edges that represent the connection of the consecutive bases in the reads. Each read can be represented as a unique path in graph $g_r=\{v_r, e_r\}$. Each node has an associated set of reads $r_v=\{r|v\in g_r\}$ that pass through it. Each edge also has an associated set $r_e=\{r|e\in g_r\}$ of reads that pass through it.

Here is an outline of the algorithm for constructing the SAG

Figure 17:
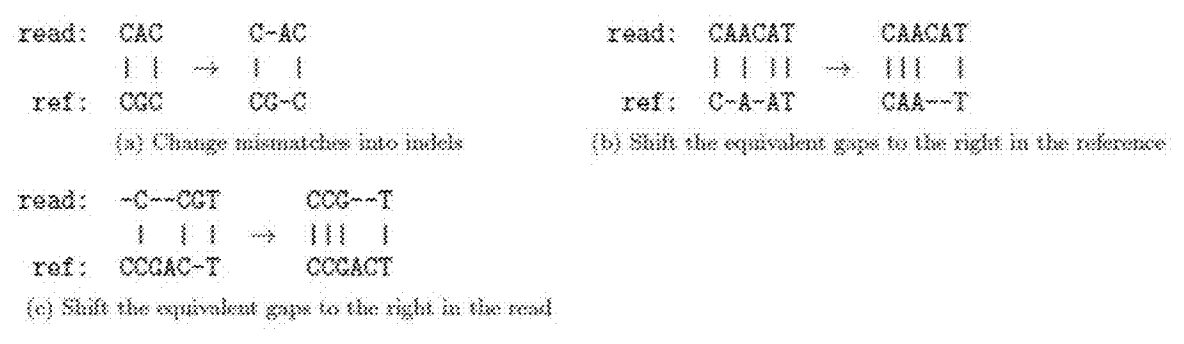

1. Normalize mismatches and degenerated alignment positions as shown in FIG. 17.

Figure 14:
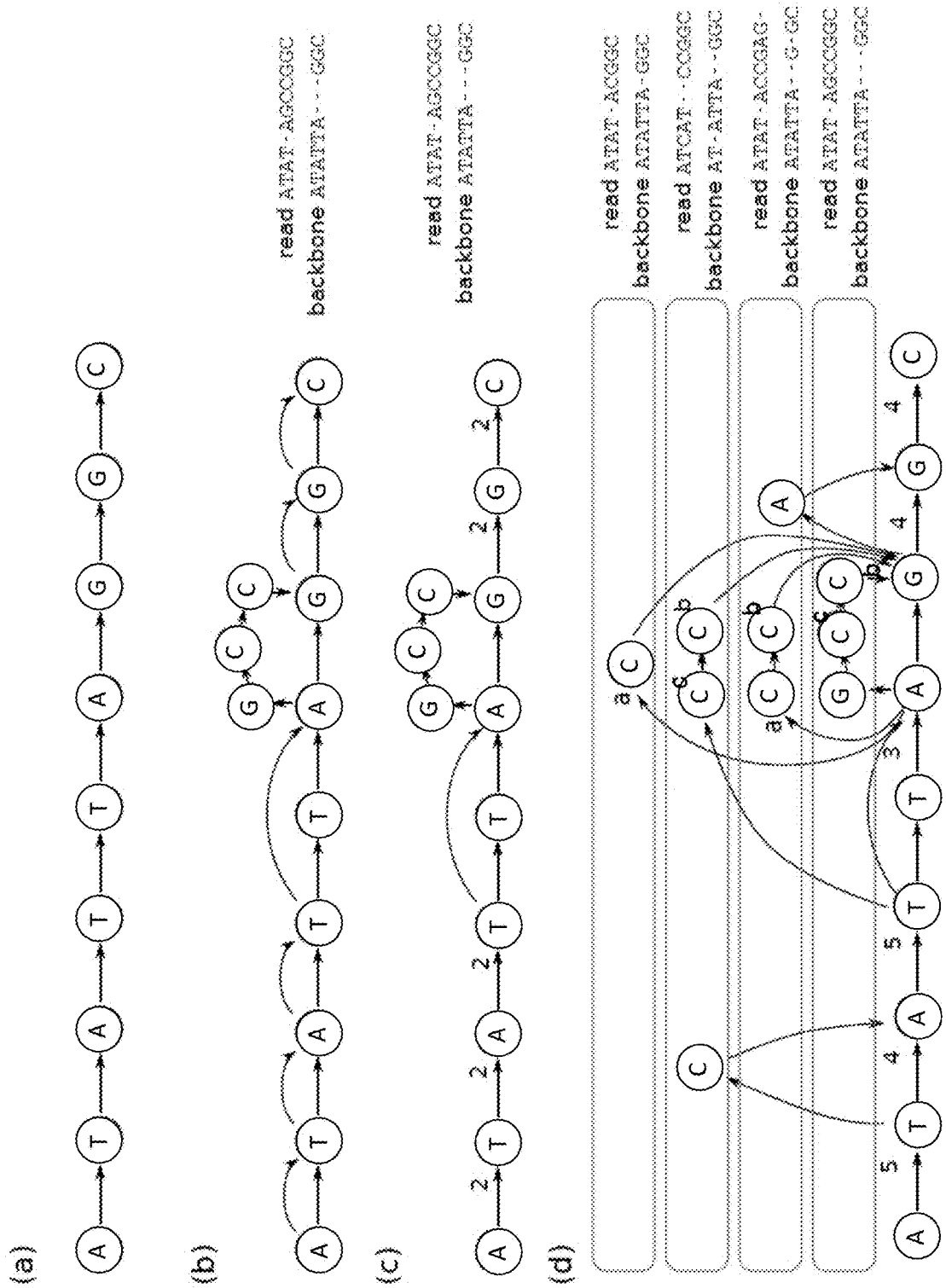
FIG. 14 shows: (a) A backbone linear graph $G_B$. The special nodes "Begin" and "End" are not shown. (b) The sequence alignment graph before the edges are merged when the first alignment is added to the group. (c) The intermediate sequence alignment graph GI after the first alignment is added. The numbers on those directed edges indicate the number of "reads" (including the backbone) that pass through them. (d) The intermediate sequence alignment graph GI after the 4 alignments are added. The initial pairwise alignments between the reads to the backbone reference sequence are shown on the right. The nodes labelled with 'a', 'b', and 'c' can be further merged according the merging rules. (e) The final sequence alignment graph GS after node merging. (f) The consensus path of GS is highlighted with the thicker directed edges and the thicker circles.
Figure 14:
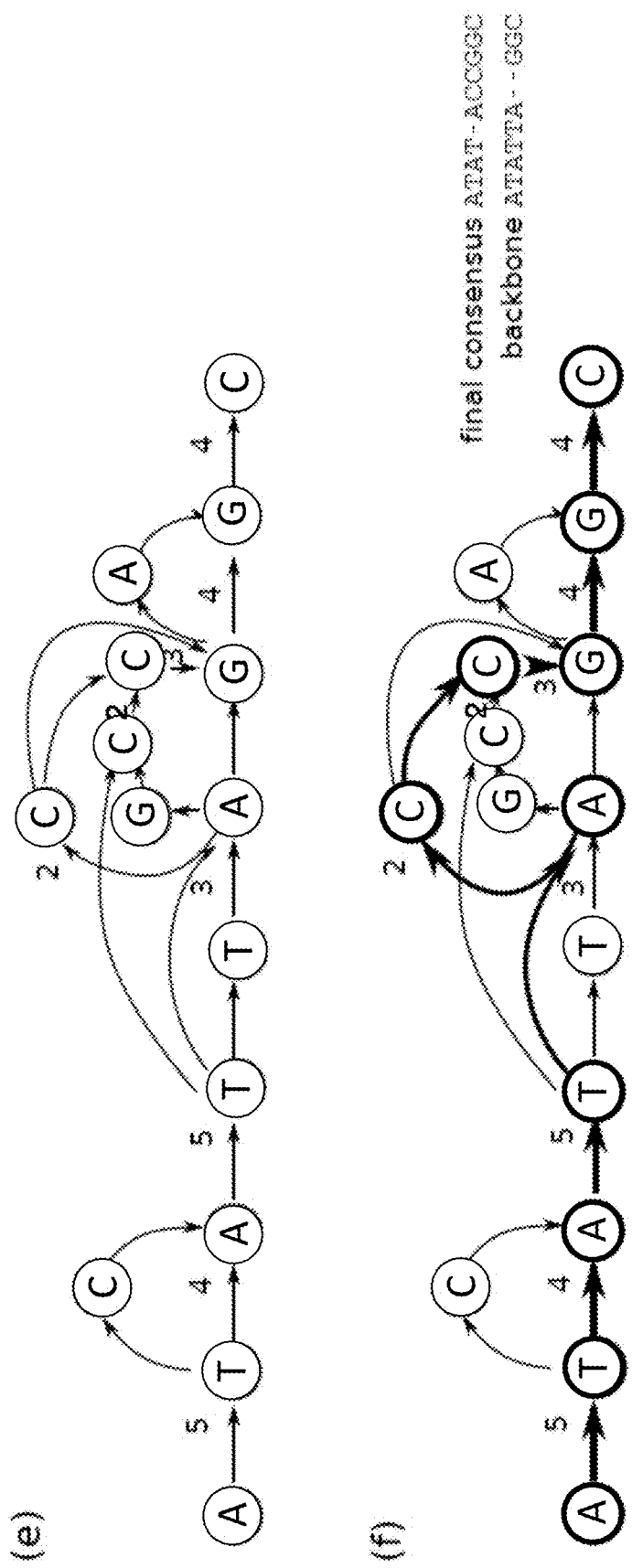

2. Setup an initial graph from the reference sequence as shown in FIG. 14(a).
3. Construct a multigraph (a graph that permits multiple edges connecting the same two nodes) from the alignments and merge the edges that are connecting the same nodes as shown in FIGS. 14(b) to 14(d).
4. According to the topological order of the node in the graph, systematically (1) merge nodes that have the same label and are connected to the same node and (2) merge nodes that have the same label and are connected from the same node as shown in FIGS. 14(d) to 14(f).

Normalize Mismatches and Degenerated Alignment Positions

When representing an alignment as a directed graph, each node only has one label which is the base that aligned with the node. Mismatches between two sequences are indistinguishable from a nearby insertion-deletion pair. To simplify the construction of the sequence alignment graph (SAG), one can convert all mis-matches to local insertion-deletion pairs in the alignment. Moreover, there are cases where there are multiple ways to place gaps in an alignment as shown in FIG. 17. As an optional step, to ensure getting consistent results of the SAG, the alignment is normalized by moving all gaps to the right most equivalent positions as shown in FIG. 17. One reason for normalizing the gap placement in the alignments is to take into account somewhat arbitrary rules for resolving alignment degeneracy reported by an aligner. For example, if a read is aligned in a reversed orientation first, the result could be different from aligning the read in the forward direction and then reverse the final alignment string after the alignment process. A procedure to normalize the placement of the gaps will reduce such potential inconsistency and improve the final consensus accuracy.

Setup an Initial Graph from the Reference Sequence

The first step to construct an alignment graph is to use the reference sequence to build a backbone linear graph GB that simply connects each base in the reference within two special nodes: "Begin" and "End" nodes. Namely the initial backbone graph consists of the nodes (1) $v_i$ for $i\in[0, |R|-1]$, $v_B$, and $v_E$ where label $(v_i)=R_i$ where $R_i$ indicates the base label of the reference at position i and the edges $e_{i,j}$: $v_i \rightarrow v_{j=i+1}$ for $i\in[0, |R|-2]$, $e_{B0}$: $v_B \rightarrow v0$ and $\theta_{|R|-1,E}$: $v_{|R|-1} \rightarrow v_E$.

Construct the Multigraph from the Alignments and Merge the Edges

Conceptually, the multigraph is constructed iteratively when a new alignment represents a list of pair of bases and indel symbol $A=\{(q_i, q_i)|q_i, r_i \in A, C, G, T, -\}$ is added into the graph. A scan through each alignment position between a read and the reference is carried out, starting from the vB node as the initial node. When there is a match between the read and the reference, the previous node is connected to the reference node in the backbone graph. If there is an insertion in the read, a new node labelled by the read base is created, and a new edge pointing from the previous node to the new node is created. Once all alignments are added, all edges that are connecting the same two nodes into a single edge are merged to convert the multigraph into a regular graph. In fact, the merge step can be integrated at the time when the alignment is added. The pseudo-code for constructing the intermediate graph $G_I=(V_I, E_I)$ is listed in Algorithm 1 (FIG. 19).

Merge Nodes

The next step to reduce the complexity of GI is to find those nodes which are similar to each other in a local context and merge them in a way that preserves the directed acyclic property of the graph. This is also analogous to a greedy local alignment for the reads with the same base from them before and after an alignment node. The general idea of the algorithm to generate the final sequence alignment graph $G_S=(V_S, E_E)$ is to define an order to go through the graph and merge the nodes according to their labels and connection to the other nodes. For example, all nodes labeled by the same label are merged and are connected to the same out-node, and also all nodes with the same label that are connected from the same in-node are merged. The algorithm presented here is based on a variant of the topological sorting algorithm. The pseudocode is listed as Algorithms 2, 3, 4 (FIGS. 20-22, respectively). An example of showing the process is shown in FIG. 14(d) to (f).

Generate Consensus Sequence from $G_S$

The consensus algorithm is listed in Algorithm 5 and 6 (FIGS. 23 and 24). The basic idea for generating a consensus is (1) assigning a score for each node and (2) find a path that maximizes the sum of the score of the nodes in the path. Here the score of a node is calculated by checking the weight of the all out-edges of the node. If an edge takes more than half of the local coverage (which is equal to the maximum weight that an edge can have around the node), it gets a positive score. Otherwise, it gets a negative score. The score of any path in the graph is simply defined as the sum of the scores of the nodes in the path. The consensus is then built by finding the path that has the maximum path score in all possible paths. Since the graph is directed acyclic, such path can be found by simple dynamic programming and backtracking. The algorithms shown in Algorithms 5 and 6 (FIGS. 23 and 24) perform the topological sorting and calculate the best score and the best edge of each node at the same time. Additionally, backtracking is done to construct the best consensus path in the group.

Such consensus algorithm is typically "biased" toward to the reference used in the alignment. If the real sample sequences have high variation from the reference sequence, then there will be opportunity for further improvement from the single-pass consensus algorithm. One way to improve it is to use an iterative process to increase the final quality of the consensus sequence. Namely, one can take the consensus sequence as the reference sequence and align the reads back to the first iteration of the consensus sequence and repeatedly apply the consensus algorithm to generate the next iteration of the consensus sequences. Such iteration process can reconstruct the regions that are very different from the original reference, although it is generally more computationally intensive. The other possible strategy is to identify the high variation region, then, rather than using the original reference, one uses one of the reads as the reference to reconstruct those regions to avoid the "bias" toward the original reference.

Using DAGCon Algorithm to Generate Pre-Assembled Long Reads

All subreads are first mapped to the long seeding set using BLASR. The target seeding sequences are split into chunks for mapping other reads to them in parallel. In such case, the following BLASR options for mapping can be used: "-nCandidates 50-minMatch 12-maxLCPLength 15-bestn 5-minPctIdentity 70.0-maxScore-1000-m 4". After mapping, the BLASR output files are parsed for each chunk and top 12 hits are selected for each query reads as default. The number of top hits could impact the quality of the pre-assembly reads and the ability to resolve very similar repeats.

For each seed read, all the subreads are collected, and aligned to it from the alignment output of the BLASR program. Each subread is trimmed according to the alignment coordinates. For example, if BLASR reports base s1 to s2 are aligned to the seed read, base s1+Δ to s2−Δ will be used for pre-assembly. The value of Δ is to be 100 since the BLASR aligner sometimes generates poor alignment at the ends such that chimera reads might still have good coverage across the chimeric junction. More aggressive trimming with a larger Δ will help to remove all chimeric reads at a cost losing useful bases. One can avoid losing bases by choosing smaller Δ.

The trimmed subreads are then used with the seed read to generate the pre-assembled long read with the DAGCon algorithm described in the previous section.

Appendix 2

Quiver Consensus Algorithm

The Quiver algorithm was originally developed for Pacific Biosciences Circular Consensus Sequencing (CCS) analysis mode, and is now available for multimolecule consensus analyses. With coverage levels of 60×, it has been found that Quiver has reliably achieved accuracies exceeding Q50 (99.999%) in a number of de novo assembly projects. We describe the details of the Quiver algorithm below. An outline of the algorithm is as follows.

Given a vector of reads R from a single (unknown) template T, Quiver uses a greedy algorithm to maximize the likelihood Pr (R|T) for the unknown T. A likelihood function Pr (R|T) has been developed which encodes the sequencing error model and is specific to a particular sequencing chemistry and enzyme. The parameters within the model are derived using a training step that learns an error model from SMRT® sequencing data on a known template. This can be accomplished by one skilled in the art.

For a long reference, the consensus is processed with tiling windows across the reference to limit the amount of memory used. Here is an outline of the QuiverConsensus algorithm for reference window W:

1. Use reference alignment to identify reads $R=\{R_1, R_2, \ldots, R_k\}$ corresponding to W 2. Create a candidate template sequence using $\tilde{T}_1 \leftarrow$POAConsensus(R). (The original reference is not used as the candidate template sequence.)

3. Repeat until convergence:

$$\tilde{T}_{s+1} \leftarrow \tilde{T}_s + \{\text{single base mutations } \mu | Pr(R|\tilde{T}_s+\mu) \geq Pr(R|\tilde{T}_s)\}$$

The single base mutations applied are all possible single-base substitutions, insertions, and deletions.

Pulse Metrics

In addition to basecalls, the basecaller software includes metrics reflecting its confidence against the various types of errors. The pulse metrics, or QV features, are encoded using the standard Phred-scaling convention, $QV=-10 \log_{10} p_{error}$.

The pulse metrics in use are as follows:

1. InsertionQV, SubstitutionQV: Probability that this base call is actually an insertion (substitution) relative to the true template.

2. DeletionQV: Probability that the basecaller omitted a base relative to the true template, prior to this basecall. The maximum likelihood missed base is encoded (as an ASCII character) in the DeletionTag feature.

3. MergeQV: Probability that the basecaller merged together two identical adjacent template bases into this basecall.

Computing the Template Likelihood Function

Reads are assumed independent, so the template likelihood function, Pr(R|T) is given by:

$$Pr(R \mid T) = \prod_{k=1}^{K} Pr(R_k \mid T).$$

In typical reads, indel errors are the dominant mode, so the model needs to consider the possible alignments—the ways T can be construed to have generated $R_k$:

$$Pr(R_k \mid T) = \sum_{A} Pr(R_k \mid T, A),$$

where A represents the alignment between the read and template sequences. This summation can be computed efficiently using a standard Sum-Product dynamic programming approach. In practice the Viterbi algorithm, which maximizes over the unknown alignment A rather than summing, is used. Experience has shown the Viterbi algorithm to be substantially more computationally efficient than other possible algorithms, but with little impact on accuracy.

Outline of Dynamic Programming

The Sum-Product recursions build up the forward matrix A and backward matrix B of probabilities defined by $A_{ij}$ =marginal prob. of an alignment of $R[0 \ldots (i-1)]$ to $T[0 \ldots (j-1)]$, and     (1)

$B_{ij}$ =marginal prob. of an alignment of $R[i:I-1]$ to $T[j:J-1]$     (2)

where $S[p \ldots r]$ denotes the substring $S_p S_p+1 \ldots S_r$.

The recursions are computed as $A_{ij} = \Sigma_{m(i'j') \to (ij)}(A_{i'j'} \times \text{moveScore}(m))$, and     (3)

$B_{ij} = \Sigma_{m(ij) \to (i'j')}(\text{moveScore}(m) \times B_{i'j'})$,     (4)

For the Viterbi algorithm, replace marginal by maximum and sum by max in the above definitions.

Alignment Moves

Figure 18:
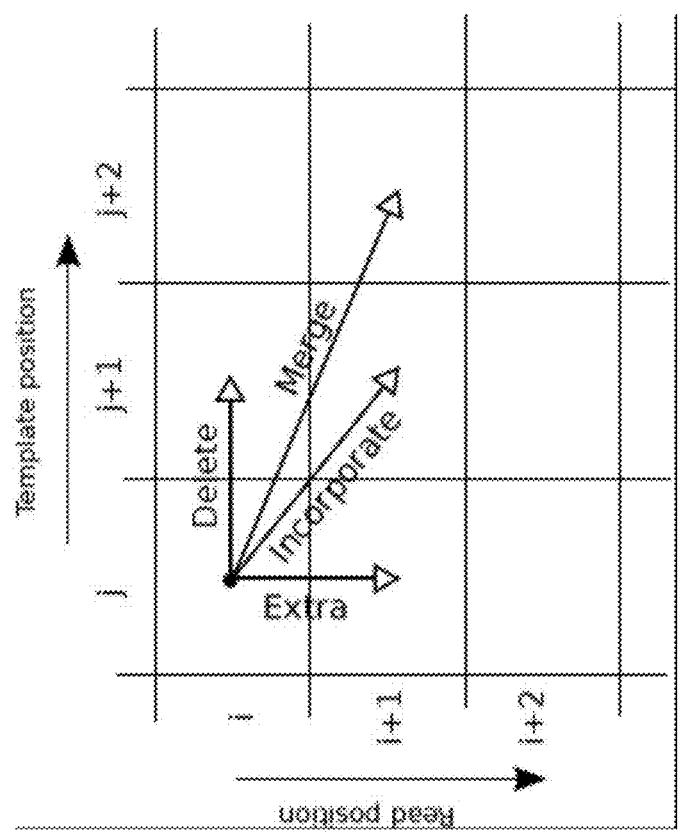
FIG. 18: The alignment moves available in Quiver's probability model Pr(R|T).
In addition to the standard Smith-Waterman moves, a Merge move is used to model the process of pulse merging in homopolymer regions.

The moves m considered in the above alignment recursions are the familiar Smith-Waterman alignment moves Incorporate, Delete, and Extra, and additionally a Merge move that is only available when $T[j]=T[j-1]$. The Merge move allows modelling the pulse merging process independently from the spontaneous deletion process; the addition of this move has consistently shown improved accuracy results in use of the algorithm. These are shown schematically in FIG. 18.

Efficiently Computing $Pr(R_k \mid T+\mu)$

The main loop of Quiver requires testing the likelihood of all possible single-base point mutations to a template. A single base mutation $\mu$ to a template sequence T is represented as $T+\mu$. It is essential to be able to compute $Pr(R_k \mid T+\mu)$ very rapidly, given the A and B matrices used to compute $Pr(R_k \mid T)$. To do so, the "forward-backward trick" is exploited, which in the notation herein amounts to the identity:

$Pr(R \mid T) = A_{ij} = B_{00} = \max_{m(i'j') \to (ij)} A_{ij} \times B_{ij}$, for any $j$,     (5)

so that the likelihood can be computed directly from two consecutive columns of the A matrix and the following column of the B matrix. Modification of the template via a single base substitution $\mu$ at position j induces new forward-backward matrices A' and B', where only columns $\{j+1, \ldots, J\}$ of A and A', and columns $\{0, 1, \ldots, j\}$ of B and B' disagree. To compute $Pr(R \mid T+\mu)$, it is therefore needed only to compute columns j+1 and j+2 of A', and use them together with column j+3 of B' (which can be taken directly from B) in Equation 5 to compute the likelihood. An analogous calculation is performed in the case of insertions and deletions.

Using this optimization, computing the likelihood for each single-base point mutation requires O(L) time and space, naively, where we use L to denote the template length. Using the further banding optimization described below, the space and time requirements are both reduced to O(1).

Banding Optimization

To reduce the computational time and storage requirements to manageable levels, the dynamic programming algorithm is approximated using a banding heuristic. In short, rather than computing full columns of the forward and backward matrices, only a narrow band of high-scoring rows within each column is computed. This approach is commonplace in modern aligners. Adopting this heuristic reduces the runtime for the initial computation of A and B to O(L) (down from $O(L^2)$, without banding), and the runtime for computing a mutation score to O(1) (from O(L), without banding).

Since only a band of each column is computed, it is natural to avoid storing the entire column as well. Only the high scoring bands of A and B are stored, reducing their storage requirement from $O(L^2)$ to O(L). Given that the typical template span we consider in Quiver is ~1,000 bp, these optimizations yield massive performance improvements.

It is to be understood that the foregoing description is intended to be illustrative and not restrictive. It is not intended that the examples presented herein limit the scope of the appended claims. It should be readily apparent to one skilled in the art that various modifications may be made to the invention disclosed herein without departing from the scope and spirit of the invention. The scope of the invention should, therefore, be determined not with reference to the above description, but should instead be determined with reference to the appended claims, along with the full scope of equivalents to which such claims are entitled.

LIST OF PUBLICATIONS

Alkan, C., Coe, B. P., et al. (2011). "Genome structural variation discovery and genotyping." *Nat. Rev. Genet.* 12(5): 363-76.

Ariyadasa, R. and N. Stein (2012). "Advances in BAC-based physical mapping and map integration strategies in plants." *J. Biomed. Biotechnol.* 2012: 184854.

Bashir, A., A. A. Klammer, et al. (2012). "A hybrid approach for the automated finishing of bacterial genomes." *Nat. Biotechnol.* 30(7): 701-7.

Blattner, F. R., G. Plunkett, 3rd, et al. (1997). "The complete genome sequence of *Escherichia coli* K-12." *Science* 277(5331): 1453-62.

Carneiro, M. O., C. Russ, et al. (2012). "Pacific biosciences sequencing technology for genotyping and variation discovery in human data." *BMC Genomics* 13: 375.

Chaisson, M. J. and G. Tesler (2012). "Mapping single molecule sequencing reads using Basic Local Alignment with Successive Refinement (BLASR): Theory and Application." *BMC Bioinformatics* 13(1): 238.

Eid, J., A. Fehr, et al. (2009). "Real-time DNA sequencing from single polymerase molecules." *Science* 323(5910): 133-138.

English, et al. (2012). "Mind the Gap: Upgrading Genomes with Pacific Biosciences RS Long-Read Sequencing Technology." *PLoS One* 7(11): e47768.

Fraser, C. M., J. A. Eisen, et al. (2002). "The value of complete microbial genome sequencing (you get what you pay for)." *J. Bacteriol.* 184(23): 6403-5; discussion 6405.

Gagarinova, A. and A. Emili (2012). "Genome-scale genetic manipulation methods for exploring bacterial molecular biology." *Mol. Biosyst.* 8(6): 1626-38.

Huang, X. (1996). "An improved sequence assembly program." *Genomics* 33(1): 21-31.

Kelley, D. R., M. C. Schatz, et al. (2010). "Quake: quality-aware detection and correction of sequencing errors." *Genome Biol.* 11(11): R116.

Kingsford, C., M. C. Schatz, et al. (2010). "Assembly complexity of prokaryotic genomes using short reads." *BMC Bioinformatics* 11: 21.

Koren, S., M. C. Schatz, et al. (2012). "Hybrid error correction and de novo assembly of single-molecule sequencing reads." *Nat. Biotechnol.* 30(7): 693-700.

Korlach, J., K. P. Bjornson, et al. (2010). "Real-time DNA sequencing from single polymerase molecules." *Methods Enzymol.* 472: 431-455.

Krumsiek, J., R. Arnold, et al. (2007). "Gepard: a rapid and sensitive tool for creating dotplots on genome scale." *Bioinformatics* 23(8): 1026-8.

Kurtz, S., A. Phillippy, et al. (2004). "Versatile and open software for comparing large genomes." *Genome Biol.* 5(2): R12.

Lander, E. S, and M. S. Waterman (1988). "Genomic mapping by fingerprinting random clones: a mathematical analysis." *Genomics* 2(3): 231-9.

Lee, C., C. Grasso, et al. (2002). "Multiple sequence alignment using partial order graphs." *Bioinformatics* 18(3): 452-464.

Liu, G. E., C. Alkan, et al. (2009). "Comparative analysis of Alu repeats in primate genomes." *Genome Res.* 19(5): 876-85.

Loman, et al. (2012). "High-throughput bacterial genome sequencing: an embarrassment of choice, a world of opportunity." *Nat. Rev. Microbiol.* 10(9): 599-606.

Loomis, E. W., J. S. Eid, et al. (2013). "Sequencing the unsequenceable: Expanded CGG-repeat alleles of the fragile X gene." *Genome Res.* 23 (1), 121-8.

Medini, D., D. Serruto, et al. (2008). "Microbiology in the post-genomic era." *Nat. Rev. Microbiol.* 6(6): 419-30.

Milne, I., M. Bayer, et al. (2010). "Tablet—next generation sequence assembly visualization." *Bioinformatics* 26(3): 401-2.

Murray, I. A., T. A. Clark, et al. (2012). "The methylomes of six bacteria." *Nucleic Acids Res.,* 40(22), 11450-62.

Myers, E. W., G. G. Sutton, et al. (2000). "A whole-genome assembly of *Drosophila.*" *Science* 287(5461): 2196-204.

Parkhill, J. and B. W. Wren (2011). "Bacterial epidemiology and biology—lessons from genome sequencing." *Genome Biol.* 12(10): 230.

Rasko, D. A., D. R. Webster, et al. (2011). "Origins of the *E. coli* strain causing an outbreak of hemolytic-uremic syndrome in Germany." *N. Engl. J. Med.* 365(8): 709-17.

Ribeiro, F. J., D. Przybylski, et al. (2012). "Finished bacterial genomes from shotgun sequence data." *Genome Res.* 22(11): 2270-7.

Ricker, N., H. Qian, et al. (2012). "The limitations of draft assemblies for understanding prokaryotic adaptation and evolution." *Genomics* 100(3): 167-75.

Salzberg, S. L., A. M. Phillippy, et al. (2012). "GAGE: A critical evaluation of genome assemblies and assembly algorithms." *Genome Res.* 22(3): 557-67.

Schatz, M. C., A. L. Delcher, et al. (2010). "Assembly of large genomes using second-generation sequencing." *Genome Res.* 20(9): 1165-1173.

Siguier, P., J. Filee, et al. (2006). "Insertion sequences in prokaryotic genomes." *Curr. Opin. Microbiol.* 9(5): 526-31.

Sommer, D. D., A. L. Delcher, et al. (2007). "Minimus: a fast, lightweight genome assembler." *BMC Bioinformatics* 8: 64.

Srikhanta, Y. N., K. L. Fox, et al. (2010). "The phasevarion: phase variation of type III DNA methyltransferases controls coordinated switching in multiple genes." *Nat. Rev. Microbiol.* 8(3): 196-206.

Toussaint, A. and M. Chandler (2012). "Prokaryote genome fluidity: toward a system approach of the mobilome." *Methods Mol. Biol.* 804: 57-80.

Treangen, T. J., D. D. Sommer, et al. (2011). "Next generation sequence assembly with AMOS." Curr. Protoc. *Bioinformatics* Chapter 11: Unit 11 8.

Zhang, X., K. W. Davenport, et al. (2012). "Improving genome assemblies by sequencing PCR products with PacBio." *Biotechniques* 53(1): 61-2.

[Edgar, 2004] Edgar, R. C. (2004). MUSCLE: multiple sequence alignment with high accuracy and high throughput. *Nucleic Acids Research* 32, 1792-1797.

[Hyatt et al., 2010] Hyatt, D., Chen, G.-L., LoCascio, P., Land, M., Larimer, F. and Hauser, L. (2010). Prodigal: prokaryotic gene recognition and translation initiation site identification. *BMC Bioinformatics* 11, 119.

[Larkin et al., 2007] Larkin, M., Blackshields, G., Brown, N., Chenna, R., McGettigan, P., McWilliam, H., Valentin, F., Wallace, I., Wilm, A., Lopez, R., Thompson, J., Gibson, T. and Higgins, D. (2007). Clustal W and Clustal X version 2.0. *Bioinformatics* 23, 2947-2948.

[Lee et al., 2002] Lee, C., Grasso, C., and Sharlow, M. F. (2002). Multiple sequence alignment using partial order graphs. *Bioinformatics* 18, 452-464.

[Rausch et al., 2009] Rausch, T., Koren, S., Denisov, G., Weese, D., Emde, A.-K., Dring, A. and Reinert, K. (2009). A consistency-based consensus algorithm for de novo and reference-guided sequence assembly of short reads. *Bioinformatics* 25, 1118-1124.

Throughout the disclosure, various references, patents, patent applications, and publications are cited. Unless otherwise indicated, or to the extent not already expressly incorporated herein, each is hereby incorporated by reference in its entirety for all purposes. All publications mentioned herein are cited for the purpose of describing and disclosing reagents, methodologies and concepts that may be used in connection with the present invention. Nothing herein is to be construed as an admission that these references are prior art in relation to the inventions described herein.

What is claimed:

1. A method of identifying a sequence of a nucleic acid by at least one software component executing on a processor, the method comprising:

receiving, by the processor, a set of reads for the nucleic acid sequence wherein the reads have an average length (L) of at least 0.5 kb in length and wherein the set of reads collectively encompass at least 3 megabase pairs of the nucleic acid;

selecting, by the processor, a plurality of seed reads from the set of reads by applying a predetermined length cutoff $l_{cutoff}$ to the set of reads, wherein the $l_{cutoff}$ is at least 1 kb;

aligning, by the processor, each read in the set of reads to one or more seed reads in the plurality of seed reads, thereby producing a mini-assembly for each seed read that comprises a subset of the set of reads, and thereby forming a plurality of mini-assemblies;

creating, by the processor, a respective pre-assembled read for each respective mini-assembly in the plurality of mini-assemblies by discarding those portions of the respective mini-assembly that do not exhibit a minimum coverage with respect to the nucleic acid and by removing one or more insertion errors in the subset of reads of the mini-assembly thereby generating a set of pre-assembled reads;

using, by the processor, a sequence assembler to assemble the set of pre-assembled reads into one or more contigs for the nucleic acid; and generating, by the processor, a consensus sequence of the nucleic acid using the one or more contigs, wherein the consensus sequence of the nucleic acid is at least 3 megabase pairs in length.

2. The method of claim 1, wherein the creating further comprises optimizing each pre-assembled read to produce a set of refined pre-assembled reads prior to using the sequence assembler.

3. The method of claim 1, wherein the creating further comprises trimming alignments of the reads to the seed reads, thereby reducing chimeric reads and read noise in the set of pre-assembled reads prior to using the sequence assembler.

4. The method of claim 1, wherein the reads in the set of reads have an average accuracy of between 80 and 95% relative to corresponding portions of a reference sequence for the nucleic acid.

5. The method of claim 1, wherein the $l_{cutoff}$ is at least 2 kb.

6. The method of claim 1, wherein the $l_{cutoff}$ is between 1,000 bp and 10,000 bp.

7. The method of claim 1, wherein each mini-assembly in the plurality of mini-assemblies exhibits 15×-20× coverage of corresponding portions of the nucleic acid.

8. The method of claim 1, wherein the generating a consensus sequence of the nucleic acid comprises:
   a) aligning each sequence in the set of original reads to a contig in the one or more contigs to produce a set of sequence alignments;
   b) using the set of sequence alignments to find the reads in the set of reads coming from each region of the nucleic acid;
   c) for each respective region of the nucleic acid, choosing an initial estimate of the consensus of the reads coming from the respective region;
   d) computing a first statistical likelihood that a sequence whose identity is the initial estimate of the consensus was the sequence that generated the reads found to originate from the respective region of the nucleic acid, using a statistical model of the types of errors made in reading the nucleic acid sequence;
   e) perturbing the initial estimate of the consensus by applying a single-base mutation to the initial estimate of the consensus, such that the perturbation yields a second statistical likelihood that is greater than the first statistical likelihood before the perturbation; and
   f) repeating the steps (d) and (e) until the estimate is such that no perturbation yields a greater statistical likelihood.

9. The method of claim 8, wherein step (c) comprises using a graph-based algorithm.

10. The method of claim 1, wherein the consensus sequence is at least 99.99% accurate with respect to a reference sequence for the nucleic acid.

11. The method of claim 1, wherein the consensus sequence is at least 99.999% accurate with respect to a reference sequence for the nucleic acid.

12. The method of claim 1, wherein each read in the set of reads is from a single molecule real-time sequencing of the nucleic acid.

13. The method of claim 12, wherein a probability that the set of reads contains a read of length l is proportional to $\exp(-l/L)$.

14. The method of claim 1, wherein the generating, by the processor, the consensus sequence of the nucleic acid aligns the set of reads onto the one or more contigs.

15. A system for identifying a sequence of a nucleic acid, the system comprising:
   an input device configured to accept raw, single molecule real-time sequence data;
   an output device;
   a memory; and
   a processor, wherein the processor is configured to:
   obtain a set of reads for the nucleic acid sequence from the sequence data, wherein the set of reads have an average length (L) of at least 0.5 kb in length and wherein the set of reads collectively encompass at least 3 megabase pairs of the nucleic acid;
   select a plurality of seed reads from the set of reads by applying a predetermined length cutoff $l_{cutoff}$ to the set of reads wherein $l_{cutoff}$ is at least 1 kb;
   align each read in the set of reads to one or more seed reads in the plurality of seed reads, thereby producing a mini-assembly for each seed read that comprises a subset of the set of reads, thereby forming a plurality of mini-assemblies;
   create a respective pre-assembled read for each mini-assembly, by discarding those portions of each respective mini-assembly in the plurality of mini-assemblies that do not exhibit a minimum coverage with respect to the nucleic acid and by removing one or more insertion errors in the subset of reads of the mini-assembly thereby generating a set of pre-assembled reads;
   use a sequence assembler to assemble the set of pre-assembled reads into one or more contigs for the nucleic acid;
   generate a consensus sequence of the nucleic acid using the one or more contigs; and
   direct the consensus sequence for the nucleic acid to the output device, wherein the consensus sequence of the nucleic acid is at least 3 megabase pairs in length.

16. The system of claim 15, wherein a probability that the set of reads contains a read of length l is proportional to $\exp(-l/L)$.

17. The system of claim 15, wherein the consensus sequence of the nucleic acid is generated by alignment of the set of reads onto the one or more contigs.

18. A computer readable medium containing non-transitory program instructions for identifying a sequence of a nucleic acid when executed by a processor, the program instructions for:
   obtaining a set of reads for the nucleic acid sequence, wherein the set of reads have an average length (L) of at least 0.5 kb in length and wherein the set of reads collectively encompass at least 3 megabase pairs of the nucleic acid;

selecting a plurality of seed reads from the set of reads by applying a predetermined length cutoff $l_{cutoff}$ to the set of reads, wherein the $l_{cutoff}$ is at least 1 kb;

aligning each read in the set of reads to one or more seed reads in the plurality of seed reads, thereby producing a mini-assembly for each seed read that comprises a subset of the set of reads, thereby forming a plurality of mini-assemblies;

creating a respective pre-assembled read for each mini-assembly by discarding those portions of each respective mini-assembly in the plurality of mini-assemblies that do not exhibit a minimum coverage with respect to the nucleic acid and by removing one or more insertion errors in the subset of reads of the mini-assembly thereby generating a set of pre-assembled reads;

using a sequence assembler to assemble the set of pre-assembled reads into one or more contigs for the nucleic acid; and generating a consensus sequence of the nucleic acid using the one or more contigs, wherein the consensus sequence of the nucleic acid is at least 3 megabase pairs in length.

19. The computer readable medium of claim 18, wherein each read in the set of reads is from a single molecule real-time sequencing of the nucleic acid.

20. The computer readable medium of claim 19, wherein a probability that the set of reads contains a read of length l is proportional to exp(−l/L).

21. The computer readable medium of claim 18, wherein the consensus sequence of the nucleic acid is generated by alignment of the set of reads onto the one or more contigs.

* * * * *